US006927042B2

(12) United States Patent
Schultz et al.

(10) Patent No.: US 6,927,042 B2
(45) Date of Patent: Aug. 9, 2005

(54) GLYCOPROTEIN SYNTHESIS

(75) Inventors: Peter G. Schultz, La Jolla, CA (US);
Lei Wang, San Diego, CA (US);
Zhiwen Zhang, San Diego, CA (US)

(73) Assignee: The Scripps Research Institute, La Jolla, CA (US)

( * ) Notice: Subject to any disclaimer, the term of this patent is extended or adjusted under 35 U.S.C. 154(b) by 5 days.

(21) Appl. No.: 10/686,944

(22) Filed: Oct. 15, 2003

(65) Prior Publication Data

US 2004/0138106 A1 Jul. 15, 2004

Related U.S. Application Data

(60) Provisional application No. 60/441,450, filed on Jan. 16, 2003, provisional application No. 60/420,990, filed on Oct. 23, 2002, and provisional application No. 60/419,265, filed on Oct. 16, 2002.

(51) Int. Cl.$^7$ .......................... C12P 19/00; C12P 21/06
(52) U.S. Cl. ............................ 435/69.1; 435/72; 514/8; 530/395
(58) Field of Search .......................... 514/8; 435/69.1; 530/395

(56) References Cited

U.S. PATENT DOCUMENTS

| | | | |
|---|---|---|---|
| 5,369,017 A | 11/1994 | Wong et al. | |
| 6,331,418 B1 | 12/2001 | Roth | |
| 2003/0073157 A1 | 4/2003 | Bertozzi et al. | |
| 2003/0082575 A1 * | 5/2003 | Schultz et al. | .................. 435/6 |

FOREIGN PATENT DOCUMENTS

| | | |
|---|---|---|
| WO | WO 2002/085923 | 10/2002 |
| WO | WO 2002/086075 | 10/2002 |
| WO | WO 2003/031464 A2 | 4/2003 |

OTHER PUBLICATIONS

Rodriguez et al. J. Org. Chem. 63(21): 7134–7135 (1998).*
Kaushal, GP and Elbein, AD Arch Biochem Biophys 250(1):38–47 (1986) (Abstract Only).*
Palcic, M. Methods in Enzymology 230: 300–316 (1994).*
Anderson et al., Exploring the Limits of Codon and Anticodon Size, *Chemistry and Biology*, vol. 9, 237–244 (2002).
Arslan, T., et al., (1997) Structurally Modified Firefly Luciferase. Effects of Amino Acid Substitution at Position 286, *J. Am. Chem. Soc.* 119:10877.
Ayers, B., et al., (1999) Introduction of Unnatural Amino Acids into Proteins Using Expressed Protein Ligation, *Biopolymers* 51:343–354.
Begley, T. P., et al. (1997) Cofactor Biosynthesis: A Mechanistic Perspective, in *Top. Curr. Chem.*, eds. Leeper, F. J. & Vederas, J. C. (Springer–Verlag, New York), vol. 195, pp. 93–142.
Bertozzi, C. R., & L. L. Kiessling, (2001) Chemical Glycobiology, *Science* 291:2357.

Brick, P., et al. (1989) Structure of Tyrosyl–tRNA Sythetase Refined at 2–3 A Resolution: Interaction of the Enzyme with the Tyrosyl Adenylate Intermediate, *J. Mol. Biol.* 208:83–98.
Cao, S., et al., (1995) Stereoselective Phase Transfer Catalyzed Syntheses of Glycosyloxsuccinimides and their Transformation into Glycophrobes, *Tetrahedron* 51:6679–6686.
Chin, J. W. et al., (2002) Addition of p–Azido–L–phenylalanine to the Genetic Code of *Escherichia coli*, *J. Am. Chem. Soc.* 124:9026.
Chin, J. W. et al., (2002) Addition of photocrosslinking amino acid to the genetic code of *Escherichia coli*, *Proc. Natl. Acad. Sci. U S A* 99.
Chin, J. W. et al, (2003) An Expanded Eukaryotic Genetic Code, *Science*, 301:964–967.
Cornish, V. W., et al. (1996) Site–Specific Protein Modification Using a Ketone Handle, *J. Am. Chem. Soc.* 118:8150–8151.
Davis, B. G., (2002) Synthesis of Glycoproteins, *Chem. Rev.* 102:579.
Davis, N. J. and, Flitsch, S. L. (1991) A Novel Method for the Specific Glycosylation a Proteins, *Tetrahedron Lett.* 32:6793–6796.
Diaz, E., et al. (2001) Biogradation of Aromatic Compounds by *Escherichia coli*, *Microbiol. Mol. Biol. Rev.* 65: 523–569.
Dougherty, (2000) Unnatural Amino Acids as Probes of Protein Structure and Function, *Current Opinion in Chemical Biology*, 4:645–652.
Geoghegan, K. F. & Stroh, J. G. (1992) Site–Directed Conjugation of Nonpeptide Groups to Peptides and Proteins via Periodate Oxidation of a2–Amino Alcohol. Application to Modification at N–Terminal Serine, *Bioconjug. Chem.* 3:138–146.
Hang, H. C., & Bertozzi, C. R. (2001) Chemoselective Approaches to Gylcoprotein Assembly, *Acc. Chem. Res.* 34:727.
Kitagawa, H., and Paulson, J. C.(1994) Cloning of a Novel α2,3–Sialyltransferase That Sialylates Glycoprotein and Glycolipid Carbohydrate Groups, *J. Biol. Chem.* 269:1394–1401.
Lamarre–Vincent, N., & Hsieh–Wilson, L., (2003) Dynamic Glycosylation of the Transcription Factor CREB: A Potential Role in Gene Regulation, *J. Am. Chem. Soc.* 125:6612.

(Continued)

*Primary Examiner*—Jon Weber
*Assistant Examiner*—Anand Desai
(74) *Attorney, Agent, or Firm*—Quine Intellectual Property Law Group, P.C.

(57) ABSTRACT

Methods for making glycoproteins, both in vitro and in vivo, are provided. One method involves incorporating an unnatural amino acid into a protein and attaching one or more saccharide moieties to the unnatural amino acid. Another method involves incorporating an unnatural amino acid that includes a saccharide moiety into a protein. Proteins made by both methods can be further modified with additional sugars.

26 Claims, 5 Drawing Sheets

OTHER PUBLICATIONS

Liu, D.R. & Schultz, P.G. (1999) Progress toward the evolution of an organism with an expanded genetic code. *PNAS, USA* 96, 4780–4785.

Macmillan, D.; et al., (2002) Solid–Phase Synthesis of Thioether–Linked Glycopeptide Mimics for Application to Glycoprotein Semisynthesis, *Org Lett* 4:1467–1470.

Magliery, T.J. et al. (2001) Expanding the Genetic Code: Selection of Efficient Suppressors of Four–base Codons and Identification of "Shifty" Four–base Codons with a Library Approach in *Escherichia coli, J. Mol. Biol.* 307: 755–769.

Mahal, L. K., et al. (1997) Engineering Chemical Reactivity on Cell Surfaces Through Oligosaccharide Biosynthesis, *Science* 276: 1125–1128.

Muir, T. W., et al. (1998) Expressed protein ligation: A general method for protein engineering, *Proc. Natl. Acad. Sci. U S A* 95:6705–6710.

Okeley, N. M. & van der Donk, W. A. (2000) Novel cofactors via post–translational modification of enzyme active sites, *Chem. Biol.* 7:R159–R171.

Santoro, S. W., et al., (2002) An efficient system for the evolution of aminoacyl–tRNA synthetase specificity, *Nat. Biotechnol.* 20:1044.

Sears, P. & Wong, C. H. (2001) Toward Automated Synthesis of Oligosaccharides and Glycoproteins, *Science* 291:2344.

Shin, Y., et al., (1999) Fmoc–Bases Synthesis of Peptide–$^\alpha$Thioesters: Application to the Total Chemical Synthesis of Glycoprotein by Native Chemical Ligation, *J. Am. Chem. Soc.* 121:11684–11689.

Tolbert, T. J. and Wong, C.–H. (2000) Intein–Mediated Synthesis of Proteins Containing Carbohydrates and Other Molecular Probes, *J. Am. Chem. Soc.* 122:5421–5428.

Varki, A. (1993) Biological roles of oligosaccharides: all of the theories are correct, *Glycobiology* 3:97–130.

Wacker, M. et al., (2002) N–Linked Glycosylation in *Campylobacter jejuni* and Its Functional Transfer in *E. coli, Science* 298:1790.

Wang, L., et al. (2000) A New Functional Suppressor tRNA/Aminoacyl–tRNA Synthetase Pair for the in Vivo Incorporation of Unnatural Amino Acids into Proteins, *J. Am. Chem. Soc.* 122:5010–5011.

Wang, L. & Schultz, P. G. (2001) A general approach for the generation of orthogonal tRNAs, *Chem. Biol.* 8:883–890.

Wang, L., et al. (2001) Expanding the Genetic Code of *Escherichia coli, Science* 292: 498–500.

Wang, L., et al. (2002) Adding $_L$–3–(2–Naphthyl)alanine to the Genetic Code of *E. coli, J. Am. Chem. Soc.* 124(9):1836–1837.

Wang, L., et al., (2003) Addition of the keto functional group to the genetic code of *Escherichia coli, Proc. Natl. Acad. Sci. U.S.A.* 100(1):56–61.

Witte, K., et al., (1997) Enzymatic Glycoprotein Synthesis: Preparation of Ribonuclease Glycoforms via Enzymatic Glycopeptide Condensation and Glycosylation, *J. Am. Chem. Soc.* 119:2114–2118.

Witte, K., et al., (1998) Solution–and Solid–Phase Synthesis of N=Protected Glycopeptide Esters of the Benzyl Type as Substrates for Subtilisin–Catalyzed Glycopeptide Couplings, *J. Am. Chem. Soc.* 120:1979–1989.

Wells, L.et al., (2001) Glycosylation of Nucleocytoplasmic Proteins: Signal Transduction and O–GlcNAc, *Science* 291:2376.

Zhang, Z., et al. (2002) The Selective Incorporation of Alkenes into Proteins in *Escherichia coli, Angew. Chem. Int. Ed. Engl.* 41(15):2840–2842.

Zhang, Z. et al., (2003) A New Strategy for the Site–Specific Modification of Proteins in Vivo, *Biochemistry*, 42:6735–6746.

Hojo, H. & Nakahara, Y. (2000) Recent Progress in the Solid–phase Synthesis of Glycopeptide, *Current Protein and Peptide Science*, 1(1):23–48.

Schultz, M. & Kunz, H. (1995) Chemical and enxymatic synthesis of glycopeptides, *Interface between Chemistry and Biochemistry*, 73: 201–228.

* cited by examiner

Sequential route:

Convergent route:

GLYCOPROTEIN SYNTHESIS

CROSS-REFERENCE TO RELATED APPLICATIONS

This application claims priority to and benefit of U.S. provisional patent application Ser. No. 60/419,265, filed Oct. 16, 2002, U.S. provisional patent application Ser. No. 60/420,990, filed Oct. 23, 2002, and U.S. provisional patent application Ser. No. 60/441,450, filed Jan. 16, 2003, the specifications of which are incorporated herein in their entirety.

STATEMENT AS TO RIGHTS TO INVENTIONS MADE UNDER FEDERALLY SPONSORED RESEARCH AND DEVELOPMENT

This invention was made with government support under Grants GM44154, GM62159 and GM66494, all awarded by the National Institutes of Health, and under Grant DE-FG03-00ER45812, awarded by the Department of Energy (DOE). The Government has certain rights in the invention.

FIELD OF THE INVENTION

The invention is in the field of glycopeptides, glycoproteins, and related mimetics, and methods for synthesis of glycopeptides, glycoproteins, and related mimetics.

BACKGROUND OF THE INVENTION

The posttranslational modification of proteins by glycosylation can affect protein folding and stability, modify the intrinsic activity of proteins, and modulate their interactions with other biomolecules. See, e.g., Varki, A. (1993) *Glycobiology* 3:97–130. Natural glycoproteins are often present as a population of many different glycoforms, which makes analysis of glycan structure and the study of glycosylation effects on protein structure and function difficult. Therefore, methods for the synthesis of natural and unnatural homogeneously glycosylated proteins are needed for the systematic understanding of glycan function, and for the development of improved glycoprotein therapeutics.

One previously known approach for making proteins having desired glycosylation patterns makes use of glycosidases to convert a heterogeneous natural glycoprotein to a simple homogenous core, onto which saccharides can then be grafted sequentially with glycosyltransferases. See, e.g., Witte, K., et al., (1997) *J. Am. Chem. Soc.* 119:2114–2118. A limitation of this approach is that the primary glycosylation sites are predetermined by the cell line in which the protein is expressed. Alternatively, a glycopeptide containing the desired glycan structure can be synthesized by solid phase peptide synthesis. This glycopeptide can be coupled to other peptides or recombinant protein fragments to afford a larger glycoprotein by native chemical ligation, (see, e.g., Shin, Y., et al., (1999) *J. Am. Chem. Soc.* 121:11684–11689) expressed protein ligation, (see, e.g., Tolbert, T. J. and Wong, C.-H. (2000) *J. Am. Chem. Soc.* 122:5421–5428), or with engineered proteases. See, e.g., Witte, K., et al., (1998) *J. Am. Chem. Soc.* 120:1979–1989. Both native chemical ligation and expressed protein ligation are most effective with small proteins, and necessitate a cysteine residue at the N-terminus of the glycopeptide. When a protease is used to ligate peptides together, the ligation site must be placed far away from the glycosylation site for good coupling yields. See, e.g., Witte, K., et al., (1998) *J. Am. Chem. Soc.* 120:1979–1989. A third approach is to modify proteins with saccharides directly using chemical methods. Good selectivity can be achieved with haloacetamide saccharide derivatives, which are coupled to the thiol group of cysteine, (see, e.g., Davis, N. J. and, Flitsch, S. L. (1991) *Tetrahedron Lett.* 32:6793–6796; and, Macmillan, D.; et al., (2002) *Org Lett* 4:1467–1470), but this method can become problematic with proteins that have more than one cysteine residue.

Accordingly, a need exists for improved methods for making glycoproteins having a desired glycosylation pattern. The invention fulfills this and other needs, as will be apparent upon review of the following disclosure.

SUMMARY OF THE INVENTION

The invention provides methods for synthesis of glycoproteins. These methods involve, in some embodiments, incorporating into a protein an unnatural amino acid that comprises a first reactive group; and contacting the protein with a saccharide moiety that comprises a second reactive group, wherein the first reactive group reacts with the second reactive group to attach the saccharide moiety to the unnatural amino acid. Glycoproteins produced by these methods are also included in the invention. The first reactive group is, in some embodiments, an electrophilic moiety (e.g., a keto moiety, an aldehyde moiety, and/or the like) and the second reactive group is a nucleophilic moiety. In some embodiments, the first reactive group is a nucleophilic moiety and the second reactive group is an electrophilic moiety (e.g., a keto moiety, an aldehyde moiety, and/or the like). For example, an electrophilic moiety is attached to the saccharide moiety and the nucleophilic moiety is attached to the unnatural amino acid. The saccharide moiety can include a single carbohydrate moiety, or the saccharide moiety can include two or more carbohydrate moieties.

In some embodiments, the methods further involve contacting the saccharide moiety with a glycosyltransferase, a sugar donor moiety, and other reactants required for glycosyltransferase activity for a sufficient time and under appropriate conditions to transfer a sugar from the sugar donor moiety to the saccharide moiety. The product of this reaction can, if desired, be contacted by at least a second glycosyltransferase, together with the appropriate sugar donor moiety.

In certain embodiments, the method further comprises contacting the saccharide moiety with one or more of a β1-4N-acetylglucosaminyltransferase, an α1,3fucosyltransferase, an α1,2 fucosyltransferase, an α1,4fucosyltransferase, a β1-4galactosyltransferase, a sialyltransferase, and/or the like, to form a biantennary or triantennary oligosaccharide structure.

In one embodiment, the saccharide moiety comprises a terminal GlcNAc, the sugar donor moiety is UDP-Gal and the glycosyltransferase is a β-1,4-galactosyltransferase. In one embodiment, the saccharide moiety comprises a terminal GlcNAc, the sugar donor moiety is UDP-GlcNAc and the glycosyltransferase is a β1-4N-acetylglucosaminyltransferase. Optionally, the method further comprises contacting the product of the N-acetylglucosaminyltransferase reaction with a β1-4mannosyltransferase and GDP-mannose to form a saccharide moiety that comprises Manβ1-4GlcNAcβ1-4GlcNAc-. Optionally, the method further comprises contacting the Manβ1-4GlcNAcβ1-4GlcNAc-moiety with an α1-3mannosyltransferase and GDP-mannose to form a saccharide moiety that comprises Manα1-3Manβ1-4GlcNAcβ1-4GlcNAc-. Optionally, the method further comprises contacting the Manα1-3Manβ1-4GlcNAcβ1-4GlcNAc-moiety with an α1-6mannosyltransferase and GDP-mannose to form a saccharide moiety that comprises Manα1-6(Manα1-3)Manβ1-4GlcNAcβ1-4GlcNAc-. Optionally, the method further comprises contacting the Manα1-6(Manα1-3)Manβ1-4GlcNAcβ1-4GlcNAc-moiety with a β1-2N-acetylglucosaminyltransferase and UDP-GlcNAc to form a saccharide moiety that comprises Manα1-6(GlcNAcβ1-2Manα1-3)Manβ1-4GlcNAcβ1-4GlcNAc-. Optionally, the method further comprises contacting the Manα1-6(GlcNAcβ1-2Manα1-3)Manβ1-4GlcNAcβ1-4GlcNAc-moiety with a β1-2N-acetylglucosaminyltransferase and UDP-GlcNAc to form a saccharide moiety that comprises GlcNAcβ1-2Manα1-6 (GlcNAcβ1-2Manα1-3)Manβ1-4GlcNAcβ1-4GlcNAc-.

The step of incorporating into a protein an unnatural amino acid that comprises a first reactive group, in some embodiments, comprises using an orthogonal tRNA/orthogonal aminoacyl-tRNA synthetase (O-tRNA/O-RS) pair, where the O-tRNA recognizes a selector codon and incorporates the unnatural amino acid into the protein in response to the selector codon, and wherein the O-RS preferentially aminoacylates the O-tRNA with the unnatural amino acid. For example, the O-RS comprises an amino acid sequence comprising any one of SEQ ID NO.: 1, 2 or 3. Optionally, the O-tRNA comprises a mutRNA$_{CUA}^{Tyr}$. In some embodiments, the unnatural amino acid is incorporated into the polypeptide in vivo.

The invention also provides glycoproteins that comprise a saccharide moiety and a polypeptide. In certain embodiments in the glycoproteins of the invention, the saccharide moiety is attached to the polypeptide by a reaction product of a nucleophilic reaction between a first reactive group attached to an unnatural amino acid present in the polypeptide and a second reactive group attached to the saccharide moiety. In certain embodiments, the first reactive group is an electrophilic moiety (e.g., keto moiety, aldehyde moiety, and/or the like) and the second reactive group is a nucleophilic moiety.

In certain embodiments, the nucleophilic moiety of the invention includes, but is not limited to, hydrazide, hydroxylamine, semicarbazide, carbohydrazide, sulfonylhydrazide, and the like. For example, nucleophilic moieties include, but are not limited to, e.g., —NR$^1$—NH$_2$ (hydrazide), —NR$^1$(C=O)NR$^2$NH$_2$ (semicarbazide), —NR$^1$(C=S)NR$^2$NH$_2$ (thiosemicarbazide), —(C=O)NR$^1$NH$_2$ (carbonylhydrazide), —(C=S)NR$^1$NH$_2$ (thiocarbonylhydrazide), —(SO$_2$)NR$^1$NH$_2$ (sulfonylhydrazide), —NR$^1$NR$^2$(C=O)NR$^3$NH$_2$ (carbazide), NR$^1$NR$^2$(C=S)NR$^3$NH$_2$ (thiocarbazide), —O—NH$_2$ (hydroxylamine), and the like, where each R$^1$, R$^2$, and R$^3$ is independently H, or alkyl having 1–6 carbons.

In certain embodiments of the invention, a reaction product of the invention comprises, e.g., an oxime, an amide, a hydrazone, a reduced hydrazone, a carbohydrazone, a thiocarbohydrazone, a sufonylhydrazone, a semicarbazone, a thiosemicarbazone, and the like.

Other aspects of the invention include methods for synthesis of a glycoprotein by incorporating into a protein an unnatural amino acid that comprises a saccharide moiety. A glycoprotein produced by the method is also a feature of the invention. In certain embodiments, the incorporating step comprises using an orthogonal tRNA/orthogonal aminoacyl-tRNA synthetase (O-tRNA/O-RS) pair, wherein the O-tRNA recognizes a selector codon and incorporates the unnatural amino acid that comprises a saccharide moiety (e.g., a β-O-GlcNAc-L-serine, a tri-acetyl-β-GlcNAc-serine, a tri-O-acetyl-GalNAc-α-threonine, an α-GalNAc-L-threonine, and/or the like) into the protein in response to the selector codon, and wherein the O-RS preferentially aminoacylates the O-tRNA with the unnatural amino acid. In one embodiment, the incorporating step is performed in vivo. For example, the O-RS comprises an amino acid sequence comprising any one of SEQ ID NO.: 4, 5 or 6, or is encoded by a polynucleotide comprising a polynucleotide sequence of any one of SEQ ID NO.: 8, 9, or 10. Optionally, the O-tRNA comprises a mutRNA$_{CUA}^{Tyr}$. These methods can further involve contacting the saccharide moiety with a glycosyltransferase, a sugar donor moiety, and other reactants required for glycosyltransferase activity for a sufficient time and under appropriate conditions to transfer a sugar from the sugar donor moiety to the saccharide moiety.

In certain embodiments, the method further comprises contacting the product of the glycosyltransferase reaction with at least a second glycosyltransferase and a second sugar donor moiety. In one embodiment, the saccharide moiety comprises a terminal GlcNAc, the sugar donor moiety is UDP-GlcNAc and the glycosyltransferase is a β1-4N-acetylglucosaminyltransferase. In another embodiment, the saccharide moiety comprises a terminal GlcNAc, the sugar donor moiety is UDP-Gal and the glycosyltransferase is a β1-4-galactosyltransferase. Additional sugars can be added.

In certain embodiments, a glycosyltransferase of the invention includes, but is not limited to, e.g., a galactosyltransferase, a fucosyltransferase, a glucosyltransferase, an N-acetylgalactosaminyltransferase, an N-acetylglucosaminyltransferase, a glucuronyltransferase, a sialyltransferase, a mannosyltransferase, a glucuronic acid transferase, a galacturonic acid transferase, an oligosaccharyltransferase, and the like.

The invention also provides host cells (e.g., mammalian cells, yeast cells, bacterial cells, plant cells, fungal cells, archaebacterial cells, insect cells, and/or the like) that are useful for synthesizing a glycoprotein. These host cells contain: a) an unnatural amino acid that comprises a saccharide moiety; b) an orthogonal tRNA that recognizes a selector codon; c) an orthogonal aminoacyl tRNA synthetase (O-RS) that catalyzes attachment of the unnatural amino acid to the orthogonal tRNA; d) a polynucleotide that encodes a glycosyltransferase; and e) a polynucleotide sequence that encodes a polypeptide and comprises at least one selector codon.

Also provided by the invention are compositions that include a translation system. The translation systems include an orthogonal tRNA (O-tRNA) and an orthogonal aminoacyl tRNA synthetase (O-RS), wherein the O-RS preferentially aminoacylates the O-tRNA with an unnatural amino acid that comprises a saccharide moiety (e.g., a β-O-GlcNAc-L-serine, a tri-acetyl-β-GlcNAc-serine, a tri-O-acetyl-GalNAc-α-threonine, an α-GalNAc-L-threonine, and/or the like) and the O-tRNA recognizes at least one selector codon. In certain embodiments, the O-RS comprises an amino acid sequence comprising any one of SEQ ID NO.: 4, 5 or 6, or is encoded by a polynucleotide comprising a polynucleotide sequence of any one of SEQ ID NO.: 8, 9, or 10. Optionally, the O-tRNA comprises a mutRNA$_{CUA}^{Tyr}$.

Artificial (e.g., man-made, and not naturally occurring) polypeptides and polynucleotides are also features of the invention. For example, an artificial polypeptide of the invention includes, e.g., (a) a polypeptide that comprises an amino acid sequence as shown in any one of SEQ ID NO.: 4–6; (b) a polypeptide that comprises an amino acid sequence encoded by a polynucleotide sequence as shown in any one of SEQ ID NO.: 8–10; (c) a polypeptide that is specifically immunoreactive with an antibody specific for a polypeptide of (a), or (b); and, (d) an amino acid sequence comprising a conservative variation of (a), (b), or (c). Antibodies and antisera that are specifically immunoreactive with an artificial polypeptide of the invention are also provided. An artificial polynucleotide of the invention includes, e.g., (a) a polynucleotide comprising a nucleotide sequence as set forth in any one of SEQ ID NO.: 8–10; (b) a polynucleotide that is complementary to or that encodes a polynucleotide sequence of (a); (c) a polynucleotide encoding a polypeptide that comprises an amino acid sequence as set forth in any one of SEQ ID NO.: 1–6, or a conservative variation thereof; (d) a polynucleotide that encodes an artificial polypeptide; (e) a nucleic acid that hybridizes to a polynucleotide of (a), (b), (c), or (d) under highly stringent conditions over substantially the entire length of the nucleic acid; (f) a polynucleotide that is at least 98% identical to a polynucleotide of (a), (b), (c), (d), or (e); and, (h) a polynucleotide comprising a conservative variation of (a), (b), (c), (d), (e), or (f).

Definitions

Before describing the invention in detail, it is to be understood that this invention is not limited to particular devices or biological systems, which can, of course, vary. It is also to be understood that the terminology used herein is for the purpose of describing particular embodiments only, and is not intended to be limiting. As used in this specification and the appended claims, the singular forms "a", "an" and "the" include plural referents unless the content clearly dictates otherwise. Thus, for example, reference to "a cell" includes a combination of two or more cells; reference to "bacteria" includes mixtures of bacteria, and the like.

Orthogonal: As used herein, the term "orthogonal" refers to a molecule (e.g., an orthogonal tRNA (O-tRNA) and/or an orthogonal aminoacyl tRNA synthetase (O-RS)) that is used with reduced efficiency by a corresponding molecule that is endogenous to a cell or other translation system. Orthogonal refers to the inability or reduced efficiency, e.g., less than 20% efficiency, less than 10% efficiency, less than 5% efficiency, or less than 1% efficiency, of an orthogonal tRNA to function with an endogenous tRNA synthetase, or of an orthogonal RS to function with an endogenous tRNA in the translation system of interest. For example, an orthogonal tRNA in a translation system of interest is aminoacylated by any endogenous RS of a translation system of interest with reduced or even zero efficiency, when compared to aminoacylation of an endogenous tRNA by the endogenous RS. In another example, an orthogonal RS aminoacylates any endogenous tRNA in the translation system of interest with reduced or even zero efficiency, as compared to aminoacylation of the endogenous tRNA by an endogenous RS.

Preferentially aminoacylates: The term "preferentially aminoacylates" refers to an efficiency of, e.g., about 70% efficiency, about 75% efficiency, about 85% efficiency, about 90% efficiency, about 95% efficiency, or e.g., about 99% or more efficiency, at which an O-RS aminoacylates an O-tRNA with an unnatural amino acid compared to a naturally occurring tRNA or starting material used to generate the O-tRNA. The unnatural amino acid is then incorporated into a growing polypeptide chain with high fidelity, e.g., at greater than about 75% efficiency for a given selector codon, at greater than about 80% efficiency for a given selector codon, at greater than about 90% efficiency for a given selector codon, at greater than about 95% efficiency for a given selector codon, or at greater than about 99% or more efficiency for a given selector codon.

Selector codon: The term "selector codon" refers to codons recognized by an O-tRNA in the translation process and not typically recognized by an endogenous tRNA. The O-tRNA anticodon loop recognizes the selector codon on the mRNA and incorporates its amino acid, e.g., an unnatural amino acid, at this site in the polypeptide. Selector codons can include, e.g., nonsense codons, such as stop codons, e.g., amber, ochre, and opal codons; four or more base codons; codons derived from natural or unnatural base pairs and/or the like. For a given system, a selector codon can also include one of the natural three base codons, wherein the endogenous system does not use said natural three base codon, e.g., a system that is lacking a tRNA that recognizes the natural three base codon or a system wherein the natural three base codon is a rare codon.

Suppressor tRNA: A suppressor tRNA is a tRNA that alters the reading of a messenger RNA (mRNA) in a given translation system. A suppressor tRNA can read through, e.g., a stop codon, a four base codon, a rare codon, and/or the like.

Translation system: The term "translation system" refers to the components necessary to incorporate a naturally occurring amino acid into a growing polypeptide chain (protein). Components of a translation system can include, e.g., ribosomes, tRNAs, synthetases, mRNA and the like. The components of the invention can be added to a translation system, in vivo or in vitro. A translation system can be a cell, either prokaryotic, e.g., an *E. coli* cell, Archael cell, etc. or eukaryotic, e.g., a yeast, mammalian, plant, insect cell, etc.

Unnatural amino acid: As used herein, the term "unnatural amino acid" refers to any amino acid, modified amino acid, and/or amino acid analogue that is not one of the 20 naturally occurring amino acids or seleno cysteine or pyrrolysine.

Saccharide moiety: As used herein, the term "saccharide moiety" refers to natural and unnatural sugar moieties (i.e., a non-naturally occurring sugar moiety, e.g., a sugar moiety that is modified, e.g., at one or more hydroxyl or amino positions, e.g., dehydroxylated, deaminated, esterified, etc., e.g., 2-deoxyGal is an example of an unnatural sugar moiety). The term "carbohydrate" has the general formula $(CH_2O)_n$, and includes, but is not limited to, e.g., monosaccharides, disaccharides, oligosaccharides and polysaccharides. Oligosaccharides are chains composed of saccharide units, which are alternatively known as sugars. Saccharide units can be arranged in any order and the linkage between two saccharide units can occur in any of approximately ten different ways.

The following abbreviations are used herein:

Ara=arabinosyl;

Fru=fructosyl;

Fuc=fucosyl;

Gal=galactosyl;

GalNAc=N-acetylgalactosaminyl;

Glc=glucosyl;

GlcNAc=N-acetylglucosaminyl;

Man=mannosyl; and

NeuAc=sialyl (typically N-acetylneuraminyl).

Oligosaccharides are considered to have a reducing end and a non-reducing end, whether or not the saccharide at the reducing end is in fact a reducing sugar. In accordance with accepted nomenclature, oligosaccharides are depicted herein with the non-reducing end on the left and the reducing end on the right. All oligosaccharides described herein are described with the name or abbreviation for the non-reducing saccharide (e.g., Gal), followed by the configuration of the glycosidic bond (α or β), the ring bond, the ring position of the reducing saccharide involved in the bond, and then the name or abbreviation of the reducing saccharide (e.g., GlcNAc). The linkage between two sugars may be expressed, for example, as 2,3, 2→3, 2-3, or (2,3). Natural and unnatural linkages (e.g., 1-2, 1-3, 1-4, 1-6, 2-3, 2-4, 2-6, etc.) between two sugars are included in the invention. Each saccharide is a pyranose.

The term "sialic acid" (abbreviated "Sia") refers to any member of a family of nine-carbon carboxylated sugars. The most common member of the sialic acid family is N-acetylneuraminic acid (2-keto-5-acetamindo-3,5-dideoxy-D-glycero-D-galactononulopyranos-1-onic acid) (often abbreviated as Neu5Ac, NeuAc, or NANA). A second member of the family is N-glycolyl-neuraminic acid (Neu5Gc or NeuGc), in which the N-acetyl group of NeuAc is hydroxylated. A third sialic acid family member is 2-keto-3-deoxy-nonulosonic acid (KDN) (Nadano et al. (1986) *J. Biol. Chem.* 261: 11550–11557; Kanamori et al. (1990) *J. Biol. Chem.* 265: 21811–21819. Also included are 9-substituted sialic acids such as a 9-O-$C_1$–$C_6$ acyl-Neu5Ac like 9-O-lactyl-Neu5Ac or 9-O-acetyl-Neu5Ac, 9-deoxy-9-fluoro-Neu5Ac and 9-azido-9-deoxy-Neu5Ac. For review of the sialic acid family, see, e.g., Varki (1992) *Glycobiology* 2: 25–40; *Sialic Acids: Chemistry, Metabolism and Function*, R. Schauer, Ed. (Springer-Verlag, New York (1992). The synthesis and use of sialic acid compounds in a sialylation procedure is described in, for example, international application WO 92/16640, published Oct. 1, 1992.

Donor substrates for glycosyltransferases are activated nucleotide sugars. Such activated sugars generally consist of uridine and guanosine diphosphate, and cytidine monophosphate, derivatives of the sugars in which the nucleoside diphosphate or monophosphate serves as a leaving group. Bacterial, plant, and fungal systems can sometimes use other activated nucleotide sugars.

Unless otherwise defined herein or below in the remainder of the specification, all technical and scientific terms used herein have the same meaning as commonly understood by those of ordinary skill in the art to which the invention belongs.

DETAILED DESCRIPTION

Figure 1:
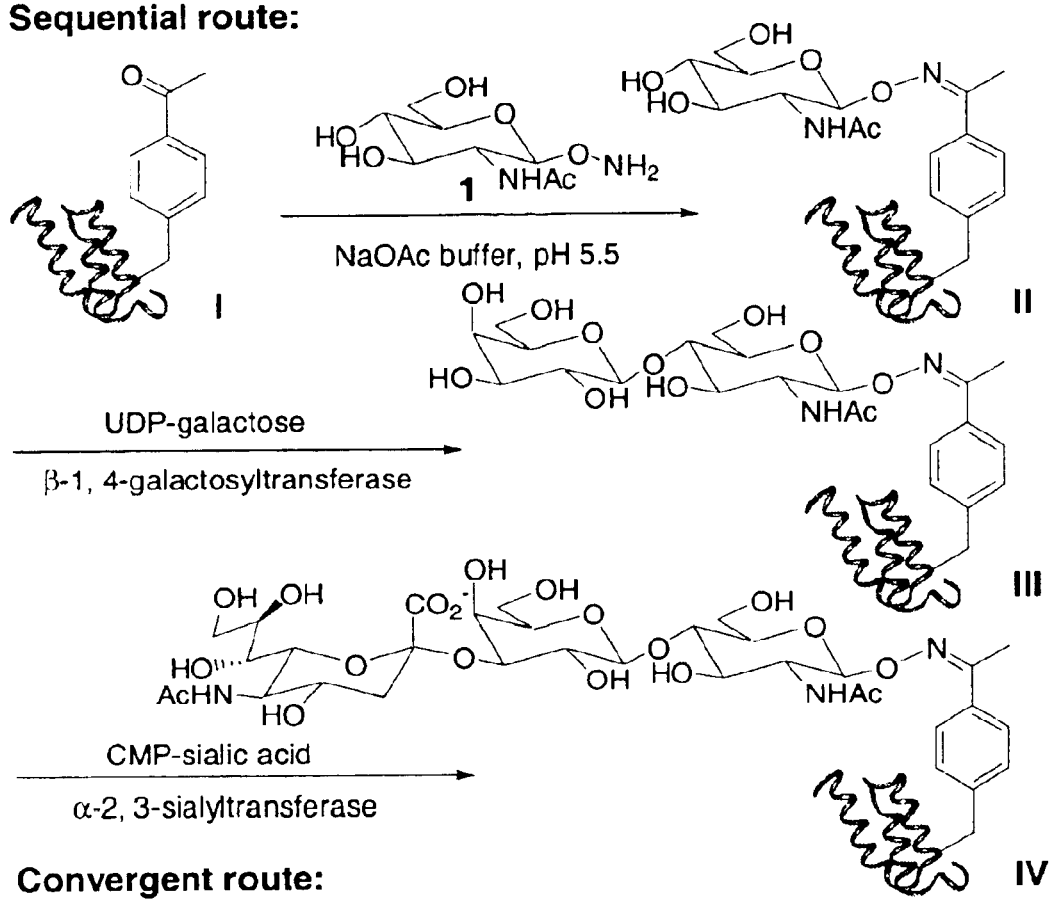
FIG. 1 schematically illustrates examples of two schemes (a sequential route and a convergent route) for attaching a saccharide moiety to a polypeptide that includes an unnatural amino acid.
Figure 1:
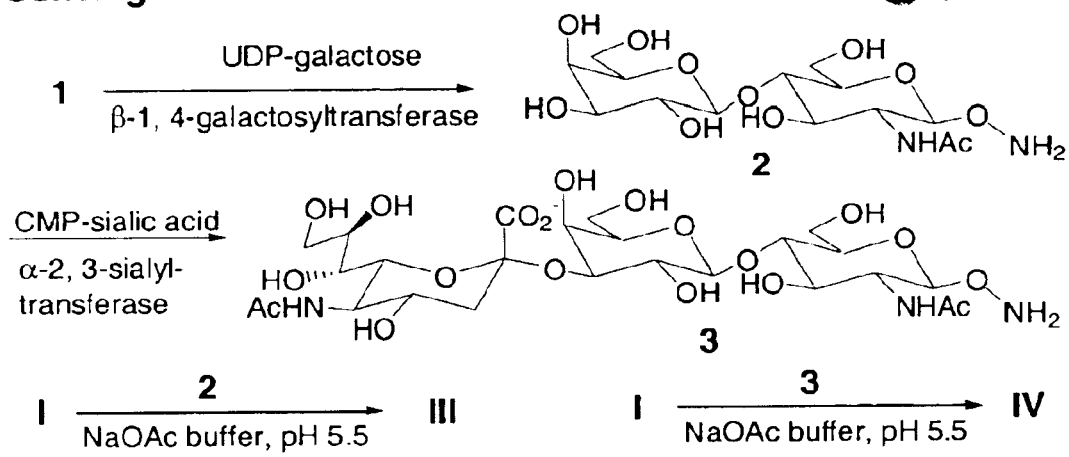

Posttranslational modifications of proteins regulate many biological processes, including metabolism, signal transduction, and gene expression. The synthetic challenges associated with generating homogeneous populations of selectively modified proteins, however, have hindered detailed studies of the effects of these modifications on protein structure and function. For example, glycosylation is one of the most common posttranslational modifications of proteins in eukaryotes and affects a wide range of protein functions from folding and secretion to biomolecular recognization and serum half life. See, e.g., R. A. Dwek, (1996) *Chem. Rev.* 96:683. While there have been significant advances in our understanding of the effects of glycosylation, the specific roles of oligosaccharide chains and the relationships between their structures and functions are just beginning to be understood. See, e.g., C. R. Bertozzi, & L. L. Kiessling, (2001) *Science* 291:2357. The primary challenge is that glycoproteins are typically produced as a mixture of glycoforms, making it difficult to isolate unique glycoforms from natural sources. A variety of methods have been developed to synthesize structurally defined glycoforms, but all impose severe restrictions on the size, quantity, and/or quality of the glycoprotein produced. See, e.g., P. Sears, & C. H. Wong, (2001) *Science* 291:2344; M. Wacker et al., (2002) *Science* 298:1790; B. G. Davis, (2002) *Chem. Rev.* 102:579; and, H. C. Hang, & C. R. Bertozzi, (2001) *Acc. Chem. Res.* 34:727. The invention solves this and other problems, and provides glycoproteins and glycoprotein mimetics, and methods for synthesis of glycoproteins having desired glycosylation patterns. The glycoproteins and glycoprotein mimetics of the invention have utility in producing homogeneous glycoforms of therapeutic glycoproteins and/or facilitating the studies on the structures and functions of glycosylated proteins.

Glycosylation

The invention provides methods for synthesizing glycoproteins. In certain embodiments, these methods involve incorporating into the protein an unnatural amino acid that comprises a first reactive group; and reacting the first reactive group with a second reactive group that is attached to a saccharide moiety, thereby forming a covalent bond and attaching the saccharide moiety to the protein.

A wide variety of suitable reactive groups are known to those of skill in the art. Such suitable reactive groups can include, for example, amino, hydroxyl, carboxyl, carboxylate, carbonyl, alkenyl, alkynyl, aldehyde, ester, ether (e.g. thio-ether), amide, amine, nitrile, vinyl, sulfide, sulfonyl, phosphoryl, or similarly chemically reactive groups. Additional suitable reactive groups include, but are not limited to, maleimide, N hydroxysuccinimide, sulfo-N-hydroxysuccinimide, nitrilotriacetic acid, activated hydroxyl, haloacetyl (e.g., bromoacetyl, iodoacetyl), activated carboxyl, hydrazide, epoxy, aziridine, sulfonylchloride, trifluoromethyldiaziridine, pyridyldisulfide, N-acyl-imidazole, imidazolecarbamate, vinylsulfone, succinimidylcarbonate, arylazide, anhydride, diazoacetate, benzophenone, isothiocyanate, isocyanate, imidoester, fluorobenzene, biotin and avidin.

In some embodiments, one of the reactive groups is an electrophilic moiety, and the second reactive group is a nucleophilic moiety. Either the nucleophilic moiety or the electrophilic moiety can be attached to the side chain of the unnatural amino acid; the corresponding group is then attached to the saccharide moiety. Suitable electrophilic moieties that react with nucleophilic moieties to form a covalent bond are known to those of skill in the art. Such electrophilic moieties include, but are not limited to, e.g., carbonyl group, a sulfonyl group, an aldehyde group, a ketone group, a hindered ester group, a thioester group, a stable imine group, an epoxide group, an aziridine group, etc. Suitable nucleophilic moieties that can react with electrophilic moiety are known to those of skill in the art. Such nucleophiles include, for example, aliphatic or aromatic amines, such as ethylenediamine. In other embodiments, the reactive group is —NR$^1$—NH$_2$ (hydrazide), —NR$^1$(C=O)NR$^2$NH$_2$ (semicarbazide), —NR$^1$(C=S)NR$^2$NH$_2$ (thiosemicarbazide), —(C=O)NR$^1$NH$_2$ (carbonylhydrazide), —(C=S) NR$^1$NH$_2$ (thiocarbonylhydrazide), —(SO$_2$)NR$^1$NH$_2$ (sulfonylhydrazide), —NR$^1$NR$^2$(C=O)NR$^3$NH$_2$ (carbazide), —NR$^1$NR$^2$(C=S)NR$^3$NH$_2$ (thiocarbazide), —O—NH$_2$ (hydroxylamine), and/or the like, where each R$^1$, R$^2$, and R$^3$ is independently H, or an alkyl moiety having 1–6 carbons, preferably H. In one aspect of the invention, the reactive group is a hydrazide, hydroxylamine, semicarbazide, carbohydrazide, a sulfonylhydrazide, or the like.

The product of the reaction between the nucleophile and the electrophilic moiety typically incorporates the atoms originally present in the nucleophilic moiety. Typical linkages obtained by reacting the aldehydes or ketones with the nucleophilic moieties include reaction products such as an oxime, an amide, a hydrazone, a reduced hydrazone, a carbohydrazone, a thiocarbohydrazone, a sufonylhydrazone, a semicarbazone, a thiosemicarbazone, or similar functionality, depending on the nucleophilic moiety used and the electrophilic moiety (e.g., aldehyde, ketone, and/or the like) that is reacted with the nucleophilic moiety. Linkages with carboxylic acids are typically referred to as carbohydrazides or as hydroxamic acids. Linkages with sulfonic acids are typically referred to as sulfonylhydrazides or N-sulfonylhydroxylamines. The resulting linkage can be subsequently stabilized by chemical reduction.

In certain embodiments, the glycoprotein is synthesized by incorporating an unnatural amino acid, to which is attached a saccharide moiety, into a polypeptide. For example, an orthogonal O-tRNA/O-RS can be utilized that incorporates the unnatural amino acid with the saccharide moiety into a growing polypeptide chain in response to a selector codon. See, e.g., section herein entitled "Preparation of Proteins Having an Unnatural Amino Acid."

Glycosyltransferases

The invention provides methods in which an amino acid-linked saccharide moiety or an unnatural amino acid that includes a saccharide moiety is further glycosylated. These glycosylation steps are preferably carried out enzymatically using, for example, a glycosyltransferase, glycosidase, or other enzyme known to those of skill in the art. In some embodiments, a plurality of enzymatic steps are carried out in a single reaction mixture that contains two or more different glycosyltransferases. For example, one can conduct a galactosylating and a sialylating step simultaneously by including both sialyltransferase and galactosyltransferase in the reaction mixture.

For enzymatic saccharide syntheses that involve glycosyltransferase reactions, the recombinant cells of the invention optionally contain at least one heterologous gene that encodes a glycosyltransferase. Many glycosyltransferases are known, as are their polynucleotide sequences. See, e.g., "The WWW Guide To Cloned Glycosyltransferases," (available on the World Wide Web at vei.co.uk forward slash TON forward slash gt guide(dot)htm). Glycosyltransferase amino acid sequences and nucleotide sequences encoding glycosyltransferases from which the amino acid sequences can be deduced are also found in various publicly available databases, including GenBank, Swiss-Prot, EMBL, and others.

Glycosyltransferases that can be employed in the cells of the invention include, but are not limited to, galactosyltransferases, fucosyltransferases, glucosyltransferases, N-acetylgalactosaminyltransferases, N-acetylglucosaminyltransferases, glucuronyltransferases, sialyltransferases, mannosyltransferases, glucuronic acid transferases, galacturonic acid transferases, oligosaccharyltransferases, and the like. Suitable glycosyltransferases include those obtained from eukaryotes, as well as from prokaryotes.

An acceptor for the glycosyltransferases will be present on the glycoprotein to be modified by the methods of the invention. Suitable acceptors, include, for example, galactosyl acceptors such as Galβ1,4GalNAc-, Galβ1,3GalNAc-, lacto-N-tetraose-, Galβ1,3GlcNAc-, Galβ1,4GlcNAc-, Galβ1,3Ara-, Galβ1,6GlcNAc-, and Galβ1,4Glc-(lactose). Other acceptors known to those of skill in the art (see, e.g., Paulson et al. (1978) *J. Biol. Chem.* 253: 5617–5624). Typically, the acceptors form part of a saccharide moiety chain that is attached to the glycoprotein.

Enzyme amounts or concentrations are expressed in activity Units, which is a measure of the initial rate of catalysis. One activity Unit catalyzes the formation of 1 μmol of product per minute at a given temperature (typically 37° C.) and pH value (typically 7.5). Thus, 10 Units of an enzyme is a catalytic amount of that enzyme where 10 μmols of substrate are converted to 10 μmol of product in one minute at a temperature of 37° C. and a pH value of 7.5. The enzymes can be utilized free in solution or can be bound to a support such as a polymer. The reaction mixture is thus substantially homogeneous at the beginning, although some precipitate can form during the reaction.

The glycosylation reactions include, in addition to the appropriate glycosyltransferase and acceptor, an activated nucleotide sugar that acts as a sugar donor for the glycosyltransferase. The reactions can also include other ingredients that facilitate glycosyltransferase activity. These ingredients can include a divalent cation (e.g., Mg$^{+2}$ or Mn$^{+2}$), materials necessary for ATP regeneration, phosphate ions, and organic solvents. The concentrations or amounts of the various reactants used in the processes depend upon numerous factors including reaction conditions such as temperature and pH value, and the choice and amount of acceptor saccharides to be glycosylated. The reaction medium may also comprise solubilizing detergents (e.g., Triton or SDS) and organic solvents such as methanol or ethanol, if necessary.

Oligosaccharides produced using the methods of the invention can be analyzed by methods that are known to those of skill in the art. For example, the carbohydrate units can be released from the carbohydrate moieties by alkaline β-elimination, for example, and separated from the polypeptide by gel filtration. The resulting oligosaccharides are then separated from each other using a one or more standard techniques, such as of gel filtration, HPLC, thin layer chromatography, and ion exchange chromatography, or a combination thereof, and can be fully analyzed. Complete structural analysis of the purified oligosaccharide units requires the determination of the monosaccharide units, their ring form, configuration (D or L), anomeric linkage (α or β), the positions of the linkages between the sugars and their sequence. In addition, the position of any substituent groups are established. Methylation analysis can be used to determine the positions of the glycosidic linkages between the monosaccharides. The anomeric configuration of the sugar residues can be addressed using, e.g., $^1$H NMR spectroscopy. The conditions and methods used to perform a complete structural carbohydrate analysis are described generally in Beeley, *Laboratory Techniques in Biochemistry and Molecular Biology*, eds. Burdon and Knippenberg, Elsevier, Amsterdam (1985), Hounsell, *"Glycoanalysis Protocols"*, *Meth. Mol. Biol.* Vol. 76, 1998, and El Rassi, *Carbohydrate Analysis: High Performance Liquid Chromatography and Capillary Electrophoresis*, Elsevier Science Ltd, Vol. 58 (1994).

Additional techniques to fully characterize the sugars of an oligosaccharide include FAB-MS (fast atom bombardment-mass spectrometry), HPAE (high pH anion exchange chromatography) and NMR (nuclear magnetic resonance spectroscopy, particularly $^1$H-NMR and $^{13}$C-NMR). These techniques are complementary. Examples of how these techniques are used to fully characterize the structure of an oligosaccharide can be found in the analysis by Spellman et al., (1989) *J. Biol. Chem.* 264: 14100, and Stanley et al. (1988) *J. Biol. Chem.* 263: 11374. Other methods include positive ion fast atom bombardment mass spectroscopy (FAB-MS) and methylation analysis by gas chromatography-electron impact mass spectroscopy (GC/EI-MS) (see EPO Application No. 89305153.2).

In Vivo Synthesis of Glycoproteins

To synthesize a glycoprotein in vivo, one can introduce into an expression vector a polynucleotide that encodes a polypeptide of interest. The polynucleotide also includes one or more selector codons at the positions at which attachment of a saccharide moiety is desired. The expression vector is introduced into a host cell that includes an unnatural amino acid, e.g., an unnatural amino acid comprising a moiety where a saccharide moiety can be attached, such as an aldehyde- or keto-derivatized amino acid, or an unnatural amino acid that includes a saccharide moiety; an orthogonal tRNA that recognizes the selector codon; and an orthogonal aminoacyl tRNA synthetase (O-RS) that catalyzes attachment of the unnatural amino acid to the orthogonal tRNA. The O-RS attaches the unnatural amino acid to the orthogonal tRNA, which then introduces the unnatural amino acid into the nascent protein.

In some embodiments, the host cell further includes one or more polynucleotides that encode glycosyltransferases. Such host cells can catalyze the addition of one or more sugars to the saccharide moiety that is attached to the unnatural amino acid.

Several well-known methods of introducing target nucleic acids into bacterial cells are available, any of which can be used in the invention. These include: fusion of the recipient cells with bacterial protoplasts containing the DNA, electroporation, projectile bombardment, and infection with viral vectors, etc. Bacterial cells can be used to amplify the number of plasmids containing DNA constructs of this invention. The bacteria are grown to log phase and the plasmids within the bacteria can be isolated by a variety of methods known in the art (see, for instance, Sambrook, infra). In addition, a plethora of kits are commercially available for the purification of plasmids from bacteria, (see, e.g., EasyPrep™, FlexiPrep™, both from Pharmacia Biotech; StrataClean™, from Stratagene; and, QIAprep™ from Qiagen). The isolated and purified plasmids are then further manipulated to produce other plasmids, used to transfect cells or incorporated into related vectors to infect organisms.

The engineered host cells can be cultured in conventional nutrient media modified as appropriate for such activities as, for example, screening steps, activating promoters or selecting transformants. These cells can optionally be cultured into transgenic organisms.

Other useful references, e.g. for cell isolation and culture (e.g., for subsequent nucleic acid isolation) include Freshney (1994) *Culture of Animal Cells, a Manual of Basic Technique*, third edition, Wiley-Liss, New York and the references cited therein; Payne et al. (1992) *Plant Cell and Tissue Culture in Liquid Systems*, John Wiley & Sons, Inc. New York, N.Y.; Gamborg and Phillips (eds) (1995) *Plant Cell, Tissue and Organ Culture*; Fundamental Methods Springer Lab Manual, Springer-Verlag (Berlin Heidelberg New York) and Atlas and Parks (eds) *The Handbook of Microbiological Media* (1993) CRC Press, Boca Raton, Fla.

General texts which describe molecular biological techniques include Berger and Kimmel, *Guide to Molecular Cloning Techniques, Methods in Enzymology* volume 152 Academic Press, Inc., San Diego, Calif. (Berger); Sambrook et al., *Molecular Cloning—A Laboratory Manual* (3rd Ed.), Vol. 1–3, Cold Spring Harbor Laboratory, Cold Spring Harbor, N.Y., 2001 ("Sambrook") and *Current Protocols in Molecular Biology*, F. M. Ausubel et al., eds., *Current Protocols*, a joint venture between Greene Publishing Associates, Inc. and John Wiley & Sons, Inc., (supplemented through 2003) ("Ausubel")). These texts describe mutagenesis, the use of vectors, promoters and many other relevant topics related to, e.g., the generation of genes that include selector codons for production of proteins that include unnatural amino acids, orthogonal tRNAs, orthogonal synthetases, and pairs thereof.

Preparation of Proteins Having an Unnatural Amino Acid

Features of the invention include producing glycoproteins that include an unnatural amino acid, e.g., an unnatural amino acid comprising a moiety where a saccharide moiety can be attached, or an unnatural amino acid that includes a saccharide moiety. In certain embodiments, the invention involves producing glycoproteins that include one or more unnatural amino acids to which are attached suitable reactive groups that can form a covalent bond when reacted with a second reactive group. In some embodiments, the unnatural amino acids comprise an electrophilic moiety, e.g., aldehyde- or keto-derivatized amino acids, and the aldehyde- or keto-moieties are reacted with a nucleophilic moiety to attach a saccharide moiety to the polypeptide or protein. The unnatural amino acid-containing proteins are synthesized by cells in which the protein biosynthetic machinery has been altered to accommodate additional genetically encoded amino acids using orthogonal tRNA/aminoacyl tRNA synthetase (O-tRNA/O-RS) pairs. In particular, the cells include an orthogonal tRNA that recognizes a selector codon (e.g., stop codons, four base codons, and the like), and an orthogonal aminoacyl tRNA synthetase that can attach an aldehyde- or keto-derivatized amino acid to the orthogonal tRNA.

In certain embodiments, the invention involves producing glycoproteins that include one or more unnatural amino acids that includes a saccharide moiety. The unnatural amino acid-containing proteins are synthesized by cells in which the protein biosynthetic machinery has been altered to accommodate additional genetically encoded amino acids using orthogonal tRNA/aminoacyl tRNA synthetase (O-tRNA/O-RS) pairs. In particular, the cells include an orthogonal tRNA that recognizes a selector codon (e.g., stop codons, four base codons, and the like), and an orthogonal aminoacyl tRNA synthetase that can attach the unnatural amino acid with the saccharide moiety to the orthogonal tRNA.

This technology allows the site-specific incorporation of the unnatural amino acids directly into proteins in vivo. Importantly, the unnatural amino acid is added to the genetic repertoire, rather than substituting for one of the common 20 amino acids. The protein can have one or multiple (the same or different) unnatural amino acids at a particular position in the protein. Unlike earlier methods for derivatizing proteins, the use of O-tRNA/O-RS pairs allows one to make proteins having an unnatural amino acid at only one of the locations at which a particular amino acid occurs in a protein, if desired, rather than derivatizing that particular amino acid at each location at which it occurs in a protein.

To make a glycoprotein, one can use host cells and organisms that are adapted for the in vivo incorporation of the unnatural amino acid via orthogonal tRNA/RS pairs. Host cells are genetically engineered (e.g., transformed, transduced or transfected) with one or more vectors that express the orthogonal tRNA, the orthogonal tRNA synthetase, and a vector that encodes the protein to be derivatized. Each of these components can be on the same vector, or each can be on a separate vector, two components can be on one vector and the third component on a second vector. The vector can be, for example, in the form of a plasmid, a bacterium, a virus, a naked polynucleotide, or a conjugated polynucleotide.

The coding regions for the orthogonal tRNA, the orthogonal tRNA synthetase, and the protein to be derivatized are operably linked to gene expression control elements that are functional in the desired host cell. Typical vectors contain transcription and translation terminators, transcription and translation initiation sequences, and promoters useful for regulation of the expression of the particular target nucleic acid. The vectors optionally comprise generic expression cassettes containing at least one independent terminator sequence, sequences permitting replication of the cassette in eukaryotes, or prokaryotes, or both (e.g., shuttle vectors) and selection markers for both prokaryotic and eukaryotic systems. Vectors are suitable for replication and/or integration in prokaryotes, eukaryotes, or preferably both. See Giliman & Smith, *Gene* 8:81 (1979); Roberts, et al., *Nature*, 328:731 (1987); Schneider, B., et al., *Protein Expr. Purif.* 6435:10 (1995); Berger and Kimmel, supra; Sambrook, supra, and Ausubel, supra. A catalogue of Bacteria and Bacteriophages useful for cloning is provided, e.g., by the ATCC, e.g., *The ATCC Catalogue of Bacteria and Bacteriophage* (1992) Gherna et al. (eds) published by the ATCC. Additional basic procedures for sequencing, cloning and other aspects of molecular biology and underlying theoretical considerations are also found in Watson et al. (1992) *Recombinant DNA Second Edition* Scientific American Books, NY. Proteins and Polypeptides of Interest.

For example, methods for producing glycoproteins include growing, in an appropriate medium, the cell, where the cell comprises a nucleic acid that comprises at least one selector codon and encodes a protein, providing an unnatural amino acid, e.g., an unnatural amino acid comprising a moiety where a saccharide moiety can be attached, or an unnatural amino acid that includes a saccharide moiety, and incorporating the unnatural amino acid into the specified position in the protein during translation of the nucleic acid with the at least one selector codon, thereby producing the protein. The cell further comprises: an orthogonal-tRNA (O-tRNA) that functions in the cell and recognizes the selector codon; and, an orthogonal aminoacyl-tRNA synthetase (O-RS) that preferentially aminoacylates the O-tRNA with the unnatural amino acid, e.g., an unnatural amino acid comprising a moiety where a saccharide moiety can be attached, or an unnatural amino acid that includes a saccharide moiety. The publication WO 2002/085923, entitled "IN VIVO INCORPORATION OF UNNATURAL AMINO ACIDS" describes this process and is incorporated herein by reference. For example, when an O-tRNA/O-RS pair is introduced into a host the pair leads to the in vivo incorporation of unnatural amino acid, e.g., an unnatural amino acid comprising a moiety where a saccharide moiety can be attached, or an unnatural amino acid that includes a saccharide moiety, which can be exogenously added to the growth medium, into a protein, in response to a selector codon. Optionally, the compositions of the invention can be in an in vitro translation system, or in an in vivo system(s). See also corresponding application PCT/US03/32576 entitled "Site Specific Incorporation of Keto Amino Acids into Proteins," filed Oct. 15, 2003, which is incorporated by reference.

A cell of the invention provides the ability to synthesize or produce glycoproteins in large useful quantities. In one aspect, the composition optionally includes, e.g., at least 10 micrograms, at least 50 micrograms, at least 75 micrograms, at least 100 micrograms, at least 200 micrograms, at least 250 micrograms, at least 500 micrograms, at least 1 milligram, at least 10 milligrams or more of the glycoprotein, or an amount that can be achieved with in vivo protein production methods (details on recombinant protein production and purification are provided herein). In another aspect, the protein is optionally present in the composition at a concentration of, e.g., at least 10 micrograms of protein per liter, at least 50 micrograms of protein per liter, at least 75 micrograms of protein per liter, at least 100 micrograms of protein per liter, at least 200 micrograms of protein per liter, at least 250 micrograms of protein per liter, at least 500 micrograms of protein per liter, at least 1 milligram of protein per liter, or at least 10 milligrams of protein per liter or more, in, e.g., a cell lysate, a buffer, a pharmaceutical buffer, or other liquid suspension (e.g., in a volume of, e.g., anywhere from about 1 nl to about 100 L). The production of large quantities (e.g., greater that that typically possible with other methods, e.g., in vitro translation) of a protein in a cell including at least one unnatural amino acid, e.g., an unnatural amino acid comprising a moiety where a saccharide moiety can be attached, or an unnatural amino acid that includes a saccharide moiety is a feature of the invention.

The incorporation of an unnatural amino acid, e.g., an unnatural amino acid comprising a moiety where a saccharide moiety can be attached, or an unnatural amino acid that includes a saccharide moiety, can be done to, e.g., tailor changes in protein structure and/or function, e.g., to change size, acidity, nucleophilicity, hydrogen bonding, hydrophobicity, accessibility of protease target sites, target access to a protein moiety, etc. Proteins that include an unnatural amino acid, e.g., an unnatural amino acid comprising a moiety where a saccharide moiety can be attached, or an unnatural amino acid that includes a saccharide moiety, can have enhanced, or even entirely new, catalytic or physical properties. For example, the following properties are optionally modified by inclusion of an unnatural amino acid, e.g., an unnatural amino acid comprising a moiety where a saccharide moiety can be attached, or an unnatural amino acid that includes a saccharide moiety into a protein: toxicity, biodistribution, structural properties, spectroscopic properties, chemical and/or photochemical properties, catalytic ability, half-life (e.g., serum half-life), ability to react with other molecules, e.g., covalently or noncovalently, and the like. The compositions including proteins that include at least one unnatural amino acid, e.g., an unnatural amino acid comprising a moiety where a saccharide moiety can be attached, or an unnatural amino acid that includes a saccharide moiety are useful for, e.g., novel therapeutics, diagnostics, catalytic enzymes, industrial enzymes, binding proteins (e.g., antibodies), and e.g., the study of protein structure and function. See, e.g., Dougherty, (2000) *Unnatural Amino Acids as Probes of Protein Structure and Function, Current Opinion in Chemical Biology*, 4:645–652.

In one aspect of the invention, a composition includes at least one protein with at least one, e.g., at least two, at least three, at least four, at least five, at least six, at least seven, at least eight, at least nine, or at least ten or more unnatural amino acids, e.g., an unnatural amino acid comprising a moiety where a saccharide moiety can be attached, or an unnatural amino acid that includes a saccharide moiety, and/or which include another unnatural amino acid. The unnatural amino acids can be the same or different, e.g., there can be 1, 2, 3, 4, 5, 6, 7, 8, 9, or 10 or more different sites in the protein that comprise 1, 2, 3, 4, 5, 6, 7, 8, 9, or 10 or more different unnatural amino acids. In another aspect, a composition includes a protein with at least one, but fewer than all, of a particular amino acid present in the protein substituted with the unnatural amino acid, e.g., an unnatural amino acid comprising a moiety where a saccharide moiety can be attached, or an unnatural amino acid that includes a saccharide moiety. For a given protein with more than one unnatural amino acids, the unnatural amino acids can be identical or different (e.g., the protein can include two or more different types of unnatural amino acids, or can include two of the same unnatural amino acid). For a given protein with more than two unnatural amino acids, the unnatural amino acids can be the same, different, or a combination of multiple unnatural amino acids of the same kind with at least one different unnatural amino acid.

Essentially any protein (or portion thereof) that includes an unnatural amino acid, e.g., an unnatural amino acid comprising a moiety where a saccharide moiety is attached, such as an aldehyde- or keto-derivatized amino acid, or an unnatural amino acid that includes a saccharide moiety (and any corresponding coding nucleic acid, e.g., which includes one or more selector codons) can be produced using the compositions and methods herein. No attempt is made to identify the hundreds of thousands of known proteins, any of which can be modified to include one or more unnatural amino acid, e.g., by tailoring any available mutation methods to include one or more appropriate selector codon in a relevant translation system. Common sequence repositories for known proteins include GenBank EMBL, DDBJ and the NCBI. Other repositories can easily be identified by searching the internet.

Typically, the proteins are, e.g., at least 60%, at least 70%, at least 75%, at least 80%, at least 90%, at least 95%, or at least 99% or more identical to any available protein (e.g., a therapeutic protein, a diagnostic protein, an industrial enzyme, or portion thereof, and the like), and they comprise one or more unnatural amino acid. Examples of therapeutic, diagnostic, and other proteins that can be modified to comprise one or more unnatural amino acid, e.g., an unnatural amino acid comprising a moiety where a saccharide moiety is attached, or an unnatural amino acid that includes a saccharide moiety, can be found, but not limited to, those in WO 2002/085923, supra. Examples of therapeutic, diagnostic, and other proteins that can be modified to comprise one or more unnatural amino acid that comprises an amino acid, where a saccharide moiety is linked and/or an unnatural amino acid that includes a saccharide moiety include, but are not limited to, e.g., Alpha-1 antitrypsin, Angiostatin, Antihemolytic factor, antibodies (further details on antibodies are found below), Apolipoprotein, Apoprotein, Atrial natriuretic factor, Atrial natriuretic polypeptide, Atrial peptides, C-X-C chemokines (e.g., T39765, NAP-2, ENA-78, Gro-a, Gro-b, Gro-c, IP-10, GCP-2, NAP-4, SDF-1, PF4, MIG), Calcitonin, CC chemokines (e.g., Monocyte chemoattractant protein-1, Monocyte chemoattractant protein-2, Monocyte chemoattractant protein-3, Monocyte inflammatory protein-1 alpha, Monocyte inflammatory protein-1 beta, RANTES, I309, R83915, R91733, HCC1, T58847, D31065, T64262), CD40 ligand, C-kit Ligand, Collagen, Colony stimulating factor (CSF), Complement factor 5a, Complement inhibitor, Complement receptor 1, cytokines, (e.g., epithelial Neutrophil Activating Peptide-78, GROα/MGSA, GROβ, GROγ, MIP-1α, MIP-1δ, MCP-1), Epidermal Growth Factor (EGF), Erythropoietin ("EPO", representing a preferred target for modification by the incorporation of one or more unnatural amino acid), Exfoliating toxins A and B, Factor IX, Factor VII, Factor VIII, Factor X, Fibroblast Growth Factor (FGF), Fibrinogen, Fibronectin, G-CSF, GM-CSF, Glucocerebrosidase, Gonadotropin, growth factors, Hedgehog proteins (e.g., Sonic, Indian, Desert), Hemoglobin, Hepatocyte Growth Factor (HGF), Hirudin, Human serum albumin, Insulin, Insulin-like Growth Factor (IGF), interferons (e.g., IFN-α, IFN-β, IFN-γ), interleukins (e.g., IL-1, IL-2, IL-3, IL-4, IL-5, IL-6, IL-7, IL-8, IL-9, IL-10, IL-11, IL-12, etc.), Keratinocyte Growth Factor (KGF), Lactoferrin, leukemia inhibitory factor, Luciferase, Neurturin, Neutrophil inhibitory factor (NIF), oncostatin M, Osteogenic protein, Parathyroid hormone, PD-ECSF, PDGF, peptide hormones (e.g., Human Growth Hormone), Pleiotropin, Protein A, Protein G, Pyrogenic exotoxins A, B, and C, Relaxin, Renin, SCF, Soluble complement receptor I, Soluble I-CAM 1, Soluble interleukin receptors (IL-1, 2, 3, 4, 5, 6, 7, 9, 10, 11, 12, 13, 14, 15), Soluble TNF receptor, Somatomedin, Somatostatin, Somatotropin, Streptokinase, Superantigens, i.e., Staphylococcal enterotoxins (SEA, SEB, SEC1, SEC2, SEC3, SED, SEE), Superoxide dismutase (SOD), Toxic shock syndrome toxin (TSST-1), Thymosin alpha 1, Tissue plasminogen activator, Tumor necrosis factor beta (TNF beta), Tumor necrosis factor receptor (TNFR), Tumor necrosis factor-alpha (TNF alpha), Vascular Endothelial Growth Factor (VEGEF), Urokinase and many others.

One class of proteins that can be made using the compositions and methods for in vivo incorporation of an unnatural amino acid, e.g., an unnatural amino acid comprising a moiety where a saccharide moiety can be attached, or an unnatural amino acid that includes a saccharide moiety described herein, includes transcriptional modulators or a portion thereof. Example transcriptional modulators include genes and transcriptional modulator proteins that modulate cell growth, differentiation, regulation, or the like. Transcriptional modulators are found in prokaryotes, viruses, and eukaryotes, including fungi, plants, yeasts, insects, and animals, including mammals, providing a wide range of therapeutic targets. It will be appreciated that expression and transcriptional activators regulate transcription by many mechanisms, e.g., by binding to receptors, stimulating a signal transduction cascade, regulating expression of transcription factors, binding to promoters and enhancers, binding to proteins that bind to promoters and enhancers, unwinding DNA, splicing pre-mRNA, polyadenylating RNA, and degrading RNA.

One class of proteins of the invention (e.g., proteins with one or more unnatural amino acid that comprises an amino acid, where a saccharide moiety is linked, and/or an unnatural amino acid that includes a saccharide moiety) include expression activators such as cytokines, inflammatory molecules, growth factors, their receptors, and oncogene products, e.g., interleukins (e.g., IL-1, IL-2, IL-8, etc.), interferons, FGF, IGF-I, IGF-II, FGF, PDGF, TNF, TGF-α, TGF-β, EGF, KGF, SCF/c-Kit, CD40L/CD40, VLA-4/VCAM-1, ICAM-1/LFA-1, and hyalurin/CD44; signal transduction molecules and corresponding oncogene products, e.g., Mos, Ras, Raf, and Met; and transcriptional activators and suppressors, e.g., p53, Tat, Fos, Myc, Jun, Myb, Rel, and steroid hormone receptors such as those for estrogen, progesterone, testosterone, aldosterone, the LDL receptor ligand and corticosterone.

Enzymes (e.g., industrial enzymes) or portions thereof with at least one unnatural amino acid, e.g., an unnatural amino acid comprising a moiety where a saccharide moiety is attached, or an unnatural amino acid that includes a saccharide moiety, are also provided by the invention. Examples of enzymes include, but are not limited to, e.g., amidases, amino acid racemases, acylases, dehalogenases, dioxygenases, diarylpropane peroxidases, epimerases, epoxide hydrolases, esterases, isomerases, kinases, glucose isomerases, glycosidases, glycosyl transferases, haloperoxidases, monooxygenases (e.g., p450s), lipases, lignin peroxidases, nitrile hydratases, nitrilases, proteases, phosphatases, subtilisins, transaminase, and nucleases.

Many proteins that can be modified according to the invention are commercially available (see, e.g., the Sigma BioSciences 2002 catalogue and price list), and the corresponding protein sequences and genes and, typically, many variants thereof, are well-known (see, e.g., Genbank). Any of them can be modified by the insertion of one or more unnatural amino acid that comprises an amino acid, where a saccharide moiety is linked, or that includes an unnatural amino acid that includes a saccharide moiety according to the invention, e.g., to alter the protein with respect to one or more therapeutic, diagnostic or enzymatic properties of interest. Examples of therapeutically relevant properties include serum half-life, shelf half-life, stability, immunogenicity, therapeutic activity, detectability (e.g., by the inclusion of reporter groups (e.g., labels or label binding sites) in the unnatural amino acids, specificity, reduction of $LD_{50}$ or other side effects, ability to enter the body through the gastric tract (e.g., oral availability), or the like. Examples of relevant diagnostic properties include shelf half-life, stability, diagnostic activity, detectability, specificity, or the like. Examples of relevant enzymatic properties include shelf half-life, stability, specificity, enzymatic activity, production capability, or the like.

A variety of other proteins can also be modified to include one or more unnatural amino acids of the invention. For example, the invention can include substituting one or more natural amino acids in one or more vaccine proteins with an unnatural amino acid that comprises an amino acid, where a saccharide moiety is linked, or by incorporating an unnatural amino acid that includes a saccharide moiety, e.g., in proteins from infectious fungi, e.g., *Aspergillus, Candida* species; bacteria, particularly *E. coli*, which serves a model for pathogenic bacteria, as well as medically important bacteria such as Staphylococci (e.g., *aureus*), or Streptococci (e.g., *pneumoniae*); protozoa such as sporozoa (e.g., *Plasmodia*), rhizopods (e.g., *Entamoeba*) and flagellates (*Trypanosoma, Leishmania, Trichomonas, Giardia*, etc.); viruses such as (+) RNA viruses (examples include Poxviruses e.g., vaccinia; Picornaviruses, e.g. polio; Togaviruses, e.g., rubella; Flaviviruses, e.g., HCV; and Coronaviruses), (−) RNA viruses (e.g., Rhabdoviruses, e.g., VSV; Paramyxovimses, e.g., RSV; Orthomyxovimses, e.g., influenza; Bunyaviruses; and Arenaviruses), dsDNA viruses (Reoviruses, for example), RNA to DNA viruses, i.e., Retroviruses, e.g., HIV and HTLV, and certain DNA to RNA viruses such as Hepatitis B.

Agriculturally related proteins such as insect resistance proteins (e.g., the Cry proteins), starch and lipid production enzymes, plant and insect toxins, toxin-resistance proteins, Mycotoxin detoxification proteins, plant growth enzymes (e.g., Ribulose 1,5-Bisphosphate Carboxylase/Oxygenase, "RUBISCO"), lipoxygenase (LOX), and Phosphoenolpyruvate (PEP) carboxylase are also suitable targets for modification by incorporation of unnatural amino acids and/or saccharide additions of invention.

In certain embodiments, the protein or polypeptide of interest (or portion thereof) in the methods and/or compositions of the invention is encoded by a nucleic acid. Typically, the nucleic acid comprises at least one selector codon, at least two selector codons, at least three selector codons, at least four selector codons, at least five selector codons, at least six selector codons, at least seven selector codons, at least eight selector codons, at least nine selector codons, ten or more selector codons.

Defining Polypeptides by Immunoreactivity

Because the glycopolypeptides of the invention provide a variety of new polypeptide sequences (e.g., comprising an unnatural amino acid that comprises an amino acid, where a saccharide moiety can be linked, or an unnatural amino acid that includes a saccharide moiety in the case of proteins synthesized in the translation systems herein, or, e.g., in the case of the novel synthetases, novel sequences of standard amino acids), the glycopolypeptides also provide new structural features which can be recognized, e.g., in immunological assays. The generation of antisera, which specifically bind the polypeptides of the invention, as well as the polypeptides which are bound by such antisera, are a feature of the invention. The term "antibody," as used herein, includes, but is not limited to a polypeptide substantially encoded by an immunoglobulin gene or immunoglobulin genes, or fragments thereof which specifically bind and recognize an analyte (antigen). Examples include polyclonal, monoclonal, chimeric, and single chain antibodies, and the like. Fragments of immunoglobulins, including Fab fragments and fragments produced by an expression library, including phage display, are also included in the term "antibody" as used herein. See, e.g., Paul, *Fundamental Immunology*, 4th Ed., 1999, Raven Press, New York, for antibody structure and terminology.

For example, the invention includes synthetase proteins that specifically bind to, or that are specifically immunoreactive with, an antibody or antisera generated against an immunogen comprising a synthetase amino acid sequence selected from one or more of those in the various sequences herein. To eliminate cross-reactivity with other homologues, the antibody or antisera is subtracted with available synthetases, such as the wild-type *Methanococcus jannaschii* (*M. jannaschii*) tyrosyl synthetase (TyrRS), or a known artificial synthetase, such as any of those in WO 2002/085923. Where the wild-type *M. jannaschii* tyrosyl synthetase (TyrRS), or previous sequence, corresponds to a nucleic acid, a polypeptide encoded by the nucleic acid is optionally generated and used for antibody/antisera subtraction purposes.

In one typical format, the immunoassay uses polyclonal antiserum raised against one or more polypeptide comprising one or more of the synthetase sequences herein, or a substantial subsequence thereof (i.e., at least about 30% of the full length sequence provided). The set of potential polypeptide immunogens derived from these sequences are collectively referred to below as "the immunogenic polypeptides." The resulting antisera is optionally selected to have low cross-reactivity against the control synthetase homologues (wild type TyrRs, and/or synthetases in WO 2002/085923) and any such cross-reactivity is removed, e.g., by immunoabsorbtion, with one or more of the control synthetase homologues, prior to use of the polyclonal antiserum in the immunoassay.

In order to produce antisera for use in an immunoassay, one or more of the immunogenic polypeptides is produced and purified as described herein. For example, recombinant protein can be produced in a recombinant cell. An inbred strain of mice (used in this assay because results are more reproducible due to the virtual genetic identity of the mice) is immunized with the immunogenic protein(s) in combination with a standard adjuvant, such as Freund's adjuvant, and a standard mouse immunization protocol (see, e.g., Harlow and Lane (1988) *Antibodies, A Laboratory Manual*, Cold Spring Harbor Publications, New York, for a standard description of antibody generation, immunoassay formats and conditions that can be used to determine specific immunoreactivity. Additional references and discussion of antibodies is also found herein and can be applied here to defining polypeptides by immunoreactivity). Alternatively, one or more synthetic or recombinant polypeptide derived from the sequences disclosed herein is conjugated to a carrier protein and used as an immunogen. Additional details on proteins, antibodies, antisera, etc. can be found in WO 2002/085923, supra.

Polyclonal sera are collected and titered against the immunogenic polypeptide in an immunoassay, for example, a solid phase immunoassay with one or more of the immunogenic proteins immobilized on a solid support. Polyclonal antisera with a titer of $10^6$ or greater are selected, pooled and subtracted with the control synthetase polypeptides to produce subtracted pooled titered polyclonal antisera.

The subtracted pooled titered polyclonal antisera are tested for cross reactivity against the control homologues in a comparative immunoassay. In this comparative assay, discriminatory binding conditions are determined for the subtracted titered polyclonal antisera which result in at least about a 5–10 fold higher signal to noise ratio for binding of the titered polyclonal antisera to the immunogenic synthetase as compared to binding to the control synthetase homologues. That is, the stringency of the binding reaction is adjusted by the addition of non-specific competitors such as albumin or non-fat dry milk, and/or by adjusting salt conditions, temperature, and/or the like. These binding conditions are used in subsequent assays for determining whether a test polypeptide (a polypeptide being compared to the immunogenic polypeptides and/or the control polypeptides) is specifically bound by the pooled subtracted polyclonal antisera. In particular, test polypeptides which show at least a 2–5× higher signal to noise ratio than the control synthetase homologues under discriminatory binding conditions, and at least about a ½ signal to noise ratio as compared to the immunogenic polypeptide(s), shares substantial structural similarity with the immunogenic polypeptide as compared to known synthetases, and is, therefore a polypeptide of the invention.

In another example, immunoassays in the competitive binding format are used for detection of a test polypeptide. For example, as noted, cross-reacting antibodies are removed from the pooled antisera mixture by immunoabsorbtion with the control polypeptides. The immunogenic polypeptide(s) are then immobilized to a solid support which is exposed to the subtracted pooled antisera. Test proteins are added to the assay to compete for binding to the pooled subtracted antisera. The ability of the test protein(s) to compete for binding to the pooled subtracted antisera as compared to the immobilized protein(s) is compared to the ability of the immunogenic polypeptide(s) added to the assay to compete for binding (the immunogenic polypeptides compete effectively with the immobilized immunogenic polypeptides for binding to the pooled antisera). The percent cross-reactivity for the test proteins is calculated, using standard calculations.

In a parallel assay, the ability of the control proteins to compete for binding to the pooled subtracted antisera is optionally determined as compared to the ability of the immunogenic polypeptide(s) to compete for binding to the antisera. Again, the percent cross-reactivity for the control polypeptides is calculated, using standard calculations. Where the percent cross-reactivity is at least 5–10× as high for the test polypeptides as compared to the control polypeptides and or where the binding of the test polypeptides is approximately in the range of the binding of the immunogenic polypeptides, the test polypeptides are said to specifically bind the pooled subtracted antisera.

In general, the immunoabsorbed and pooled antisera can be used in a competitive binding immunoassay as described herein to compare any test polypeptide to the immunogenic and/or control polypeptide(s). In order to make this comparison, the immunogenic, test and control polypeptides are each assayed at a wide range of concentrations and the amount of each polypeptide required to inhibit 50% of the binding of the subtracted antisera to, e.g., an immobilized control, test or immunogenic protein is determined using standard techniques. If the amount of the test polypeptide required for binding in the competitive assay is less than twice the amount of the immunogenic polypeptide that is required, then the test polypeptide is said to specifically bind to an antibody generated to the immunogenic protein, provided the amount is at least about 5–10× as high as for the control polypeptide.

As an additional determination of specificity, the pooled antisera is optionally fully immunosorbed with the immunogenic polypeptide(s) (rather than the control polypeptides) until little or no binding of the resulting immunogenic polypeptide subtracted pooled antisera to the immunogenic polypeptide(s) used in the immunosorbtion is detectable. This fully immunosorbed antisera is then tested for reactivity with the test polypeptide. If little or no reactivity is observed (i.e., no more than 2× the signal to noise ratio observed for binding of the fully immunosorbed antisera to the immunogenic polypeptide), then the test polypeptide is specifically bound by the antisera elicited by the immunogenic protein.

Orthogonal tRNA and Orthogonal Aminoacyl-tRNA Synthetase Pairs

Translation systems that are suitable for making proteins that include one or more unnatural amino acids are described in International patent applications WO 2002/086075, entitled "METHODS AND COMPOSITION FOR THE PRODUCTION OF ORTHOGONAL tRNA- AMINOACYLtRNA SYNTHETASE PAIRS" and WO 2002/085923, supra. Each of these applications is incorporated herein by reference in its entirety. Such translation systems generally comprise cells that include an orthogonal tRNA (O-tRNA), an orthogonal aminoacyl tRNA synthetase (O-RS), and an unnatural amino acid (for example, an unnatural amino acid comprising a moiety where a saccharide moiety can be attached, such as an aldehyde- or keto-derivatized amino acid, or an unnatural amino acid that includes a saccharide moiety), where the O-RS aminoacylates the O-tRNA with the unnatural amino acid. The cell uses the components to incorporate the unnatural amino acid into a growing polypeptide chain.

An orthogonal pair is composed of an O-tRNA, e.g., a suppressor tRNA, a frameshift tRNA, or the like, and an O-RS. The O-tRNA is not acylated by endogenous synthetases and is capable of decoding a selector codon, as described above. The O-RS recognizes the O-tRNA, e.g., with an extended anticodon loop, and preferentially aminoacylates the O-tRNA with an unnatural amino acid, e.g., an unnatural amino acid comprising a moiety where a saccharide moiety can be attached, or an unnatural amino acid that includes a saccharide moiety. The development of multiple orthogonal tRNA/synthetase pairs can allow the simultaneous incorporation of multiple unnatural amino acids using different codons. See Example 5 for exemplary O-tRNA and O-RS sequences.

The O-tRNA and the O-RS can be naturally occurring or can be derived by mutation of a naturally occurring tRNA and/or RS from a variety of organisms, which are described under sources and hosts. In various embodiments, the O-tRNA and O-RS are derived from at least one organism. In another embodiment, the O-tRNA is derived from a naturally occurring or mutated naturally occurring tRNA from a first organism and the O-RS is derived from naturally occurring or mutated naturally occurring RS from a second organism.

Specifically, these methods include: (a) generating a library of tRNAs derived from at least one tRNA from a first organism; (b) negatively selecting the library for tRNAs that are aminoacylated by an aminoacyl-tRNA synthetase (RS) from a second organism in the absence of a RS from the first organism, thereby providing a pool of tRNAs; (c) selecting the pool of tRNAs for members that are aminoacylated by an introduced orthogonal RS (O-RS), thereby providing at least one recombinant O-tRNA. The recombinant O-tRNA recognizes a selector codon and is not efficiency recognized by the RS from the second organism and is preferentially aminoacylated by the O-RS. The method also includes: (d) generating a library of mutant RSs derived from at least one aminoacyl-tRNA synthetase (RS) from a third organism; (e) selecting the library of RSs for members that preferentially aminoacylate the recombinant O-tRNA in the presence of an unnatural amino acid and a natural amino acid, thereby providing a pool of active RSs; and, (f) negatively selecting the pool for active RSs that preferentially aminoacylate the at least one recombinant O-tRNA in the absence of the unnatural amino acid, thereby providing the specific O-tRNA/O-RS pair, where the specific O-tRNA/O-RS pair comprises at least one recombinant O-RS that is specific for the unnatural amino acid, e.g., an unnatural amino acid comprising a moiety where a saccharide moiety can be attached, or an unnatural amino acid that includes a saccharide moiety, and the recombinant O-tRNA.

One strategy for generating an orthogonal pair involves generating mutant libraries from which to screen and/or select an O-tRNA or O-RS.

A second strategy for generating an orthogonal tRNA/synthetase pair involves importing a heterologous tRNA/synthetase pair, e.g., importing a pair from another, e.g., source organism into the host cell. The properties of the heterologous synthetase candidate include, e.g., that it does not charge any host cell tRNA, and the properties of the heterologous tRNA candidate include, e.g., that it is not acylated by any host cell synthetase. In addition, the heterologous tRNA derived from the heterologous tRNA is orthogonal to all host cell synthetases.

Orthogonal Aminoacyl tRNA Synthetases (O-RS)

An O-RS of the invention preferentially aminoacylates an O-tRNA with a an unnatural amino acid, e.g., an unnatural amino acid comprising a moiety where a saccharide moiety can be attached, or an unnatural amino acid that includes a saccharide moiety, in vitro or in vivo. An O-RS of the invention can be provided to the translation system, e.g., a cell, or an in vivo translation system by a polypeptide that includes an O-RS and/or by a polynucleotide that encodes an O-RS or a portion thereof. For example, an O-RS comprises an amino acid sequence as set forth in SEQ ID NO.: 1–6, or a conservative variation thereof. In another example, an O-RS, or a portion thereof, is encoded by a polynucleotide sequence that encodes an amino acid comprising SEQ ID NO.: 1–6, or a complementary polynucleotide sequence thereof, or is encoded by a polynucleotide comprising a polynucleotide sequence of any one of SEQ ID NO.: 8, 9, or 10. See, e.g., Table 2 and Example 5 herein for sequences of exemplary O-RS molecules. See also the section entitled "Nucleic Acid and Polypeptide Sequence and Variants" herein.

Methods for producing an O-RS are based on generating a pool of mutant synthetases from the framework of a wild-type synthetase, and then selecting for mutated RSs based on their specificity for an unnatural amino acid having, e.g., an aldehyde- or keto-moiety or a saccharide moiety relative to the common twenty amino acids. To isolate such a synthetase, the selection methods of the invention are: (i) sensitive, as the activity of desired synthetases from the initial rounds can be low and the population small; (ii) "tunable", since it is desirable to vary the selection stringency at different selection rounds; and, (iii) general, so that it can be used for different unnatural amino acids.

Methods to generate an orthogonal aminoacyl tRNA synthetase include mutating the synthetase, e.g., at the active site in the synthetase, at the editing mechanism site in the synthetase, at different sites by combining different domains of synthetases, or the like, and applying a selection process. A strategy is used, which is based on the combination of a positive selection followed by a negative selection. In the positive selection, suppression of the selector codon introduced at a nonessential position(s) of a positive marker allows cells to survive under positive selection pressure. In the presence of both natural and unnatural amino acids, survivors thus encode active synthetases charging the orthogonal suppressor tRNA with either a natural or unnatural amino acid. In the negative selection in the absence of the unnatural amino acid, suppression of a selector codon introduced at a nonessential position(s) of a negative marker removes synthetases with natural amino acid specificities. Survivors of the negative and positive selection encode synthetases that aminoacylate (charge) the orthogonal suppressor tRNA with unnatural amino acids only. These synthetases can then be subjected to further mutagenesis, e.g., DNA shuffling, other recursive mutagenesis methods, and/or the like.

The library of mutant RSs can be generated using various mutagenesis techniques known in the art. For example, the mutant RSs can be generated by site-specific mutations, random point mutations, homologous recombination, chimeric construction or the like. Chimeric libraries of RSs are also included in the invention.

The positive selection can be based on suppression of a selector codon in a positive selection marker comprising a selector codon, e.g., an amber stop codon, in the selection marker gene. The antibiotic or other selective agent can be applied as the positive selection pressure. In addition, the selection marker can be used as both a positive marker and negative marker, as describe herein, in the presence and absence of unnatural amino acid. Optionally, the selection marker gene comprising a selector codon is used for the positive selection and a negative selection marker, e.g., a toxic marker, such as a barnase gene comprising at least one or more selector codons, is used for the negative selection.

The positive selection can also be based on suppression of a selector codon at a nonessential position in the β-lactamase gene, rendering cells ampicillin resistant; and a negative selection using the ribonuclease barnase as the negative marker is used. In contrast to β-lactamase, which is secreted into the periplasm, a chloramphenicol acetyltransferase (CAT) gene can also be used, which localizes in the cytoplasm; moreover, ampicillin is bactericidal, while chloramphenicol is bacteriostatic.

Once the synthetases are subject to the positive and negative selection/screening strategy, these synthetases can then be subjected to further mutagenesis. For example, a nucleic acid that encodes the O-RS can be isolated; a set of polynucleotides that encode mutated O-RSs (e.g., by random mutagenesis, site-specific mutagenesis, recombination or any combination thereof) can be generated from the nucleic acid; and, these individual steps or a combination of these steps can be repeated until a mutated O-RS is obtained that preferentially aminoacylates the O-tRNA with the unnatural amino acid, e.g., an unnatural amino acid comprising a moiety where a saccharide moiety can be attached, or an unnatural amino acid that includes a saccharide moiety. In one aspect of the invention, the steps are performed multiple times, e.g., at least two times. Optionally, the concentration of the selection agent is varied.

Additional levels of selection/screening stringency can also be used in the methods of the invention, for producing O-tRNA, O-RS, or pairs thereof. The selection or screening stringency can be varied on one or both steps of the method to produce an O-RS. This could include, e.g., varying the amount of selection/screening agent that is used, etc. Additional rounds of positive and/or negative selections can also be performed. Selecting or screening can also comprise one or more of a change in amino acid permeability, a change in translation efficiency, a change in translational fidelity, etc. Typically, the one or more change is based upon a mutation in one or more gene in an organism in which an orthogonal tRNA-tRNA synthetase pair is used to produce protein.

Additional details for producing O-RS, for altering the substrate specificity of the synthetase, and other examples of O-RSs can be found in WO 2002/086075, supra.

Orthogonal tRNA (O-tRNAs)

An orthogonal tRNA (O-tRNA) of the invention mediates incorporation of an unnatural amino acid, e.g., an unnatural amino acid comprising a moiety where a saccharide moiety can be attached, such as an aldehyde- or keto-derivatized amino acid, or an unnatural amino acid that includes a saccharide moiety, into a protein that is encoded by a polynucleotide that comprises a selector codon that is recognized by the O-tRNA, e.g., in vivo or in vitro.

An example of O-tRNAs of the invention is SEQ ID NO.: 7. See Table 2 and Example 5, herein, for sequences of exemplary O-tRNA and O-RS molecules. See also the section entitled "Nucleic Acid and Polypeptide Sequence and Variants" herein. In the tRNA molecule, Thymine (T) is replace with Uracil (U). Additional modifications to the bases can also be present. The invention also includes conservative variations of O-tRNA. For example, conservative variations of O-tRNA include those molecules that function like the O-tRNA of SEQ ID NO.: 7 and maintain the tRNA L-shaped structure, but do not have the same sequence (and are other than wild type tRNA molecules). See also the section herein entitled "Nucleic acids and Polypeptides Sequence and Variants."

Methods for producing a recombinant orthogonal tRNA (O-tRNA) is provided in International patent application WO 2002/086075, supra.

For example, to improve the orthogonality of a tRNA while preserving its affinity toward a desired RS, the methods include a combination of negative and positive selections with a mutant suppressor tRNA library in the absence and presence of the cognate synthetase, respectively. In the negative selection, a selector codon(s) is introduced in a marker gene, e.g., a toxic gene, such as barnase, at a nonessential position. When a member of the mutated tRNA library, e.g., derived from *Methanococcus jannaschii*, is aminoacylated by endogenous host, e.g., *Escherichia coli* synthetases (i.e., it is not orthogonal to the host, e.g., *Escherichia coli* synthetases), the selector codon, e.g., an amber codon, is suppressed and the toxic gene product produced leads to cell death. Cells harboring orthogonal tRNAs or non-functional tRNAs survive. Survivors are then subjected to a positive selection in which a selector codon, e.g., an amber codon, is placed in a positive marker gene, e.g., a drug resistance gene, such a β-lactamase gene. These cells also contain an expression vector with a cognate RS. These cells are grown in the presence of a selection agent, e.g., ampicillin. tRNAs are then selected for their ability to be aminoacylated by the coexpressed cognate synthetase and to insert an amino acid in response to this selector codon. Cells harboring non-functional tRNAs, or tRNAs that cannot be recognized by the synthetase of interest are sensitive to the antibiotic. Therefore, tRNAs that: (i) are not substrates for endogenous host, e.g., *Escherichia coli*, synthetases; (ii) can be aminoacylated by the synthetase of interest; and (iii) are functional in translation survive both selections.

Libraries of mutated tRNA are constructed. Mutations can be introduced at a specific position(s), e.g., at a nonconservative position(s), or at a conservative position, at a randomized position(s), or a combination of both in a desired loop of a tRNA, e.g., an anticodon loop, (D arm, V loop, TψC arm) or a combination of loops or all loops. Chimeric libraries of tRNA are also included in the invention. It should be noted that libraries of tRNA synthetases from various organism (e.g., microorganisms such as eubacteria or archaebacteria) such as libraries that comprise natural diversity (see, e.g., U.S. Pat. No. 6,238,884 to Short et al; U.S. Pat. No. 5,756,316 to Schallenberger et al; U.S. Pat. No. 5,783,431 to Petersen et al; U.S. Pat. No. 5,824,485 to Thompson et al; U.S. Pat. No. 5,958,672 to Short et al), are optionally constructed and screened for orthogonal pairs.

Additional mutations can be introduced at a specific position(s), e.g., at a nonconservative position(s), or at a conservative position, at a randomized position(s), or a combination of both in a desired loop or region of a tRNA, e.g., an anticodon loop, the acceptor stem, D arm or loop, variable loop, TψC arm or loop, other regions of the tRNA molecule, or a combination thereof. Typically, mutations in a tRNA include mutating the anticodon loop of each member of the library of mutant tRNAs to allow recognition of a selector codon. The method can further include adding an additional sequence (CCA) to 3' terminus of the O-tRNA. Typically, an O-tRNA possesses an improvement of orthogonality for a desired organism compared to the starting material, e.g., the plurality of tRNA sequences, while preserving its affinity towards a desired RS.

For example, in the negative selection, a selector codon(s) is introduced into polynucleotide that encodes a negative selection marker, e.g., an enzyme that confers antibiotic resistance, e.g., β-lactamase, an enzyme that confers a detectable product, e.g., β-galactosidase, chloramphenicol acetyltransferase (CAT), e.g., a toxic product, such as barnase, at a nonessential position (e.g., still producing a functional barnase), etc. Screening/selection is optionally done by growing the population of cells in the presence of a selective agent (e.g., an antibiotic, such as ampicillin). In one embodiment, the concentration of the selection agent is varied.

For example, to measure the activity of suppressor tRNAs, a selection system is used that is based on the in vivo suppression of selector codon, e.g., nonsense or frameshift mutations introduced into a polynucleotide that encodes a negative selection marker, e.g., a gene for β-lactamase (bla). For example, polynucleotide variants, e.g., bla variants, with a selector codon at position a certain position, are constructed. Cells, e.g., bacteria, are transformed with these polynucleotides. In the case of an orthogonal tRNA, which cannot be efficiently charged by endogenous E. coli synthetases, antibiotic resistance, e.g., ampicillin resistance, should be about or less than that for a bacteria transformed with no plasmid. If the tRNA is not orthogonal, or if a heterologous synthetase capable of charging the tRNA is co-expressed in the system, a higher level of antibiotic, e.g., ampicillin, resistance is be observed. Cells, e.g., bacteria, are chosen that are unable to grow on LB agar plates with antibiotic concentrations about equal to cells transformed with no plasmids.

In the case of a toxic product (e.g., ribonuclease barnase), when a member of the plurality of potential tRNAs is aminoacylated by endogenous host, e.g., *Escherichia coli* synthetases (i.e., it is not orthogonal to the host, e.g., *Escherichia coli* synthetases), the selector codon is suppressed and the toxic polynucleotide product produced leads to cell death. Cells harboring orthogonal tRNAs or non-functional tRNAs survive. Optionally, the ribonuclease barnase gene can include two or more amber codons. The surviving cells can be selected, e.g., by using a comparison ratio cell density assay.

In one embodiment, the pool of tRNAs that are orthogonal to a desired organism are subjected to a positive selection in which a selector codon is placed in a positive selection marker, e.g., encoded by a drug resistance gene, such a β-lactamase gene. The positive selection is performed on a cell comprising a polynucleotide encoding or comprising a member of the pool of tRNAs that are orthogonal to the cell, a polynucleotide encoding a positive selection marker, and a polynucleotide encoding cognate RS. In certain embodiments, the second population of cells comprises cells that were not eliminated by the negative selection. The polynucleotides are expressed in the cell and the cell is grown in the presence of a selection agent, e.g., ampicillin. tRNAs are then selected for their ability to be aminoacylated by the coexpressed cognate synthetase and to insert an amino acid in response to this selector codon. Typically, these cells show an enhancement in suppression efficiency compared to cells harboring non-functional tRNAs, or tRNAs that cannot efficiently be recognized by the synthetase of interest. The cell harboring the non-functional or tRNAs that are not efficiently recognized by the synthetase of interest are sensitive to the antibiotic. Therefore, tRNAs that: (i) are not substrates for an endogenous host, e.g., *Escherichia coli*, synthetases; (ii) can be aminoacylated by the synthetase of interest; and (iii) are functional in translation survive both selections.

The stringency of the selection, e.g., the positive selection, the negative selection or both the positive and negative selection, in the above described-methods, optionally includes varying the selection stringency. For example, because barnase is an extremely toxic protein, the stringency of the negative selection can be controlled by introducing different numbers of selector codons into the barnase gene and/or by using an inducible promoter. In another example, the concentration of the selection or screening agent is varied (e.g., ampicillin concentration). In one aspect of the invention, the stringency is varied because the desired activity can be low during early rounds of screening. Thus, less stringent selection criteria are applied in early rounds and more stringent criteria are applied in later rounds of selection. In certain embodiments, the negative selection, the positive selection, or both the negative and positive selection, can be repeated multiple times. Multiple different negative selection markers, positive selection markers, or both negative and positive selection markers can be used. In certain embodiments, the positive and negative selection marker can be the same.

Other types of selections can be used in the invention for generating, e.g., O-RS, O-tRNA, and O-tRNA/O-RS pairs that utilize, e.g., an unnatural amino acid comprising a moiety where a saccharide moiety can be attached, such as an aldehyde- or keto-derivatized amino acid, or an unnatural amino acid that includes a saccharide moiety. For example, the positive selection step, the negative selection step or both the positive and negative selection steps can include using a reporter, wherein the reporter is detected by fluorescence-activated cell sorting (FACS). For example, a positive selection can be done first with a positive selection marker, e.g., a chloramphenicol acetyltransferase (CAT) gene, where the CAT gene comprises a selector codon, e.g., an amber stop codon, in the CAT gene, which followed by a negative selection screen, that is based on the inability to suppress a selector codon(s), e.g., two or more codons, at positions within a negative marker, e.g., a T7 RNA polymerase gene, which effects transcription of another gene, e.g., GFP. In one embodiment, the positive selection marker and the negative selection marker can be found on the same vector, e.g., plasmid. Expression of the negative marker drives expression of the reporter, e.g., green fluorescent protein (GFP). The stringency of the selection and screen can be varied, e.g., the intensity of the light need to fluorescence the reporter can be varied. In another embodiment, a positive selection can be done with a reporter as a positive selection marker, which is screened by FACs, followed by a negative selection screen, that is based on the inability to suppress a selector codon(s), e.g., two or more, at positions within a negative marker, e.g., barnase gene. See also, e.g., Example 4, herein.

Optionally, the reporter is displayed on a cell surface, on a phage display or the like. Cell-surface display, e.g., the OmpA-based cell-surface display system, relies on the expression of a particular epitope, e.g., a poliovirus C3 peptide fused to an outer membrane porin OmpA, on the surface of the *Escherichia coli* cell. The epitope is displayed on the cell surface only when a selector codon in the protein message is suppressed during translation. The displayed peptide then contains the amino acid recognized by one of the mutant aminoacyl-tRNA synthetases in the library, and the cell containing the corresponding synthetase gene can be isolated with antibodies raised against peptides containing specific unnatural amino acids. The OmpA-based cell-surface display system was developed and optimized by Georgiou et al. as an alternative to phage display. See Francisco, J. A., Campbell, R., Iverson, B. L. & Georgoiu, G. *Production and fluorescence-activated cell sorting of Escherichia coli expressing a functional antibody fragment on the external surface. Proc Natl Acad Sci USA.* 90:10444–8 (1993).

The selection steps can also be carried out in vitro. The selected component, e.g., synthetase and/or tRNA, can then be introduced into a cell for use in in vivo incorporation of an unnatural amino acid.

Additional methods for producing a recombinant orthogonal tRNA can be found, e.g., in International patent applications WO 2002/086075, supra. See also Forster et al., (2003) *Programming peptidomimetic synthetases by translating genetic codes designed de novo PNAS* 100(11):6353–6357; and, Feng et al., (2003), *Expanding tRNA recognition of a tRNA synthetase by a single amino acid change, PNAS* 100(10): 5676–5681.

Source and Host Organisms

The translational components to produce glycoproteins of the invention are typically derived from non-eukaryotic organisms. For example, the orthogonal O-tRNA can be derived from a non-eukaryotic organism (or a combination of organisms), e.g., an archaebacterium, such as *Methanococcus jannaschii, Methanobacterium thermoautotrophicum, Halobacterium* such as *Haloferax volcanii* and *Halobacterium* species NRC-1, *Archaeoglobus fulgidus, Pyrococcus furiosus, Pyrococcus horikoshii, Aeuropyrum pernix, Methanococcus maripaludis, Methanopyrus kandleri, Methanosarcina mazei* (Mm), *Pyrobaculum aerophilum, Pyrococcus abyssi, Sulfolobus solfataricus* (Ss), *Sulfolobus tokodaii, Thermoplasma acidophilum, Thermoplasma volcanium*, or the like, or a eubacterium, such as *Escherichia coli, Thermus thermophilus, Bacillus stearothermphilus*, or the like, while the orthogonal O-RS can be derived from a non-eukaryotic organism (or a combination of organisms), e.g., an archaebacterium, such as *Methanococcus jannaschii, Methanobacterium thermoautotrophicum, Halobacterium* such as *Haloferax volcanii* and *Halobacterium* species NRC-1, *Archaeoglobus fulgidus, Pyrococcus furiosus, Pyrococcus horikoshii, Aeuropyrum pernix, Methanococcus maripaludis, Methanopyrus kandleri, Methanosarcina mazei, Pyrobaculum aerophilum, Pyrococcus abyssi, Sulfolobus solfataricus, Sulfolobus tokodaii, Thermoplasma acidophilum, Thermoplasma volcanium*, or the like, or a eubacterium, such as *Escherichia coli, Thermus thermophilus, Bacillus stearothermphilus*, or the like. In one embodiment, eukaryotic sources, e.g., plants (e.g., complex plants such as monocots, or dicots), algae, protists, fungi, yeasts, animals (e.g., mammals, insects, arthropods, etc.), or the like, can also be used as sources of O-tRNAs and O-RSs.

The individual components of an O-tRNA/O-RS pair can be derived from the same organism or different organisms. The orthogonal tRNA-RS pair can be used in a variety of host organisms, e.g., a second organism. In one embodiment, the O-tRNA/O-RS pair is from the same organism. Alternatively, the O-tRNA and the O-RS of the O-tRNA/O-RS pair are from different organisms.

Selector Codons

Selector codons of the invention expand the genetic codon framework of protein biosynthetic machinery for the incorporation of an unnatural amino acid, e.g., an unnatural amino acid comprising a moiety where a saccharide moiety can be attached, or an unnatural amino acid that includes a saccharide moiety. For example, a selector codon includes, e.g., a unique three base codon, a nonsense codon, such as a stop codon, e.g., an amber codon, or an opal codon, an unnatural codon, at least a four base codon, a rare codon, or the like. A number of selector codons can be introduced into a desired gene, e.g., one or more, two or more, more than three, etc.

The 64 genetic codons code for 20 amino acids and three stop codons. Because only one stop codon is needed for translational termination, the other two can in principle be used to encode nonproteinogenic amino acids. The amber stop codon, UAG, has been successfully used in in vitro biosynthetic system and in *Xenopus oocytes* to direct the incorporation of unnatural amino acids. Among the three stop codons, UAG is the least used stop codon in *Escherichia coli*. Some *Escherichia coli* strains contain natural suppressor tRNAs, which recognize UAG and insert a natural amino acid. In addition, these amber suppressor tRNAs have been used in conventional protein mutagenesis. In certain embodiments of the invention, other stop codons are used in the invention.

In one embodiment, the methods involve the use of a selector codon that is a stop codon for the incorporation of unnatural amino acids in vivo. For example, an O-tRNA is generated that recognizes the stop codon, e.g., UAG, and is aminoacylated by an O-RS with a desired unnatural amino acid. This O-tRNA is not recognized by the naturally occurring aminoacyl-tRNA synthetases. Conventional site-directed mutagenesis can be used to introduce the stop codon, e.g., TAG, at the site of interest in the protein gene. See, e.g., Sayers, J. R., Schmidt, W. Eckstein, F. *5',3' Exonuclease in phosphorothioate-based oligonucleotide-directed mutagenesis. Nucleic Acids Res,* 791–802 (1988). When the O-RS, O-tRNA and the mutant gene are combined in vivo, the unnatural amino acid is incorporated in response to the UAG codon to give a protein containing the unnatural amino acid at the specified position.

The incorporation of unnatural amino acids in vivo can be done without significant perturbation of the host, e.g., *Escherichia coli*. For example, in non-eukaryotic cells, such as *Escherichia coli*, because the suppression efficiency for the UAG codon depends upon the competition between the O-tRNA, e.g., the amber suppressor tRNA, and the release factor 1 (RF1) (which binds to the UAG codon and initiates release of the growing peptide from the ribosome), the suppression efficiency can be modulated by, e.g., either increasing the expression level of O-tRNA, e.g., the suppressor tRNA, or using an RF1 deficient strain.

Unnatural amino acids, e.g., unnatural amino acids comprising a moiety where a saccharide moiety can be attached, such as an aldehyde- or keto-derivatized amino acids or unnatural amino acids that includes a saccharide moiety, can also be encoded with rare codons. For example, when the arginine concentration in an in vitro protein synthesis reaction is reduced, the rare arginine codon, AGG, has proven to be efficient for insertion of Ala by a synthetic tRNA acylated with alanine. See, e.g., Ma et al., *Biochemistry*, 32:7939 (1993). In this case, the synthetic tRNA competes with the naturally occurring tRNAArg, which exists as a minor species in *Escherichia coli*. Some organisms do not use all triplet codons. An unassigned codon AGA in *Micrococcus*

*luteus* has been utilized for insertion of amino acids in an in vitro transcription/translation extract. See, e.g., Kowal and Oliver, *Nucl. Acid. Res.*, 25:4685 (1997). Components of the invention can be generated to use these rare codons in vivo.

Selector codons also comprise four or more base codons, such as, four, five, six or more base codons. Examples of four base codons include, e.g., AGGA, CUAG, UAGA, CCCU and the like. Examples of five base codons include, e.g., AGGAC, CCCCU, CCCUC, CUAGA, CUACU, UAGGC and the like. For example, in the presence of mutated O-tRNAs, e.g., a special frameshift suppressor tRNAs, with anticodon loops, e.g., with at least 8–10 nt anticodon loops, the four or more base codon is read as single amino acid. In other embodiments, the anticodon loops can decode, e.g., at least a four-base codon, at least a five-base codon, or at least a six-base codon or more. Since there are 256 possible four-base codons, multiple unnatural amino acids can be encoded in the same cell using the four or more base codon. See Anderson et al., *Exploring the Limits of Codon and Anticodon Size, Chemistry and Biology*, Vol. 9, 237–244 (2002); and, Magliery, *Expanding the Genetic Code: Selection of Efficient Suppressors of Four-base Codons and Identification of "Shifty" Four-base Codons with a Library Approach in Escherichia coli, J. Mol. Biol.* 307: 755–769 (2001).

Methods of the invention include using extended codons based on frameshift suppression. Four or more base codons can insert, e.g., one or multiple unnatural amino acids into the same protein. For example, four-base codons have been used to incorporate unnatural amino acids into proteins using in vitro biosynthetic methods. See, e.g., Ma et al., *Biochemistry*, 1993, 32, 7939 (1993); and Hohsaka et al., *J. Am. Chem. Soc.*, 121:34 (1999). CGGG and AGGU were used to simultaneously incorporate 2-naphthylalanine and an NBD derivative of lysine into streptavidin in vitro with two chemically acylated frameshift suppressor tRNAs. See, e.g., Hohsaka et al., *J. Am. Chem. Soc.*, 121:12194 (1999). In an in vivo study, Moore et al. examined the ability of tRNA$^{Leu}$ derivatives with NCUA anticodons to suppress UAGN codons (N can be U, A, G, or C), and found that the quadruplet UAGA can be decoded by a tRNA$^{Leu}$ with a UCUA anticodon with an efficiency of 13 to 26% with little decoding in the 0 or –1 frame. See Moore et al., *J. Mol. Biol.*, 298:195 (2000). In one embodiment, extended codons based on rare codons or nonsense codons can be used in invention, which can reduce missense readthrough and frameshift suppression at other unwanted sites.

A translational bypassing system can also be used to incorporate an unnatural amino acid, e.g., an unnatural amino acid comprising a moiety where a saccharide moiety can be attached, or an unnatural amino acid that includes a saccharide moiety, in a desired polypeptide. In a translational bypassing system, a large sequence is inserted into a gene but is not translated into protein. The sequence contains a structure that serves as a cue to induce the ribosome to hop over the sequence and resume translation downstream of the insertion.

Alternatively, or in combination with others methods described above to incorporate an unnatural amino acid, e.g., an unnatural amino acid comprising a moiety where a saccharide moiety can be attached, or an unnatural amino acid that includes a saccharide moiety, in a polypeptide, a trans-translation system can be used. This system involves a molecule called tmRNA present in *Escherichia coli*. This RNA molecule is structurally related to an alanyl tRNA and is aminoacylated by the alanyl synthetase. The difference between tmRNA and tRNA is that the anticodon loop is replaced with a special large sequence. This sequence allows the ribosome to resume translation on sequences that have stalled using an open reading frame encoded within the tmRNA as template. In the invention, an orthogonal tmRNA can be generated that is preferentially aminoacylated with an orthogonal synthetase and loaded with an unnatural amino acid. By transcribing a gene using the system, the ribosome stalls at a specific site; the unnatural amino acid is introduced at that site, then translation resumes, using the sequence encoded within the orthogonal tmRNA.

For a given system, a selector codon can also include one of the natural three base codons, where the endogenous system does not use (or rarely uses) the natural base codon. For example, this includes a system that is lacking a tRNA that recognizes the natural three base codon, and/or a system where the three base codon is a rare codon.

Selector codons optionally include unnatural base pairs. These unnatural base pairs further expand the existing genetic alphabet. One extra base pair increases the number of triplet codons from 64 to 125. Properties of third base pairs include stable and selective base pairing, efficient enzymatic incorporation into DNA with high fidelity by a polymerase, and the efficient continued primer extension after synthesis of the nascent unnatural base pair. Descriptions of unnatural base pairs which can be adapted for methods and compositions include, e.g., Hirao, et al., *An unnatural base pair for incorporating amino acid analogues into protein, Nature Biotechnology*, 20:177–182 (2002). Other relevant publications are listed below.

For in vivo usage, the unnatural nucleoside is membrane permeable and is phosphorylated to form the corresponding triphosphate. In addition, the increased genetic information is stable and not destroyed by cellular enzymes. Previous efforts by Benner and others took advantage of hydrogen bonding patterns that are different from those in canonical Watson-Crick pairs, the most noteworthy example of which is the iso-C:iso-G pair. See, e.g., Switzer et al., *J. Am. Chem. Soc.*, 111:8322 (1989); and Piccirilli et al., *Nature*, 1990, 343:33 (1990); Kool, *Curr. Opin. Chem. Biol.*, 4:602 (2000). These bases in general mispair to some degree with natural bases and cannot be enzymatically replicated. Kool and co-workers demonstrated that hydrophobic packing interactions between bases can replace hydrogen bonding to drive the formation of base pair. See Kool, *Curr. Opin. Chem. Biol.*, 4:602 (2000); and Guckian and Kool, *Angew. Chem. Int. Ed. Engl.*, 36, 2825 (1998). In an effort to develop an unnatural base pair satisfying all the above requirements, Schultz, Romesberg and co-workers have systematically synthesized and studied a series of unnatural hydrophobic bases. A PICS:PICS self-pair is found to be more stable than natural base pairs, and can be efficiently incorporated into DNA by Klenow fragment of *Escherichia coli* DNA polymerase I (KF). See, e.g., McMinn et al., *J. Am. Chem. Soc.*, 121:11586 (1999); and Ogawa et al., *J. Am. Chem. Soc.*, 122:3274 (2000). A 3MN:3MN self-pair can be synthesized by KF with efficiency and selectivity sufficient for biological function. See, e.g., Ogawa et al., *J. Am. Chem. Soc.*, 122:8803 (2000). However, both bases act as a chain terminator for further replication. A mutant DNA polymerase has been recently evolved that can be used to replicate the PICS self pair. In addition, a 7AI self pair can be replicated. See, e.g., Tae et al., *J. Am. Chem. Soc.*, 123:7439 (2001). A novel metallobase pair, Dipic:Py, has also been developed, which forms a stable pair upon binding Cu(II). See Meggers et al., *J. Am. Chem. Soc.*, 122:10714 (2000). Because extended codons and unnatural codons are intrinsically orthogonal to natural codons, the methods of the invention can take advantage of this property to generate orthogonal tRNAs for them.

Unnatural Amino Acids

As used herein an unnatural amino acid refers to any amino acid, modified amino acid, or amino acid analogue other than selenocysteine and/or pyrrolysine and the following twenty genetically encoded alpha-amino acids: alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, valine. The generic structure of an alpha-amino acid is illustrated by Formula I:

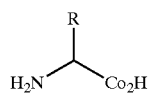

I

An unnatural amino acid is typically any structure having Formula I wherein the R group is any substituent other than one used in the twenty natural amino acids. See, e.g., *Biochemistry* by L. Stryer, 3$^{rd}$ ed. 1988, Freeman and Company, New York, for structures of the twenty natural amino acids. Note that, the unnatural amino acids of the invention can be naturally occurring compounds other than the twenty alpha-amino acids above.

Because the unnatural amino acids of the invention optionally differ from the natural amino acids in side chain only, the unnatural amino acids can typically form amide bonds with other amino acids, e.g., natural or unnatural, in the same manner in which they are formed in naturally occurring proteins. However, the unnatural amino acids have side chain groups that distinguish them from the natural amino acids.

Of particular interest for making glycoproteins of the invention are unnatural amino acids in which R in Formula I includes a moiety that can react with a reactive group that is attached to a saccharide moiety to link the saccharide moiety to a protein that includes the unnatural amino acid. Suitable R groups include, for example, keto-, azido-, hydroxyl-, hydrazine, cyano-, halo-, aminooxy-, alkenyl, alkynyl, carbonyl, ether, thiol, seleno-, sulfonyl-, borate, boronate, phospho, phosphono, phosphine, heterocyclic, enone, imine, aldehyde, ester, thioacid, thioester, hindered ester, hydroxylamine, amine, and the like, or any combination thereof. In some embodiments, the unnatural amino acids have a photoactivatable cross-linker.

In addition to unnatural amino acids that contain novel side chains, unnatural amino acids also optionally comprise modified backbone structures, e.g., as illustrated by the structures of Formula II and III:

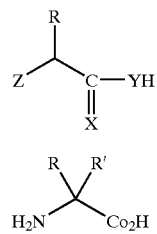

II

III wherein Z typically comprises OH, NH$_2$, SH, NH—R', or S—R'; X and Y, which can be the same or different, typically comprise S or O, and R and R', which are optionally the same or different, are typically selected from the same list of constituents for the R group described above for the unnatural amino acids having Formula I as well as hydrogen. For example, unnatural amino acids of the invention optionally comprise substitutions in the amino or carboxyl group as illustrated by Formulas II and III. Unnatural amino acids of this type include, but are not limited to, α-hydroxy acids, α-thioacids α-aminothiocarboxylates, e.g., with side chains corresponding to the common twenty natural amino acids or unnatural side chains. In addition, substitutions at the α-carbon optionally include L, D, or α-α-disubstituted amino acids such as D-glutamate, D-alanine, D-methyl-O-tyrosine, aminobutyric acid, and the like. Other structural alternatives include cyclic amino acids, such as proline analogues as well as 3,4,6,7,8, and 9 membered ring proline analogues, β and γ amino acids such as substituted β-alanine and γ-amino butyric acid.

For example, many unnatural amino acids are based on natural amino acids, such as tyrosine, glutamine, phenylalanine, and the like. Tyrosine analogs include para-substituted tyrosines, ortho-substituted tyrosines, and meta substituted tyrosines, wherein the substituted tyrosine comprises an acetyl group, a benzoyl group, an amino group, a hydrazine, an hydroxyamine, a thiol group, a carboxy group, an isopropyl group, a methyl group, a $C_6$–$C_{20}$ straight chain or branched hydrocarbon, a saturated or unsaturated hydrocarbon, an O-methyl group, a polyether group, a nitro group, or the like. In addition, multiply substituted aryl rings are also contemplated. Glutamine analogs of the invention include, but are not limited to, α-hydroxy derivatives, γ-substituted derivatives, cyclic derivatives, and amide substituted glutamine derivatives. Example phenylalanine analogs include, but are not limited to, meta-substituted, ortho-substituted, and/or para-substituted phenylalanines, wherein the substituent comprises a hydroxy group, a methoxy group, a methyl group, an allyl group, an aldehyde or keto group, or the like.

Specific examples of unnatural amino acids include, but are not limited to, p-acetyl-L-phenylalanine, O-methyl-L-tyrosine, an L-3-(2-naphthyl)alanine, a 3-methyl-phenylalanine, an O-4-allyl-L-tyrosine, a 4-propyl-L-tyrosine, a tri-O-acetyl-GlcNAcβ-serine, β-O-GlcNAc-L-serine, a tri-O-acetyl-GalNAc-α-threonine, an α-GalNAc-L-threonine, an L-Dopa, a fluorinated phenylalanine, an isopropyl-L-phenylalanine, a p-azido-L-phenylalanine, a p-acyl-L-phenylalanine, a p-benzoyl-L-phenylalanine, an L-phosphoserine, a phosphonoserine, a phosphonotyrosine, a p-iodo-phenylalanine, a p-bromophenylalanine, a p-amino-L-phenylalanine, an isopropyl-L-phenylalanine, those listed below, or elsewhere herein, and the like. The structures of a variety of unnatural amino acids are provided in, for example, FIGS. 17, 18, 19, 26, and 29 of WO 2002/085923.

Unnatural amino acids suitable for use in the methods of the invention also include those that have a saccharide moiety attached to the amino acid side chain. In one embodiment, an unnatural amino acid with a saccharide moiety includes a serine or threonine amino acid with a Man, GalNAc, Glc, Fuc, or Gal moiety. Examples of unnatural amino acids that include a saccharide moiety include, but are not limited to, e.g., a tri-O-acetyl-GlcNAcβ-serine, a β-O-GlcNAc-L-serine, a tri-O-acetyl-GalNAc-α-threonine, an α-GalNAc-L-serine, an O-Man-L-serine, a tetra-acetyl-O-Man-L-serine, an O-GalNAc-L-serine, a tri-acetyl-O-GalNAc-L-serine, a Glc-L-serine, a tetraacetyl-Glc-L-serine, a fuc-L-serine, a tri-acetyl-fuc-L-serine, an O-Gal-L-serine, a tetra-acetyl-O-Gal-L-serine, a beta-O-GlcNAc-L-threonine, a tri-acetyl-beta-GlcNAc-L-threonine, an O-Man-L-threonine, a tetra-acetyl-O-Man-L-threonine, an O-GalNAc-L-threonine, a tri-acetyl-O-GalNAc-L-threonine, a Glc-L-threonine, a tetraacetyl-Glc-L-threonine, a fuc-L-threonine, a tri-acetyl-fuc-L-threonine, an O-Gal-L-threonine, a tetra-acetyl-O-Gal-L-serine, and the like. The invention includes unprotected and acetylated forms of the above. See also WO 2003/031464A2, entitled "Remodeling and Glycoconjugation of Peptides"; and, U.S. Pat. No. 6,331,418, entitled "Saccharide Compositions, Methods and Apparatus for their synthesis."

Chemical Synthesis of Unnatural Amino Acids

Many of the unnatural amino acids provided above are commercially available, e.g., from Sigma (USA) or Aldrich (Milwaukee, Wis., USA). Those that are not commercially available are optionally synthesized as provided in the examples below or using standard methods known to those of skill in the art. For organic synthesis techniques, see, e.g., *Organic Chemistry* by Fessendon and Fessendon, (1982, Second Edition, Willard Grant Press, Boston Mass.); *Advanced Organic Chemistry* by March (Third Edition, 1985, Wiley and Sons, New York); and *Advanced Organic Chemistry* by Carey and Sundberg (Third Edition, Parts A and B, 1990, Plenum Press, New York). See also WO 2002/085923 for additional synthesis of unnatural amino acids.

For example, meta-substituted phenylalanines are synthesized in a procedure as outlined in WO 2002/085923 (see, e.g., FIG. 14 of the publication). Typically, NBS (N-bromosuccinimide) is added to a meta-substituted methylbenzene compound to give a meta-substituted benzyl bromide, which is then reacted with a malonate compound to give the meta substituted phenylalanine. Typical substituents used for the meta position include, but are not limited to, ketones, methoxy groups, alkyls, acetyls, and the like. For example, 3-acetyl-phenylalanine is made by reacting NBS with a solution of 3-methylacetophenone. For more details see the examples below. A similar synthesis is used to produce a 3-methoxy phenylalanine. The R group on the meta position of the benzyl bromide in that case is —$OCH_3$. See, e.g., Matsoukas et al., *J. Med. Chem.*, 1995, 38, 4660–4669.

In some embodiments, the design of unnatural amino acids is biased by known information about the active sites of synthetases, e.g., orthogonal tRNA synthetases used to aminoacylate an orthogonal tRNA. For example, three classes of glutamine analogs are provided, including derivatives substituted at the nitrogen of amide (1), a methyl group at the γ-position (2), and a N-$C^γ$-cyclic derivative (3). Based upon the x-ray crystal structure of *E. coli* GlnRS, in which the key binding site residues are homologous to yeast GlnRS, the analogs were designed to complement an array of side chain mutations of residues within a 10 Å shell of the side chain of glutamine, e.g., a mutation of the active site Phe233 to a small hydrophobic amino acid might be complemented by increased steric bulk at the $C^γ$ position of Gln.

For example, N-phthaloyl-L-glutamic 1,5-anhydride (compound number 4 in FIG. 23 of WO 2002/085923) is optionally used to synthesize glutamine analogs with substituents at the nitrogen of the amide. See, e.g., King, F. E. & Kidd, D. A. A. *A New Synthesis of Glutamine and of γ-Dipeptides of Glutamic Acid from Phthylated Intermediates.* J. Chem. Soc., 3315–3319 (1949); Friedman, O. M. & Chatterrji, R. *Synthesis of Derivatives of Glutamine as Model Substrates for Anti-Tumor Agents.* J. Am. Chem. Soc. 81, 3750–3752 (1959); Craig, J. C. et al. *Absolute Configuration of the Enantiomers of 7-Chloro-4[[4-(diethylamino)-1-methylbutyl]amino]quinoline (Chloroquine). J. Org. Chem.* 53, 1167–1170 (1988); and Azoulay, M., Vilmont, M. & Frappier, F. *Glutamine analogues as Potential Antimalarials,. Eur. J. Med. Chem.* 26, 201–5 (1991). The anhydride is typically prepared from glutamic acid by first protection of the amine as the phthalimide followed by refluxing in acetic acid. The anhydride is then opened with a number of amines, resulting in a range of substituents at the amide. Deprotection of the phthaloyl group with hydrazine affords a free amino acid as shown in FIG. 23 of WO 2002/085923.

Substitution at the γ-position is typically accomplished via alkylation of glutamic acid. See, e.g., Koskinen, A. M. P. & Rapoport, H. Synthesis of 4-Substituted Prolines as Conformationally Constrained Amino Acid Analogues. *J. Org. Chem.* 54, 1859–1866. (1989). A protected amino acid, e.g., as illustrated by compound number 5 in FIG. 24 of WO 2002/085923 is optionally prepared by first alkylation of the amino moiety with 9-bromo-9-phenylfluorene (PhflBr) (see, e.g., Christie, B. D. & Rapoport, H. *Synthesis of Optically Pure Pipecolates from L-Asparagine. Application to the Total Synthesis of (+)-Apovincamine through Amino Acid Decarbonylation and Iminium Ion Cyclization. J. Org. Chem.* 1989, 1859–1866 (1985)) and then esterification of the acid moiety using O-tert-butyl-N,N'-diisopropylisourea. Addition of $KN(Si(CH_3)_3)_2$ regioselectively deprotonates at the α-position of the methyl ester to form the enolate, which is then optionally alkylated with a range of alkyl iodides. Hydrolysis of the t-butyl ester and Phfl group gave the desired γ-methyl glutamine analog (Compound number 2 in FIG. 24 of WO 2002/085923).

An N-$C^γ$ cyclic analog, as illustrated by Compound number 3 in FIG. 25 of WO 2002/085923, is optionally prepared in 4 steps from Boc-Asp-Ot-Bu as previously described. See, e.g., Barton et al., *Synthesis of Novel α-Amino-Acids and Derivatives Using Radical Chemistry: Synthesis of L-and D-α-Amino-Adipic Acids, L-α-aminopimelic Acid and Appropriate Unsaturated Derivatives.* Tetrahedron Lett. 43, 4297–4308 (1987) and Subasinghe et al., *Quisqualic acid analogues: synthesis of beta-heterocyclic 2-aminopropanoic acid derivatives and their activity at a novel quisqualate-sensitized site.* J. Med. Chem. 35 4602–7 (1992). Generation of the anion of the N-t-Boc-pyrrolidinone, pyrrolidinone, or oxazolidone followed by the addition of the compound 7, as shown in FIG. 25, results in a Michael addition product. Deprotection with TFA then results in the free amino acids.

In addition to the above unnatural amino acids, a library of tyrosine analogs has also been designed. Based upon the crystal structure of *B. stearothermophilus* TyrRS, whose active site is highly homologous to that of the *M. jannashii* synthetase, residues within a 10 Å shell of the aromatic side chain of tyrosine were mutated (Y32, G34, L65, Q155, D158, A167, Y32 and D158). The library of tyrosine analogs, as shown in FIG. 26 of WO 2002/085923, has been designed to complement an array of substitutions to these active site amino acids. These include a variety of phenyl substitution patterns, which offer different hydrophobic and hydrogen-bonding properties. Tyrosine analogs are optionally prepared using the general strategy illustrated by WO 2002/085923 (see, e.g., FIG. 27 of the publication). For example, an enolate of diethyl acetamidomalonate is optionally generated using sodium ethoxide. A desired tyrosine analog can then be prepared by adding an appropriate benzyl bromide followed by hydrolysis.

Cellular Uptake of Unnatural Amino Acids

Unnatural amino acid uptake is one issue that is typically considered when designing and selecting unnatural amino acids, e.g., for incorporation into a protein. For example, the high charge density of α-amino acids suggests that these compounds are unlikely to be cell permeable. Natural amino acids are taken up into bacteria via a collection of protein-based transport systems displaying varying degrees of amino acid specificity. The invention therefore provides a rapid screen for assessing which unnatural amino acids, if any, are taken up by cells.

For example, a variety of unnatural amino acids are optionally screened in minimal media for toxicity to cells. Toxicities are typically sorted into five groups: (1) no toxicity, in which no significant change in doubling times occurs; (2) low toxicity, in which doubling times increase by less than about 10%; (3) moderate toxicity, in which doubling times increase by about 10% to about 50%; (4) high toxicity, in which doubling times increase by about 50% to about 100%; and (5) extreme toxicity, in which doubling times increase by more than about 100%. See, e.g., Liu, D. R. & Schultz, P. G. *Progress toward the evolution of an organism with an expanded genetic code. PNAS, USA* 96, 4780–4785 (1999). The toxicity of the amino acids scoring as highly or extremely toxic is typically measured as a function of their concentration to obtain $IC_{50}$ values. In general, amino acids which are very close analogs of natural amino acids or which display reactive functionality demonstrate the highest toxicities. The former trend suggests that mechanisms of toxicity for these unnatural amino acids can be incorporation into proteins or inhibition of essential enzymes that process natural amino acids.

To identify possible uptake pathways for toxic amino acids, toxicity assays are optionally repeated at $IC_{50}$ levels, e.g., in media supplemented with an excess of a structurally similar natural amino acid. For toxic amino acids, the presence of excess natural amino acid typically rescues the ability of the cells to grow in the presence of the toxin, presumably because the natural amino acid effectively outcompetes the toxin for either cellular uptake or for binding to essential enzymes. In these cases, the toxic amino acid is optionally assigned a possible uptake pathway and labeled a "lethal allele" whose complementation is required for cell survival. These lethal alleles are extremely useful for assaying the ability of cells to uptake nontoxic unnatural amino acids. Complementation of the toxic allele, evidenced by the restoration of cell growth, suggests that the nontoxic amino acid is taken up by the cell, possibly by the same uptake pathway as that assigned to the lethal allele. A lack of complementation is inconclusive. For example studies and conclusions see the examples provided below.

Results obtained, e.g., as described in the examples below, demonstrate that complementation of lethal unnatural amino acid alleles is an efficient method for qualitatively assessing amino acid uptake. The method typically requires far less effort than radiolabeling large numbers of compounds and is therefore a more advantageous method for analyzing unnatural; amino acids of interest. This general strategy is optionally used to rapidly evaluate the cellular uptake of a wide range of molecules such as nucleic acid base analogs, carbohydrate analogs, or peptide analogs. For example, this strategy is optionally used to evaluate the cellular uptake of the unnatural amino aids presented herein.

The invention also provides a general method for delivering unnatural amino acids, which is independent of all amino acid uptake pathways. This general method relies on uptake via peptide permeases, which transport dipeptides and tripeptides across the cytoplasmic membrane. Peptide permeases are not very side-chain specific, and the KD values for their substrates are comparable to KD values of amino acid permeases, e.g., about 0.1 mM to about 10 mM). See, e.g., Nickitenko et al., *A structure of DppA, a periplasmic depeptide transport/chemosensory receptor. Biochemistry* 34, 16585–16595 (1995) and Dunten, P., Mowbray, S. L. *Crystal structure of the dipeptide binding protein from Escherichia coli involved in active transport and chemotaxis. Protein Science* 4, 2327–34 (1995). The unnatural amino acids are then taken up as conjugates of natural amino acids, such as lysine, and released into the cytoplasm upon hydrolysis of the dipeptide by one of endogenous *E. coli* peptidases. To test this approach, several Unn-Lys and Lys-Unn dipeptides are synthesized by solid phase synthesis, and the growth of an *E. coli* strain deficient in lysine biosynthesis on lysine minimal media in the presence and absence of these dipeptides is tested. The only source of lysine available to these cells is the dipeptide containing the unnatural amino acid. Uptake of phosphonoserine, phosphonotyrosine, pentafluorophenylalanine, and caged serine have been analyzed in this manner. In all four cases, growth was observed on 10 mM and higher dipeptide concentrations. Although uptake is easily analyzed with the method provided herein, an alternative to designing unnatural amino acid that are amenable to cellular uptake pathways, is to provide biosynthetic pathways to create amino acids in vivo.

Biosynthesis of Unnatural Amino Acids

Many biosynthetic pathways already exist in cells for the production of amino acids and other compounds. While a biosynthetic method for a particular unnatural amino acid may not exist in nature, e.g., in *E. coli*, the invention provide such methods. For example, biosynthetic pathways for unnatural amino acids are optionally generated in *E. coli* by adding new enzymes or modifying existing *E. coli* pathways. Additional new enzymes are optionally naturally occurring enzymes or artificially evolved enzymes. For example, the biosynthesis of p-aminophenylalanine (as presented, e.g., in WO 2002/085923) relies on the addition of a combination of known enzymes from other organisms. The genes for these enzymes can be introduced into a cell, e.g., an *E. coli* cell, by transforming the cell with a plasmid comprising the genes. The genes, when expressed in the cell, provide an enzymatic pathway to synthesize the desired compound. Examples of the types of enzymes that are optionally added are provided in the examples below. Additional enzymes sequences are found, e.g., in Genbank. Artificially evolved enzymes are also optionally added into a cell in the same manner. In this manner, the cellular machinery and resources of a cell are manipulated to produce unnatural amino acids.

A variety of methods are available for producing novel enzymes for use in biosynthetic pathways or for evolution of existing pathways. For example, recursive recombination, e.g., as developed by Maxygen, Inc. (on the world wide web at maxygen(dot)com.), is optionally used to develop novel enzymes and pathways. See, e.g., Stemmer 1994, *"Rapid evolution of a protein in vitro by DNA shuffling," Nature* Vol. 370 No. 4: Pg. 389–391; and Stemmer, 1994, *"DNA shuffling by random fragmentation and reassembly: In vitro recombination for molecular evolution," Proc. Natl. Acad. Sci. USA*. Vol. 91: Pg. 10747–10751. Similarly DesignPath™, developed by Genencor (on the world wide web at genencor(dot)com) is optionally used for metabolic pathway engineering, e.g., to engineer a pathway to create an unnatural amino acid in *E coli*. This technology reconstructs existing pathways in host organisms using a combination of new genes, e.g., identified through functional genomics, and molecular evolution and design. Diversa Corporation (on the world wide web at diversa(dot)com) also provides technology for rapidly screening libraries of genes and gene pathways, e.g., to create new pathways.

Typically, the biosynthesis methods of the invention, e.g., the pathway to create p-aminophenylalanine (pAF) from chorismate, do not affect the concentration of other amino acids produced in the cell. For example a pathway used to produce pAF from chorismate produces pAF in the cell while the concentrations of other aromatic amino acids typically produced from chorismate are not substantially affected. Typically the unnatural amino acid produced with an engineered biosynthetic pathway of the invention is produced in a concentration sufficient for efficient protein biosynthesis, e.g., a natural cellular amount, but not to such a degree as to affect the concentration of the other amino acids or exhaust cellular resources. Typical concentrations produced in vivo in this manner are about 10 mM to about 0.05 mM. Once a bacterium is transformed with a plasmid comprising the genes used to produce enzymes desired for a specific pathway and a twenty-first amino acid, e.g., pAF, dopa, O-methyl-L-tyrosine, or the like, is generated, in vivo selections are optionally used to further optimize the production of the unnatural amino acid for both ribosomal protein synthesis and cell growth.

Nucleic Acid and Polypeptide Sequence and Variants

As described above and below, the invention provides for nucleic acid polynucleotide sequences, e.g., O-tRNAs and O-RSs, and polypeptide amino acid sequences, e.g., O-RSs, and, e.g., compositions and methods comprising said sequences. Examples of said sequences, e.g., O-tRNAs and O-RSs are disclosed herein (see Table 2, e.g., SEQ ID NO. 1–10). However, one of skill in the art will appreciate that the invention is not limited to those sequences disclosed herein, e.g., the Examples. One of skill will appreciate that the invention also provides many unrelated sequences with the functions described herein, e.g., encoding an O-tRNA or an O-RS.

The invention provides polypeptides (e.g., O-RSs) and polynucleotides, e.g., O-tRNA, polynucleotides that encode O-RSs or portions thereof, oligonucleotides used to isolate aminoacyl-tRNA synthetase clones, etc. Polypeptides of the invention include polypeptides or proteins with unnatural amino acids of the invention. An polypeptide of the invention also includes an artificial polypeptide, e.g., (a) a polypeptide that comprises an amino acid sequence as shown in any one of SEQ ID NO.: 4–6; (b) a polypeptide that comprises an amino acid sequence encoded by a polynucleotide sequence as shown in any one of SEQ ID NO.: 8–10; (c) a polypeptide that is specifically immunoreactive with an antibody specific for a polypeptide of (a), or (b); and, (d) an amino acid sequence comprising a conservative variation of (a), (b), or (c). Antibodies and antisera that are specifically immunoreactive with an artificial polypeptide of the invention are also provided. In one embodiment, a composition includes a polypeptide of the invention and an excipient (e.g., buffer, water, pharmaceutically acceptable excipient, etc.).

Polynucleotides of the invention include those that encode proteins or polypeptides of interests of the invention with one or more selector codon. A polynucleotide of the invention also includes a polynucleotide of any one of SEQ ID NOs.: 8, 9, or 10, or a conservative variation thereof. A polynucleotide of the invention includes a polynucleotide that encodes an amino acid sequence comprising SEQ ID NO.:1–6. A polynucleotide of the invention also includes a polynucleotide that encodes a polypeptide of the invention. Similarly, an artificial nucleic acid that hybridizes to a polynucleotide indicated above under highly stringent conditions over substantially the entire length of the nucleic acid (and is other than a naturally polynucleotide) is a polynucleotide of the invention. An artificial polynucleotide is a polynucleotide that is man made and is not naturally occurring.

In certain embodiments, a vector (e.g., a plasmid, a cosmid, a phage, a virus, etc.) comprises a polynucleotide of the invention. In one embodiment, the vector is an expression vector. In another embodiment, the expression vector includes a promoter operably linked to one or more of the polynucleotides of the invention. In another embodiment, a cell comprises a vector that includes a polynucleotide of the invention.

One of skill will also appreciate that many variants of the disclosed sequences are included in the invention. For example, conservative variations of the disclosed sequences that yield a functionally identical sequence are included in the invention. Variants of the nucleic acid polynucleotide sequences, wherein the variants hybridize to at least one disclosed sequence, are considered to be included in the invention. Unique subsequences of the sequences disclosed herein, as determined by, e.g., standard sequence comparison techniques, are also included in the invention.

Conservative Variations

Owing to the degeneracy of the genetic code, "silent substitutions" (i.e., substitutions in a nucleic acid sequence which do not result in an alteration in an encoded polypeptide) are an implied feature of every nucleic acid sequence which encodes an amino acid. Similarly, "conservative amino acid substitutions," in one or a few amino acids in an amino acid sequence are substituted with different amino acids with highly similar properties, are also readily identified as being highly similar to a disclosed construct. Such conservative variations of each disclosed sequence are a feature of the present invention.

"Conservative variations" of a particular nucleic acid sequence refers to those nucleic acids which encode identical or essentially identical amino acid sequences, or, where the nucleic acid does not encode an amino acid sequence, to essentially identical sequences. One of skill will recognize that individual substitutions, deletions or additions which alter, add or delete a single amino acid or a small percentage of amino acids (typically less than 5%, more typically less than 4%, 2% or 1%) in an encoded sequence are "conservatively modified variations" where the alterations result in the deletion of an amino acid, addition of an amino acid, or substitution of an amino acid with a chemically similar amino acid. Thus, "conservative variations" of a listed polypeptide sequence of the present invention include substitutions of a small percentage, typically less than 5%, more typically less than 2% or 1%, of the amino acids of the polypeptide sequence, with a conservatively unnatural amino acid that comprises an amino acid, where a saccharide moiety is linked and/or an unnatural amino acid that includes a saccharide moiety of the same conservative substitution group. Finally, the addition of sequences which do not alter the encoded activity of a nucleic acid molecule, such as the addition of a non-functional sequence, is a conservative variation of the basic nucleic acid.

Conservative substitution tables providing functionally similar amino acids are well known in the art. The following sets forth example groups which contain natural amino acids that include "conservative substitutions" for one another.

Conservative Substitution Groups

| 1 | Alanine (A) | Serine (S) | Threonine (T) | |
|---|---|---|---|---|
| 2 | Aspartic acid (D) | Glutamic acid (E) | | |
| 3 | Asparagine (N) | Glutamine (Q) | | |
| 4 | Arginine (R) | Lysine (K) | | |
| 5 | Isoleucine (I) | Leucine (L) | Methionine (M) | Valine (V) |
| 6 | Phenylalanine (F) | Tyrosine (Y) | Tryptophan (W) | |

Nucleic Acid Hybridization

Comparative hybridization can be used to identify nucleic acids of the invention, such as SEQ ID NO.: 7, 8, 9, or 10, including conservative variations of nucleic acids of the invention, and this comparative hybridization method is a preferred method of distinguishing nucleic acids of the invention. In addition, target nucleic acids which hybridize to a nucleic acid represented by, e.g., SEQ ID NO: 7, 8, 9, or 10, under high, ultra-high and ultra-ultra high stringency conditions are a feature of the invention. Examples of such nucleic acids include those with one or a few silent or conservative nucleic acid substitutions as compared to a given nucleic acid sequence.

A test nucleic acid is said to specifically hybridize to a probe nucleic acid when it hybridizes at least ½ as well to the probe as to the perfectly matched complementary target, i.e., with a signal to noise ratio at lest ½ as high as hybridization of the probe to the target under conditions in which the perfectly matched probe binds to the perfectly matched complementary target with a signal to noise ratio that is at least about 5×–10× as high as that observed for hybridization to any of the unmatched target nucleic acids.

Nucleic acids "hybridize" when they associate, typically in solution. Nucleic acids hybridize due to a variety of well characterized physico-chemical forces, such as hydrogen bonding, solvent exclusion, base stacking and the like. An extensive guide to the hybridization of nucleic acids is found in Tijssen (1993) *Laboratory Techniques in Biochemistry and Molecular Biology—Hybridization with Nucleic Acid Probes* part I chapter 2, "Overview of principles of hybridization and the strategy of nucleic acid probe assays," (Elsevier, New York), as well as in Ausubel, supra. Hames and Higgins (1995) *Gene Probes* 1 IRL Press at Oxford University Press, Oxford, England, (Hames and Higgins 1) and Hames and Higgins (1995) *Gene Probes* 2 IRL Press at Oxford University Press, Oxford, England (Hames and Higgins 2) provide details on the synthesis, labeling, detection and quantification of DNA and RNA, including oligonucleotides.

An example of stringent hybridization conditions for hybridization of complementary nucleic acids which have more than 100 complementary residues on a filter in a Southern or northern blot is 50% formalin with 1 mg of heparin at 42° C., with the hybridization being carried out overnight. An example of stringent wash conditions is a 0.2×SSC wash at 65° C. for 15 minutes (see Sambrook, supra for a description of SSC buffer). Often the high stringency wash is preceded by a low stringency wash to remove background probe signal. An example low stringency wash is 2×SSC at 40° C. for 15 minutes. In general, a signal to noise ratio of 5× (or higher) than that observed for an unrelated probe in the particular hybridization assay indicates detection of a specific hybridization.

"Stringent hybridization wash conditions" in the context of nucleic acid hybridization experiments such as Southern and northern hybridizations are sequence dependent, and are different under different environmental parameters. An extensive guide to the hybridization of nucleic acids is found in Tijssen (1993), supra. and in Hames and Higgins, 1 and 2. Stringent hybridization and wash conditions can easily be determined empirically for any test nucleic acid. For example, in determining stringent hybridization and wash conditions, the hybridization and wash conditions are gradually increased (e.g., by increasing temperature, decreasing salt concentration, increasing detergent concentration and/or increasing the concentration of organic solvents such as formalin in the hybridization or wash), until a selected set of criteria are met. For example, in highly stringent hybridization and wash conditions, the hybridization and wash conditions are gradually increased until a probe binds to a perfectly matched complementary target with a signal to noise ratio that is at least 5× as high as that observed for hybridization of the probe to an unmatched target.

"Very stringent" conditions are selected to be equal to the thermal melting point ($T_m$) for a particular probe. The $T_m$ is the temperature (under defined ionic strength and pH) at which 50% of the test sequence hybridizes to a perfectly matched probe. For the purposes of the present invention, generally, "highly stringent" hybridization and wash conditions are selected to be about 5° C. lower than the $T_m$ for the specific sequence at a defined ionic strength and pH.

"Ultra high-stringency" hybridization and wash conditions are those in which the stringency of hybridization and wash conditions are increased until the signal to noise ratio for binding of the probe to the perfectly matched complementary target nucleic acid is at least 10× as high as that observed for hybridization to any of the unmatched target nucleic acids. A target nucleic acid which hybridizes to a probe under such conditions, with a signal to noise ratio of at least ½ that of the perfectly matched complementary target nucleic acid is said to bind to the probe under ultra-high stringency conditions.

Similarly, even higher levels of stringency can be determined by gradually increasing the hybridization and/or wash conditions of the relevant hybridization assay. For example, those in which the stringency of hybridization and wash conditions are increased until the signal to noise ratio for binding of the probe to the perfectly matched complementary target nucleic acid is at least 10×, 20×, 50×, 100×, or 500× or more as high as that observed for hybridization to any of the unmatched target nucleic acids. A target nucleic acid which hybridizes to a probe under such conditions, with a signal to noise ratio of at least ½ that of the perfectly matched complementary target nucleic acid is said to bind to the probe under ultra-ultra-high stringency conditions.

Nucleic acids which do not hybridize to each other under stringent conditions are still substantially identical if the polypeptides which they encode are substantially identical. This occurs, e.g., when a copy of a nucleic acid is created using the maximum codon degeneracy permitted by the genetic code.

Unique Subsequences

In one aspect, the invention provides a nucleic acid that comprises a unique subsequence in a nucleic acid selected from the sequences of O-tRNAs and O-RSs disclosed herein. The unique subsequence is unique as compared to a nucleic acid corresponding to any known O-tRNA or O-RS nucleic acid sequence. Alignment can be performed using, e.g., BLAST set to default parameters. Any unique subsequence is useful, e.g., as a probe to identify the nucleic acids of the invention.

Similarly, the invention includes a polypeptide which comprises a unique subsequence in a polypeptide selected from the sequences of O-RSs disclosed herein. Here, the unique subsequence is unique as compared to a polypeptide corresponding to any previously known polypeptide sequence.

The invention also provides for target nucleic acids which hybridizes under stringent conditions to a unique coding oligonucleotide which encodes a unique subsequence in a polypeptide selected from the sequences of O-RSs wherein the unique subsequence is unique as compared to a polypeptide corresponding to any of the control polypeptides (e.g., parental sequences from which synthetases of the invention were derived, e.g., by mutation). Unique sequences are determined as noted above.

Sequence Comparison, Identity, and Homology

The terms "identical" or percent "identity," in the context of two or more nucleic acid or polypeptide sequences, refer to two or more sequences or subsequences that are the same or have a specified percentage of amino acid residues or nucleotides that are the same, when compared and aligned for maximum correspondence, as measured using one of the sequence comparison algorithms described below (or other algorithms available to persons of skill) or by visual inspection.

The phrase "substantially identical," in the context of two nucleic acids or polypeptides (e.g., DNAs encoding an O-tRNA or O-RS, or the amino acid sequence of an O-RS) refers to two or more sequences or subsequences that have at least about 60%, about 80%, about 90–95%, about 98%, about 99% or more nucleotide or amino acid residue identity, when compared and aligned for maximum correspondence, as measured using a sequence comparison algorithm or by visual inspection. Such "substantially identical" sequences are typically considered to be "homologous," without reference to actual ancestry. Preferably, the "substantial identity" exists over a region of the sequences that is at least about 50 residues in length, more preferably over a region of at least about 100 residues, and most preferably, the sequences are substantially identical over at least about 150 residues, or over the full length of the two sequences to be compared.

Proteins and/or protein sequences are "homologous" when they are derived, naturally or artificially, from a common ancestral protein or protein sequence. Similarly, nucleic acids and/or nucleic acid sequences are homologous when they are derived, naturally or artificially, from a common ancestral nucleic acid or nucleic acid sequence. For example, any naturally occurring nucleic acid can be modified by any available mutagenesis method to include one or more selector codon. When expressed, this mutagenized nucleic acid encodes a polypeptide comprising one or more unnatural amino acid. The mutation process can, of course, additionally alter one or more standard codon, thereby changing one or more standard amino acid in the resulting mutant protein as well. Homology is generally inferred from sequence similarity between two or more nucleic acids or proteins (or subsequences thereof). The precise percentage of similarity between sequences that is useful in establishing homology varies with the nucleic acid and protein at issue, but as little as 25% sequence similarity is routinely used to establish homology. Higher levels of sequence similarity, e.g., 30%, 40%, 50%, 60%, 70%, 80%, 90%, 95%, or 99% or more, can also be used to establish homology. Methods for determining sequence similarity percentages (e.g., BLASTP and BLASTN using default parameters) are described herein and are generally available.

For sequence comparison and homology determination, typically one sequence acts as a reference sequence to which test sequences are compared. When using a sequence comparison algorithm, test and reference sequences are input into a computer, subsequence coordinates are designated, if necessary, and sequence algorithm program parameters are designated. The sequence comparison algorithm then calculates the percent sequence identity for the test sequence(s) relative to the reference sequence, based on the designated program parameters.

Optimal alignment of sequences for comparison can be conducted, e.g., by the local homology algorithm of Smith & Waterman, *Adv. Appl. Math.* 2:482 (1981), by the homology alignment algorithm of Needleman & Wunsch, *J. Mol. Biol.* 48:443 (1970), by the search for similarity method of Pearson & Lipman, *Proc. Nat'l. Acad. Sci. USA* 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by visual inspection (see generally Ausubel et al., infra).

One example of an algorithm that is suitable for determining percent sequence identity and sequence similarity is the BLAST algorithm, which is described in Altschul et al., *J. Mol. Biol.* 215:403–410 (1990). Software for performing BLAST analyses is publicly available through the National Center for Biotechnology Information (www.ncbi.nlm.nih.gov/). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, a cutoff of 100, M=5, N=−4, and a comparison of both strands. For amino acid sequences, the BLASTP program uses as defaults a wordlength (W) of 3, an expectation (E) of 10, and the BLOSUM62 scoring matrix (see Henikoff & Henikoff (1989) *Proc. Natl. Acad. Sci. USA* 89:10915).

In addition to calculating percent sequence identity, the BLAST algorithm also performs a statistical analysis of the similarity between two sequences (see, e.g., Karlin & Altschul, *Proc. Nat'l. Acad. Sci. USA* 90:5873–5787 (1993)). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.1, more preferably less than about 0.01, and most preferably less than about 0.001.

Mutagenesis and Other Molecular Biology Techniques

Polynucleotides and polypeptides of the invention and used in the invention can be manipulated using molecular biological techniques. General texts which describe molecular biological techniques include Berger and Kimmel, supra; Sambrook, supra, and Ausubel, supra. These texts describe mutagenesis, the use of vectors, promoters and many other relevant topics related to, e.g., the generation of genes that include selector codons for production of glycoproteins of the invention, orthogonal tRNAs, orthogonal synthetases, and pairs thereof.

Various types of mutagenesis are used in the invention, e.g., to mutate tRNA molecules, to produce libraries of tRNAs, to produce libraries of synthetases, to insert selector codons that encode an unnatural amino acid, e.g., an unnatural amino acid comprising a moiety where a saccharide moiety can be attached, or an unnatural amino acid that includes a saccharide moiety, in a protein or polypeptide of interest. They include but are not limited to site-directed, random point mutagenesis, homologous recombination, DNA shuffling or other recursive mutagenesis methods, chimeric construction, mutagenesis using uracil containing templates, oligonucleotide-directed mutagenesis, phosphorothioate-modified DNA mutagenesis, mutagenesis using gapped duplex DNA or the like, or any combination thereof. Additional suitable methods include point mismatch repair, mutagenesis using repair-deficient host strains, restriction-selection and restriction-purification, deletion mutagenesis, mutagenesis by total gene synthesis, double-strand break repair, and the like. Mutagenesis, e.g., involving chimeric constructs, is also included in the present invention. In one embodiment, mutagenesis can be guided by known information of the naturally occurring molecule or altered or mutated naturally occurring molecule, e.g., sequence, sequence comparisons, physical properties, crystal structure or the like.

Host cells are genetically engineered (e.g., transformed, transduced or transfected) with the polynucleotides of the invention or constructs which include a polynucleotide of the invention, e.g., a vector of the invention, which can be, for example, a cloning vector or an expression vector. For example, the coding regions for the orthogonal tRNA, the orthogonal tRNA synthetase, and the protein to be derivatized with, e.g., an unnatural amino acid comprising a moiety where a saccharide moiety can be attached, such as an aldehyde- or keto-derivatized amino acid, or an unnatural amino acid that includes a saccharide moiety, are operably linked to gene expression control elements that are functional in the desired host cell. Typical vectors contain transcription and translation terminators, transcription and translation initiation sequences, and promoters useful for regulation of the expression of the particular target nucleic acid. The vectors optionally comprise generic expression cassettes containing at least one independent terminator sequence, sequences permitting replication of the cassette in eukaryotes, or prokaryotes, or both (e.g., shuttle vectors) and selection markers for both prokaryotic and eukaryotic systems. Vectors are suitable for replication and/or integration in prokaryotes, eukaryotes, or preferably both. See Giliman & Smith, *Gene* 8:81 (1979); Roberts, et al., *Nature*, 328:731 (1987); Schneider, B., et al., *Protein Expr. Purif.* 6435:10 (1995); Ausubel, Sambrook, Berger (all supra). The vector can be, for example, in the form of a plasmid, a bacterium, a virus, a naked polynucleotide, or a conjugated polynucleotide. The vectors are introduced into cells and/or microorganisms by standard methods including electroporation (From et al., *Proc. Natl. Acad. Sci. USA* 82, 5824 (1985), infection by viral vectors, high velocity ballistic penetration by small particles with the nucleic acid either within the matrix of small beads or particles, or on the surface (Klein et al., *Nature* 327, 70–73 (1987)), and/or the like.

A catalogue of Bacteria and Bacteriophages useful for cloning is provided, e.g., by the ATCC, e.g., *The ATCC Catalogue of Bacteria and Bacteriophage* (1996) Gherna et al. (eds) published by the ATCC. Additional basic procedures for sequencing, cloning and other aspects of molecular biology and underlying theoretical considerations are also found in Sambrook (supra), Ausubel (supra), and in Watson et al. (1992) *Recombinant DNA Second Edition* Scientific American Books, NY. In addition, essentially any nucleic acid (and virtually any labeled nucleic acid, whether standard or non-standard) can be custom or standard ordered from any of a variety of commercial sources, such as the Midland Certified Reagent Company (Midland, Tex. mcrc.com), The Great American Gene Company (Ramona, Calif. available on the World Wide Web at genco.com), ExpressGen Inc. (Chicago, Ill. available on the World Wide Web at expressgen.com), Operon Technologies Inc. (Alameda, Calif.) and many others.

The engineered host cells can be cultured in conventional nutrient media modified as appropriate for such activities as, for example, screening steps, activating promoters or selecting transformants. These cells can optionally be cultured into transgenic organisms. Other useful references, e.g. for cell isolation and culture (e.g., for subsequent nucleic acid isolation) include Freshney (1994) *Culture of Animal Cells, a Manual of Basic Technique*, third edition, Wiley-Liss, New York and the references cited therein; Payne et al. (1992) *Plant Cell and Tissue Culture in Liquid Systems* John Wiley & Sons, Inc. New York, N.Y.; Gamborg and Phillips (eds) (1995) *Plant Cell, Tissue and Organ Culture*; Fundamental Methods Springer Lab Manual, Springer-Verlag (Berlin Heidelberg New York) and Atlas and Parks (eds) *The Handbook of Microbiological Media* (1993) CRC Press, Boca Raton, Fla.

Kits

Kits are also a feature of the invention. For example, a kit for producing a glycoprotein that comprises at least saccharide moiety is provided, where the kit includes a container containing a polynucleotide sequence encoding an O-tRNA, and/or an O-tRNA, and/or a polynucleotide sequence encoding an O-RS, and/or an O-RS. In one embodiment, the kit further includes an unnatural amino acid with a saccharide moiety, or an unnatural amino acid with a moiety to attach a saccharide moiety. In another embodiment, the kit further comprises instructional materials for producing the glycoprotein.

EXAMPLES

The following examples are offered to illustrate, but not to limit the invention. It is understood that the examples and embodiments described herein are for illustrative purposes only and that various modifications or changes in light thereof will be suggested to persons skilled in the art and are to be included within the spirit and purview of this application and scope of the appended claims.

Example 1

System for Incorporating a Keto Functional Group into Proteins

This example describes a system for preparing p-acetyl-L-phenylalanine and incorporating this unnatural amino acid into a protein.

The genetic codes of most known organisms encode the same common twenty amino acids as building blocks for the biosynthesis of proteins. Only in rare cases are selenocysteine (see, e.g., Bock, A., et al., (1991) *Mol. Microbiol.* 5:515–520) or pyrrolysine (see, e.g., Srinivasan, G., et al., (2002) *Science* 296:1459–1462; and, Hao, B., et al., (2002) *Science* 296:1462–1466) added. The side chains of the common amino acids comprise a surprisingly limited number of functional groups—nitrogen bases, carboxylic acids and amides, alcohols, and a thiol group, the remainder being simple alkanes or hydrophobic groups. The ability to augment the genetically encoded amino acids with new amino acids, for example, amino acids with metal chelating, fluorescent, redox active, photoactive or spin-labeled side chains, would significantly enhance our ability to manipulate the structures and functions of proteins and perhaps living organisms themselves. Recently, we reported that by adding new components to the translational machinery of *Escherichia coli* (*E. coli*), one could site-specifically incorporate with high fidelity a number of unnatural amino acids (see, e.g., Wang, L., et al. (2001) *Science* 292: 498–500; Wang, L., et al. (2002) *J. Am. Chem Soc.* 124:1836–1837; and, Zhang, Z., et al. (2002) *Angew. Chem. Int. Ed. Engl.* 41:2840–2842) into proteins in vivo. This Example demonstrates that this approach can be extended to add a keto containing amino acid to the genetic code of an organism, e.g., *E. coli*, and that the unique reactivity of the keto group can be used to selectively modify proteins in vitro with a wide variety of agents.

The keto group is ubiquitous in organic chemistry, and participates in a large number of reactions, from addition reactions to aldol condensations. Moreover, the unique reactivity of the keto group allows it to be selectively modified with hydrazide and hydroxylamine derivatives in the presence of the other amino acid side chains. See, e.g., Cornish, V. W., et al. (1996) *J. Am. Chem. Soc.* 118: 8150–8151; Geoghegan, K. F. & Stroh, J. G. (1992) *Bioconjug. Chem.* 3:138–146; and, Mahal, L. K., et al. (1997) *Science* 276: 1125–1128. Although present in cofactors (see, e.g., Begley, T. P., et al. (1997) in *Top. Curr. Chem.*, eds. Leeper, F. J. & Vederas, J. C. (Springer-Verlag, New York), Vol. 195, pp. 93–142), metabolites (see, e.g., Diaz, E., et al. (2001) *Microbiol. Mol. Biol. Rev.* 65: 523–569) and as a posttranslational modification to proteins (see, e.g., Okeley, N. M. & van der Donk, W. A. (2000) *Chem. Biol.* 7:R159–R171), this important functional group is absent from the side chains of the common amino acids. In order to genetically encode this functional group in *E. coli* in the form of p-acetyl-L-phenylalanine, a tRNA-synthetase pair was evolved that is capable of inserting this amino acid site-specifically into proteins in *E. coli* in response to (and only in response to) an amber nonsense codon. Importantly this tRNA-synthetase pair is orthogonal to its counterparts for the common 20 amino acids, i.e., the orthogonal synthetase (and only this synthetase) aminoacylates the orthogonal tRNA (and only this tRNA) with the unnatural amino acid only, and the resulting acylated tRNA inserts the unnatural amino acid only in response to the amber codon.

Materials and Methods

Preparation of p-acetyl-L-phenylalanine: Fmoc-p-acetyl-L-phenylalanine was purchased from RSP Amino Acid Analogues, Inc. (Worcester, Mass.). This compound (1.0 g, 2.3 mmol) was stirred with 4 mL of piperidine (20% in dimethyl formamide (DMF)) for 2 hours at room temperature. The solvent was evaporated to obtain white powder. The solid was then resuspended in 10 mL of cold water (0.1% trifluoroacetic acid (TFA)), and the supernatant was collected by filtration. Preparative reverse-phase HPLC (Microsorb C18, Rainin Instrument Co., Inc., Woburn, Mass.) was used to separate the desired product from the reaction mixture (5–30% $CH_3CN$ in $H_2O$ with 0.1% TFA over 30 min). The eluant ($t_R$=12 min) was lyophilized to obtain a white solid (0.45 g, 88%). $^1$H NMR (400 MHz $D_2O$): δ 7.85–7.28 (m, 4H), 4.23 (dd, 1H, 5.4 Hz), 3.2 (m, 2H), 2.7 (s, 3H). MS electrospray ionization (ESI): $[M+1]^+$ calcd for $C_{11}H_{13}NO_3$ 208.09, found 208.47.

Synthesis of p-acetyl-(±)-phenylalanine (see, e.g., Cleland, G. H. (1969) *J. Org. Chem.* 34:744–747): N-bromosuccinimide (NBS) was recrystallized prior to usage. NBS (18.5 g, 105 mmol) was added to a stirred solution of 4-methyl acetopone (13.4 g, 100 mmol) in 400 mL of carbon tetrachloride, followed by the addition of 2',2'-azobisiosbutyronitrile (AIBN) (0.43 g, 2.5 mmol). The reaction mixture was then heated to reflux for 4 hours. After completion of reaction (TLC: 8:1/hexanes:EtOAc), the solution was washed with water (1×100 mL), 1 M aqueous HCl (3×100 mL), 0.5% aqueous $NaHCO_3$ (3×100 mL) and brine (1×100 mL). The organic layer was collected and dried over anhydrous $MgSO_4$, and solvent was evaporated to obtain a yellow solid which was recrystallized with hexanes to afford the desired 1-(4-bromoethyl-phenyl)thanone as a solid (16.8 g, 78%). Dry ethanol (50 ml) was added dropwise to pentane-washed sodium pieces (2.3 g, 0.1 mol) under argon atmosphere over 15 minutes and the solution was stirred for another 15 minutes. Solid diethyl acetamidomalonate (2.7 g, 10 mmol) was then added over 30 minutes with stirring, followed by the dropwise addition of 1-(4-bromoethyl-phenyl)thanone (2.1 g, 10 mmol) in dry ethanol over 90 minutes. After the mixture was heated to reflux overnight and cooled, diethyl ether (150 mL) and water (100 mL) were added to the solution. The organic layer was separated and washed successively with 0.5% $NaHCO_3$ (3×100 mL) and brine (1×100 mL). After drying over anhydrous $MgSO_4$, solvent was removed in vacuo to afford a brown gummy solid. Hexanes-dichloromethane (4:1) was added to the residue, and the insoluble material was filtered out and washed exhaustively with 10:1 dichloromethane-benzene to afford 2-acetylamino-2-(4-acetyl-benzyl)malonic acid diethyl ester as a yellow solid (3.3 g, 95% crude yield). This compound was stirred with 4 M HCl in dioxane overnight. The mixture was then evaporated to dryness and recrystallized with water to afford p-acetyl-(±)-phenylalanine (13.2 g, 64% overall yield) as a white solid. $^1$H NMR (400 MHz, $D_2O$): δ 7.85–7.28 (m, 4H), 4.27 (dd, 1H, 5.4 HZ), 3.30 (m, 2H), 2.68 (s, 3H). $^{13}$C NMR (400 MHz, $D_2O$): δ 195.8, 174.3, 145.9, 133.1, 128.9, 127.8, 60.2, 38.3, 26.5. MS (ESI): $[M+1]^+$ calcd for $C_{11}H_{13}NO_3$ 208.09, found 208.07.

Mutant synthetase evolution: In the positive selection, plasmid pYC-J17 was used to express the $mutRNA_{CUA}^{Tyr}$ gene and the chloramphenicol acetyl transferase (CAT) gene with a TAG stop codon at Asp112. See, e.g., Wang, L., et al. (2001) *Science* 292: 498–500. Supercoiled DNA encoding the tyrosyl-tRNA synthetase (TyrRS) library was transformed into *E. coli* DH10B competent cells containing pYC-J17. Cells were then plated on minimal media plates containing 1% glycerol and 0.3 mM leucine (GMML) with 17 µg/mL tetracycline, 25 µg/mL kanamycin, 60 µg/mL of chloramphenicol, and 1 mM p-acetyl-L-phenylalanine. After incubation at 37° C. for 40 hours, colonies were pooled, and plasmids were isolated. Plasmids encoding mutant synthetases (pBK plasmids) were separated from pYC-J17 using gel electrophoresis and transformed into *E. coli* DH10B competent cells containing pLWJ17B3 for negative selection. Plasmid pLWJ17B3 expresses the $mutRNA_{CUA}^{Tyr}$ under the control of the lpp promoter and rrnC terminator, and the barnase gene with three amber codons at Gln2, Asp44, and Gly65 under the control of arabinose promoter. Transformed cells were grown on LB (Luria-Bertani) plates containing 0.2% arabinose, 50 μg/ml kanamycin, and 35 μg/ml chloramphenicol. After 8 hours, cells were removed from the plate, and pBK plasmids were purified for further rounds of selection. In the second and third round of positive selection, the concentration of chloramphenicol was increased to 80 and 100 μg/mL, respectively. After 3 positive selections alternating with 2 negative selections, eleven mutant TyrRS were identified that afforded an $IC_{50}$ value of 9 μg/ml chloramphenicol in the absence of p-acetyl-L-phenylalanine and 120 μg/ml chloramphenicol in the presence of p-acetyl-L-phenylalanine in an in vivo CAT assay. See, e.g., Wang, L. & Schultz, P. G. (2001) Chem. Biol. 8: 883–890. The protein sequences of these mutant TyrRS converged on 3 independent clones LW1, LW5 and LW6, although the codon usage of each mutant TyrRS differs.

Protein expression and purification: Plasmid pLEIZ was used to express the Z-domain gene with an amber codon at the $7^{th}$ position and a COOH-terminal His6 tag under the control of a bacteriophage T5 promoter and $t_0$ terminator, and the $mutRNA_{CUA}^{Tyr}$ gene under the control of the lpp promoter and rrnC terminator. The mutant synthetase gene isolated from clone LW1 (LW1RS) was encoded in plasmid pBK-LW1RS under the control of the constitutive E. coli GlnRS promoter and terminator. E. coli DH10B cells cotransformed with pLEIZ and pBK-LW1RS were grown in minimal media containing 1% glycerol and 0.3 mM leucine (GMML media) with 25 μg/mL kanamycin, 34 μg/mL of chloramphenicol, and 1.0 mM p-acetyl-(±)-phenylalanine. When cells reach an $OD_{600}$ of 0.5, isopropyl-β-D-thiogalactopyranoside (IPTG) (1 mM) was added to induce protein expression. After 5 hours, cells were pelleted and the protein was purified by $Ni^{2+}$ affinity chromatography under denaturing conditions according to the manufacturer's protocol (Qiagen, Valencia, Calif.). Proteins were then desalted with a PD-10 column (Amersham Pharmacia, Piscataway, N.J.) and eluted in water. The yield of protein was measured by Bradford assay (BCA kit, Biorad, Hercules, Calif.). Aliquots of protein were used for sodium dodecyl sulfate-polyacrylamide gel electrophoresis (SDS-PAGE) and mass spectrometry.

In vitro protein modification with fluorescein hydrazide and biotin hydrazide: The purified wild-type (wt) and mutant Z domain proteins were exchanged into phosphate buffered saline solution (PBS buffer, 100 mM potassium phosphate, pH 6.5, 0.5 M sodium chloride) by dialysis. Fluorescein hydrazide 1 (Molecular Probe, Eugene, Oreg.) or biotin hydrazide 2 (Molecular Probe, Eugene, Oreg.) was dissolved in DMF, and added into 0.07 μmol of each protein in silanized eppendorf tubes to a final concentration of 1 mM. PBS buffer (pH 6.5) was added to bring the final volume to 0.5 ml. The reaction mixture was kept at 25° C. for 18 hours. Unreacted dye or biotin was removed from the protein using a PD-10 column (Amersham Pharmacia, Piscataway, N.J.), and proteins were eluted with PBS buffer. To determine the labeling efficiency, the eluted protein samples were then analyzed by reverse-phase HPLC (ZORBAX SB-C18, 4.6 mm×250 mm, flow rate 1.0 mL/min, 10→40% $CH_3CN$ in aqueous 50 mM triethylamine acetate buffer, pH 7.0 over 70 min, Agilent, Palo Alto, Calif.). The retention time ($t_R$) for mutant Z domain without labeling was 39.3 min; the $t_R$ for fluorescein hydrazide labeled mutant Z domain was 40.7 min; the $t_R$ for biotin hydrazide labeled mutant Z domain was 40.9 min.

Fluorescence spectrum measurement: All fluorescence emission spectra were recorded using a FluoroMax-2 spectrofluorometer (Instruments S. A., Inc., Edison, N.J.) with excitation at 490 nm; both excitation and emission bandpass of 4 nm; a photomultiplier tube voltage of 950 V; and at a scan rate of 1 nm/sec. Ten nmol of each labeled protein were used. The reported spectra represent an average of 3 scans.
Results and Discussion
A Keto Amino Acid The keto group provides a unique chemical reactivity not present in the common twenty amino acids due to its ability to participate in addition reactions involving either the carbonyl group or the acidic Cα position. This group also provides an alternative to the natural amino acid cysteine for the selective modification of proteins with a large variety of chemical reagents. The reactive thiol group of cysteine has been extensively used to attach various biophysical probes to proteins. See, e.g., Creighton, T. E. (1986) Methods Enzymol. 131: 83–106; Altenbach, C., et al., (1990) Science 248:1088–1092; Brinkley, M. (1992) Bioconjug. Chem. 3: 2–13; Giuliano, K. A., et al. (1995) Annu. Rev. Biophys. Biomol. Struct. 24:405–434; Mannuzzu, L. M., et al., (1996) Science 271:213–216; Griffin, B. A., et al. (1998) Science 281: 269–272; Llopis, J., et al., (2000) Methods Enzymol. 327:546–564; and, Gaietta, G., et al., (2002) Science 296:503–507. Unfortunately, the labeling of single cysteine residues is often complicated by the presence of more than one reactive residue in a protein, as well as exchange reactions in the presence of free thiol when a disulfide linkage is used. Therefore, the availability of a nonproteinogenic amino acid with orthogonal reactivity makes possible selective modification of protein in cases where a single cysteine cannot be selectively labeled or where two different labels are needed. The keto group reacts readily with hydrazides, hydroxylamines, and semicarbazides under mild conditions in aqueous solution, and forms hydrazone, oxime, and semicarbazone linkages, respectively, which are stable under physiological conditions. See, e.g., Jencks, W. P. (1959) J. Am. Chem. Soc. 81:475–481; and, Shao, J. & Tam, J. P. (1995) J. Am. Chem. Soc. 117:3893–3899.

Several methods have been developed to selectively incorporate the carbonyl group into peptides and small proteins. Initially, an aldehyde was introduced at the N-termini of peptides by oxidizing N-terminal serine or threonine with periodate. The aldehyde group was coupled to biotin and fluorescent reporters (see, e.g., Geoghegan, K. F. & Stroh, J. G. (1992) Bioconjug. Chem. 3:138–146) or protein fragments containing a COOH-terminal hydrazide through a hydrazone linkage (see, e.g., Gaertner, H. F., et al., (1994) J. Biol. Chem. 269:7224–7230). The carbonyl group introduced by this method is restricted to the N-terminus and the protein must be stable to oxidation. Solid phase peptide synthesis (SPPS) was later employed for the preparation of peptide segments containing either a hydrazide or hydroxylamine, which subsequently react with a branched aldehyde core matrix to form peptide dendrimers (see, e.g., Shao, J. & Tam, J. P. (1995) J. Am. Chem. Soc. 117:3893–3899; and, Rose, K. (1994) J. Am. Chem. Soc. 116:30–33), or with a keto containing peptide segment to form synthetic proteins (see, e.g., Canne, L. E., et al., (1995) J. Am. Chem. Soc. 117:2998–3007). SPPS allows the keto group to be incorporated throughout the protein, but suffers the inherent difficulties associated with the synthesis of large peptides or proteins. This size limitation can be overcome in some cases by expressed protein ligation (EPL), in which a synthetic peptide is chemically ligated to the COOH-terminus of recombinant proteins. See, e.g., Muir, T. W., et al. (1998) *Proc. Natl. Acad. Sci. USA* 95:6705–6710. A ketone group containing peptide was prepared by SPPS and ligated to the Src homology 3 domain of the Abelson protein tyrosine kinase. See, e.g., Ayers, B., et al., (1999) *Biopolymers* 51:343–354.

An in vitro biosynthetic method has also been used to incorporate the keto group into proteins. See, e.g., Cornish, V. W., et al. (1996) *J. Am. Chem. Soc.* 118: 8150–8151. In this method, the unnatural amino acid containing the keto group is chemically acylated to an amber suppressor tRNA. When the acylated tRNA and the mutant gene are combined in an in vitro extract capable of supporting protein biosynthesis, the unnatural amino acid is selectively incorporated in response to a UAG codon. This method requires the suppressor tRNA to be chemically aminoacylated with the unnatural amino acid in vitro, and the acylated tRNA is consumed as a stoichiometric reagent during translation and cannot be regenerated, resulting in low protein yields. By evolving an orthogonal tRNA-synthetase pair with specificity for p-acetyl-L-phenylalanine, a keto amino acid can be incorporated into proteins, e.g., in response to the UAG codon directly in living *E. coli* cells. There should be no size limitation on the target protein as long as it can be expressed in the organism, e.g., *E. coli*, and it should be possible to express large amounts of the mutant protein. Moreover, as long as the labeling reagent is cell permeable and nontoxic, it may be possible to selectively introduce the label in whole cells.

Evolution of Mutant Synthetases with Specificities for p-acetyl-L-phenylalanine

The *Methanococcus jannaschii* tyrosyl-tRNA synthetase (TyrRS) and a mutant tyrosine amber suppressor tRNA (mutRNA$_{CUA}^{Tyr}$) were used as the starting point for the generation of the orthogonal tRNA-synthetase pairs. Previously, this pair was shown to be orthogonal in *E. coli*. See, e.g., Wang, L. & Schultz, P. G. (2001) *Chem. Biol.* 8: 883–890; and, Wang, L., et al. (2000) *J. Am. Chem. Soc.* 122:5010–5011. To change the amino acid specificity of the TyrRS so that it charges p-acetyl-L-phenylalanine and not any of the common 20 amino acids, a library of *M. jannaschii* TyrRS mutants was generated and screened. The crystal structure of the homologous *Bacillus stearothermophilus* TyrRS (see, e.g., Brick, P., et al. (1989) *J. Mol. Biol.* 208:83–98) was used to identify those residues that are within 6.5 Å of the para position of the aryl ring of bound tyrosine. Five corresponding residues (Tyr32, Glu107, Asp158, Ile159 and Leu162) in the active site of *M. jannaschii* TyrRS were randomly mutated by polymerase chain reaction (PCR) to generate a library 1.6×10$^9$ in size (see, e.g., Wang, L., et al. (2001) *Science* 292: 498–500). This TyrRS mutant library was first passed through a positive selection in the presence of 1 mM p-acetyl-L-phenylalanine which is based on the suppression of an amber stop codon at nonessential residue (Asp112) in chloramphenicol acetyl transferase (CAT) gene encoded on plasmid pYC-J17 (see, e.g., Wang, L., et al. (2001) *Science* 292: 498–500) in *E. coli*. Cells surviving in chloramphenicol must encode a mutant synthetase that aminoacylates the mutRNA$_{CUA}^{Tyr}$ with either a common amino acid(s) or p-acetyl-L-phenylalanine. DNA encoding the mutant synthetases was then isolated and transformed into a negative selection strain expressing the gene of a toxic protein, barnase, containing three amber codons at permissive sites (encoded on plasmid pLWJ17B3). Cells encoding a mutant synthetase that charges the mutRNA$_{CUA}^{Tyr}$ with natural amino acids will produce barnase and die. Because no p-acetyl-L-phenylalanine was added to the growth medium in the negative selection, survivors must encode a synthetase with specificity for the unnatural amino acid. After 3 rounds of positive selection at increasing concentrations of chloramphenicol, alternating with 2 rounds of negative selection, a number of clones emerged whose survival in chloramphenicol was dependent on the addition of p-acetyl-L-phenylalanine. These TyrRS's were characterized using an in vivo assay based on the suppression of the Asp112TAG codon in the CAT gene. See, e.g., Wang, L. & Schultz, P. G. (2001) *Chem. Biol.* 8: 883–890. Eleven TyrRS mutants were identified. Cells expressing the selected synthetase and the mutRNA$_{CUA}^{Tyr}$ survived in the absence of p-acetyl-L-phenylalanine on 9 μg/ml chloramphenicol on minimal media plates containing 1% glycerol and 0.3 mM leucine (GMML plate); in the presence of this unnatural amino acid, cells survived in 120 μg/ml chloramphenicol on GMML plates. This result suggests that the selected mutant synthetase has higher activity for p-acetyl-L-phenylalanine than for natural amino acids. Sequencing the DNA of these mutants revealed that they converge on 3 independent mutants on the protein level (LW1, LW5, and LW6), although they have different codon usage for amino acids. The active site mutations of the mutant synthetases are listed in Table 1. Based on the crystal structure of the homologous TyrRS from *B. stearothermophilus*, the conserved side chain of *M. jannaschii* Tyr32 and Asp158 likely form hydrogen bonds with the hydroxyl group of the substrate tyrosine. In the mutant synthetases, Tyr32 is mutated to either Leu or Ala, and Asp158 is mutated to Gly158. These mutations should disfavor the binding of tyrosine and may at the same time create extra room to accommodate the methyl group of p-acetyl-L-phenylalanine. Determination of the X-ray crystal structure of the mutants should clarify the exact roles of these mutants.

TABLE 1

Amino acid residues in the WT *M. jannaschii* (MJ) TyrRS and the evolved mutant synthetases with specificities for p-Acetyl-L-phenylalanine

| Amino acid residue | 32 | 158 | 159 | 162 | 167 |
| --- | --- | --- | --- | --- | --- |
| WT Mj TyrRS | Tyr | Asp | Ile | Leu | Ala |
| LW1 | Leu | Gly | Cys | Arg | Ala |
| LW5 | Leu | Gly | Thr | Arg | Ala |
| LW8 | Ala | Gly | Gly | Leu | Ile |

Characterization of Mutant Protein Containing p-acetyl-L-phenylalanine

To test the ability of the evolved synthetase and the mutRNA$_{CUA}^{Tyr}$ to selectively incorporate p-acetyl-L-phenylalanine into proteins, an amber stop codon was substituted at a permissive site (Lys7) in the gene for the Z domain of staphylococcal protein A (see, e.g., Nilsson, B., et al. (1987) *Protein Eng.* 1:107–113) with a COOH-terminal His6 tag. Z domain has a molecular weight of about 7.9 kD, so its mass can be measured with very high accuracy using ion cyclotron resonance (ICR) mass spectrometry. Cells transformed with the mutRNA$_{CUA}^{Tyr}$, LW1RS and Z domain gene (Lys7TAG) were grown in the presence of 1 mM p-acetyl-(±)-phenylalanine. The addition of the unnatural amino acid did not affect the growth rate of cells. The mutant protein was purified by Ni$^{2+}$ affinity chromatography with an overall isolated yield of 3.6 mg/L in minimal media. For comparison, the yield of Z domain was 9.2 mg/L in minimal media when the mutant TyrRS was replaced with the wild-type (wt) TyrRS. No Z domain was obtained in the absence of either p-acetyl-(±)-phenylalanine, the mutRNA$_{CUA}^{Tyr}$ or LW1RS, indicating a very high fidelity in the incorporation of the unnatural amino acid at this site. We have also been successful in incorporating p-acetyl-L-phenylalanine into other proteins such as Cdc42.

Both the wt Z domain protein expressed by mutRNA$_{CUA}^{Tyr}$/WT TyrRS and the mutant Z domain protein expressed by the mutRNA$_{CUA}^{Tyr}$/LW1RS were analyzed by electrospray ionization Fourier transform ion cyclotron resonance mass spectrometry (FT-ICR MS). For the wt Z domain protein, three peaks were observed with masses corresponding to the intact protein, the protein without the first methionine, and the acetylated form of the protein without the first methionine (confirmed by tandem mass spectrometric analysis of the N-terminal tryptic digested peptide fragment). For the mutant Z domain protein, the experimental monoisotopic mass of the intact protein was 7949.893 Da, which is within 2.2 ppm of the theoretical mass of 7949.874 Da. Two other peaks correspond to the protein without the first methionine ($M_{Experimental}$=7818.838 Da, $M_{Theoretical}$=7818.833 Da) and its acetylated form ($M_{Experimental}$=7860.843 Da, $M_{Theoretical}$=7860.844 Da), respectively. No peaks corresponding to mutant proteins with any other amino acid at the amber codon position were observed in the spectra. The signal-to-noise ratio of more than 1500 observed in the intact protein mass spectrum translates to a fidelity for the incorporation of p-acetyl-L-phenylalanine of better than 99.8%. Liquid chromatography tandem mass spectrometry of the tryptic digest was carried out to confirm the sequence of the $NH_2$-terminal peptide. The precursor ion at 606.23 Da, which corresponds to the doubly charged molecular ion of the $NH_2$-terminal tryptic peptide MTSVDNY*INK, was isolated and fragmented with an ion trap mass spectrometer (ITMS). The fragment ion masses could be unambiguously assigned, confirming the site-specific incorporation of p-acetyl-L-phenylalanine. These results clearly demonstrate that the evolved synthetase together with the $mutRNA_{CUA}^{Tyr}$ incorporate p-acetyl-L-phenylalanine and not any natural amino acid into the position encoded by the amber codon and at no other positions.

Site-specific Protein Modification with Fluorescein Hydrazide

We next determined whether the keto group of p-acetyl-L-phenylalanine could serve as a chemical handle for the site-specific modification of proteins in vitro. The purified mutant p-acetyl-L-phenylalanine Z domain protein (mutant Z domain) and wt Z domain protein were treated with 1 mM fluorescein hydrazide (Scheme 1) at 25° C. for 18 hours in phosphate buffer. After the reaction, proteins were separated from excess fluorescein hydrazide by size exclusion chromatography, and analyzed with sodium dodecyl sulfate-polyacrylamide gel electrophoresis (SDS-PAGE). The gel was first imaged with a fluoroimaging system, and then silver stained. The band for mutant Z domain shows a fluorescent signal while no fluorescence can be detected from the wt Z domain band. Aliquots of these two proteins were used to measure the fluorescence spectrum with 490 nm excitation. Only the Z domain protein containing p-acetyl-L-phenylalanine shows a fluorescence spectrum similar to that of fluorescein. No fluorescence signal was detected for wt Z domain, indicating that the labeling reaction occurred only between the hydrazide and the ketone, and not any existing functional groups in the wt protein. The labeled product was analyzed with quadrupole time-of-flight mass spectrometry (QTOF MS). An experimental monoisotopic mass of 8425.160 Da ($M_{Theoretical}$= 8424.958 Da) was obtained, confirming that the fluorescein hydrazide reacted with the mutant Z domain protein in a molar ratio of 1:1. To determine the labeling extent, the reaction mixture was separated by high performance liquid chromatography (HPLC). The ratio of the peak area of the labeled Z domain over that of the unlabeled Z domain was 90±5%.

Scheme 1

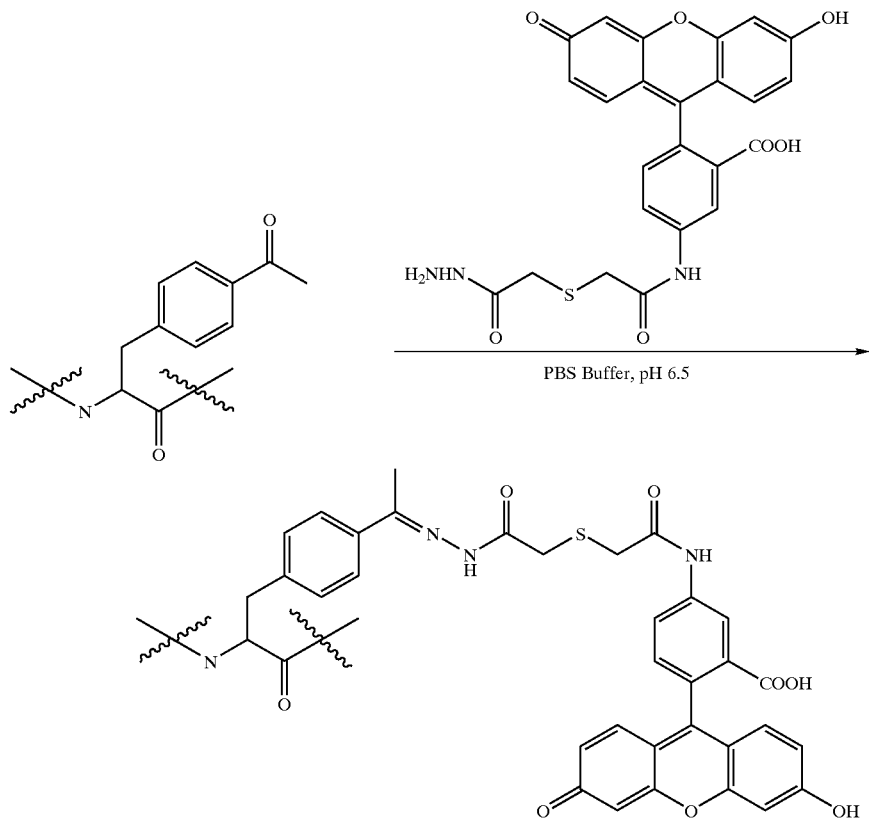

Site-specific Protein Modification with Biotin Hydrazide

To demonstrate the generality of this approach, we also labeled Z domain with the biotin hydrazide derivative (Structure C). The purified mutant and wt Z domain were treated with 1 mM biotin hydrazide in phosphate buffer at 25° C. for 18 hours. After dialysis against phosphate buffer to remove excess biotin hydrazide, the proteins were subject to SDS-PAGE. Separated proteins were transferred to nitrocellulose membrane and probed with a biotin-specific avidin-HRP conjugate. As expected, only the mutant Z domain containing p-acetyl-L-phenylalanine was detected, indicating it was labeled with biotin hydrazide. No signal was observed for wt Z domain. The labeling efficiency was 80±10% as determined by HPLC analysis as described in the fluorescein labeling experiment. The labeled protein was confirmed by QTOF MS ($M_{Experimental}$=8416.236, $M_{Theoretical}$=8416.146 Da) to be the product formed between one molecule of biotin hydrazide and one molecule of mutant Z domain. These experiments demonstrate the excellent specificity of the ketone handle for the in vitro modification of proteins.

2002/085923. Briefly, six residues ($Tyr^{32}$, $Ala^{67}$, $His^{70}$, $Gln^{155}$, $Asp^{158}$, $Ala^{167}$) in the active site of M. jannaschii TyrRS that are within 6.9 Å of the meta-position of the aryl ring of bound tyrosine in the crystal structure of Bacillus stearothermophilus TyrRS were mutated to all 20 amino acids at DNA level using the NNK codon scheme as described in Example 1 above. The constructed plasmid library pBK-lib contained around 1×10⁹ independent clones.

Evolution of orthogonal tRNA-synthetase pairs for incorporation of m-acetyl phenylalanine: After 3 rounds of positive selection and 2 rounds of negative selection, five candidate clones (SEQ ID NO: 17–21 of WO 2002/085923 and SEQ ID NO: 49–53 of WO 2002/085923) emerged whose survival in chloramphenicol was dependent on the addition of the unnatural amino acid. In the absence of m-acetyl phenylalanine, the $IC_{50}$ of chloramphenicol resistance for cells harboring the one of the three mutant TyrRS plasmids is 20 μg/ml. In the presence of m-acetyl phenylalanine, the $IC_{50}$ of resistance to chloramphenicol for the same cells is 100 μg/ml. The large difference between these two numbers reflects the ability of the selected syn- Structure C

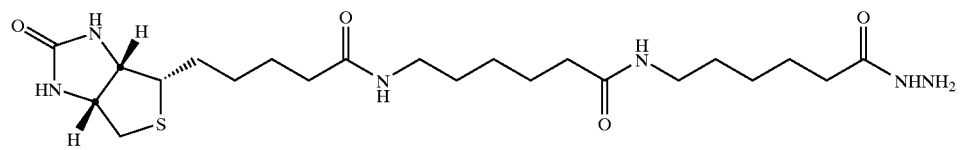

In summary, we have site-specifically incorporated a novel chemical functional group, the keto group, into proteins in vivo. This functional group can be selectively and efficiently labeled with, e.g., fluorescein and biotin in vitro by a specific chemical reaction between the keto group and hydrazide derivatives. This approach makes it possible to selectively label proteins with a wide variety of other hydrazide or hydroxylamine derivatives (including sugars, spin labels, metal chelators, crosslinking agents, polyethers, fatty acids and toxins), either as probes of protein structure and function, to generate proteins with enhanced catalytic or therapeutic properties, or for the development of bioassays using proteins. The ability to site-specifically incorporate a unique chemical handle into proteins directly in a living cell makes possible the in vivo modification of proteins with small molecule fluorophores for the in vivo imaging of protein localization, protein movement and conformational changes in proteins at molecular resolution. The in vivo labeling of proteins containing p-acetyl-L-phenylalanine with fluorophores in E. coli is also made possible by this technique.

See also corresponding application PCT/US03/32576 entitled "SITE SPECIFIC INCORPORATION OF KETO AMINO ACIDS INTO PROTEINS", filed Oct. 15, 2003, which is incorporated herein by reference.

Example 2

In Vivo Incorporation of Meta-tyrosine Analogues

An orthogonal TyrRS was generated for aminoacylation of the $mtRNA_{CUA}^{Tyr}$ (described in Example 1 of WO 2002/085923) with meta-tyrosine analogues.

Preparation of mutant TyrRS library plasmids: A library of plasmids encoding mutant M. jannaschii TryRSs directed at meta-substituted tyrosine derivatives was constructed, generally following the methods described in Example 1 of WO thetases to specify the incorporation of m-acetyl phenylalanine over the natural amino acids in the cell. The data for m-methoxy phenylalanine were similar; five clones were isolated (SEQ ID NO:22–26 of WO 2002/085923 and SEQ ID NO: 54–58 of WO 2002/085923).

Protein expression of unnatural amino acid incorporated DHFR: The m-methoxy phenylalanine and m-acetyl phenylalanine synthetases selected above were used to incorporate the relevant unnatural amino acids in response to an amber codon in DHFR as previously described in Example 1 of WO 2002/085923. As a negative control, cells containing both the orthogonal pair of tRNA-synthetase and amber-mutant vector encoding DHFR were grown in the absence of unnatural amino acids. The results of protein expression are shown in FIG. 10 of WO 2002/085923. These results clearly demonstrated the specificity of the orthogonal pair of tRNA-synthetase to incorporate unnatural m-methoxy phenylalanine and m-acetyl phenylalanine. The yields of expressed DHFR protein are approximately 0.5 mg/L of culture in both cases.

In one embodiment, compounds (e.g., hydrazide derivatives) can be used to in vivo label proteins with at least one unnatural amino acid, e.g., meta-tyrosine analogue.

Example 3

Synthesis of Glycoprotein Mimetics

The availability of a nonproteinogenic functional group with a unique reactivity greatly facilitates the selective chemical modification of proteins. The keto group is such a chemical handle—it is absent from the side chains of natural amino acids, and it reacts readily and selectively with hydrazide and hydroxylamine derivatives under mild conditions in the presence of the common amino acids. See, e.g., Cornish, V. W, et al., (1996) J. Am. Chem. Soc. 118:8150–8151 and references therein. The keto group has been included in peptides by solid phase peptide synthesis, and coupled with nucleophilic saccharide derivatives to construct neoglycopeptides. See, e.g., Rodriguez, E. C., et al., (1998) *J. Org. Chem.* 63:7134–7135. We recently developed a general method that allows for the site-specific incorporation of unnatural amino acids into proteins directly in living cells (See, e.g., WO 2002/085923; and, corresponding application PCT/US03/32576 entitled "SITE SPECIFIC INCORPORATION OF KETO AMINO ACIDS INTO PROTEINS", filed Oct. 15, 2003, which are incorporated herein by reference). See also, e.g., Wang, L., et al., (2001) *Science* 292:498–500. A keto containing amino acid, p-acetyl-L-phenylalanine, has been successfully incorporated in response to the amber nonsense codon with translation fidelity greater than 99.8%. See, e.g., Wang, L., et al., (2003) *Proc. Natl. Acad. Sci. U.S.A.* 100:56–61. This Example describes the preparation of homogeneous glycoprotein mimetics using the genetically encoded keto functionality together with aminooxy saccharide derivatives.

Two routes were explored to generate the glycoprotein mimetics (See FIG. 1). In the first approach, one saccharide derivatized with an aminooxy group is first coupled to the keto group, and additional saccharides are attached enzymatically with glycosyltransferases. In a more convergent second route, a glycan with defined structure is prepared as an aminooxy derivative, and is coupled directly to the protein in one step. The Z domain of staphylococcal protein A was used as the model protein, (see, e.g., Nilsson, B., et al., (1987). *Protein Eng.* 1:107–113) because its relatively small size (molecular weight 7.9 kD) facilitates mass spectrometric characterization with very high accuracy.

Figure 2:
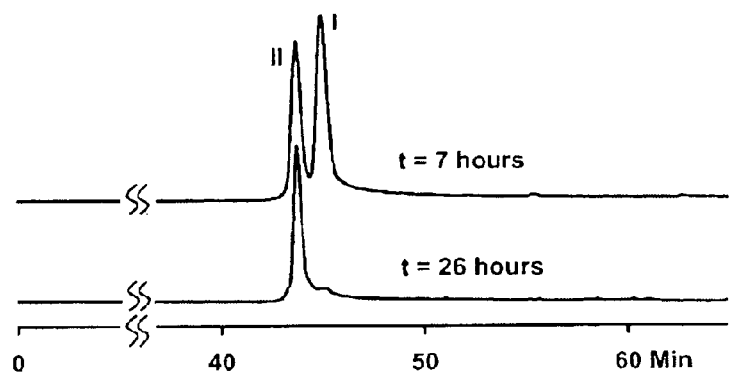
FIG. 2 illustrates HPLC analysis of the coupling reaction between aminooxy saccharide 1 (of FIG. 1) and mutant Z domain protein I (of FIG. 1) containing p-acetyl-L-phenylalanine at 7 hours and 26 hours.
Figure 3:
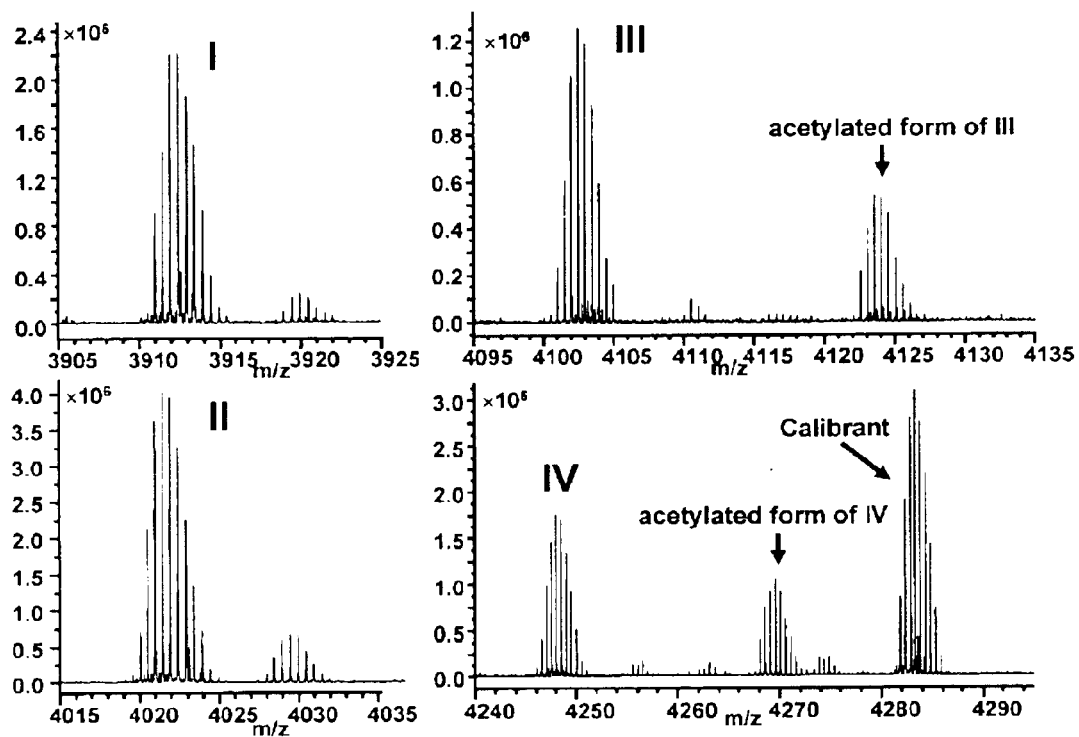
FIG. 3 illustrates high-resolution MALDI-FTICR MS spectra of mutant Z domain protein I (of FIG. 1), glycoprotein mimetics II, III, and IV (of FIG. 1). The $2^+$ isotopic cluster of each spectrum is shown.

The seventh codon of the corresponding gene was mutated to amber stop codon TAG and a His6 tag was added to the C-terminus to facilitate protein purification. P-Acetyl-L-phenylalanine was incorporated at the amber position to afford the mutant Z domain protein by previously reported protocols. See, e.g., Wang, L., et al., (2003) *Proc. Natl. Acad. Sci. U.S.A.* 100:56–61. Approximately 3.6 mg/L protein was obtained after nickel affinity chromatography. The beta-linked aminooxy analogue of N-acetylglucosamine (GlcNAc) 1 of FIG. 1 was then synthesized following published procedures. See, e.g., Cao, S., et al., (1995) *Tetrahedron* 51:6679–6686. The mutant Z domain protein (10 mg/mL) and aminooxy saccharide 1 (21 mM) were mixed in aqueous 100 mM sodium acetate buffer (pH 5.5) and incubated at 37° C. for 7 to 26 hrs. The reaction mixture was analyzed by reverse phase high-performance liquid chromatography (HPLC) by monitoring absorbance at 280 nm (See FIG. 2). Only two major peaks were observed, and the corresponding eluents were characterized by matrix-assisted laser desorption/ionization—Fourier transform ion cyclotron resonance mass spectrometry (MALDI-FTICR MS) (See FIG. 3). The monoisotopic masses obtained indicate that one peak ($t_R$=44.8 min) corresponds to the unreacted mutant Z domain ($M_{theoretical}$=7818.833 Da, $M_{experimental}$=7818.836 Da), and the other peak ($t_R$=43.2 min) corresponds to the mutant Z domain derivatized with the aminooxy saccharide 1 ($M_{Theoretical}$=8036.924 Da, $M_{experimental}$=8036.914 Da). When expressed in *E. coli*, Z domain protein has three forms: the intact protein, protein without the first methionine, and the acetylated form of the protein without methionine. The intact protein can be separated from the other two forms using reverse phase HPLC. To simplify mass spectrometric analysis, purified fraction containing Z domain without first methionine and its acetylated form can be used in this example. Two molecular peaks can be observed which correspond to these two forms in all mass spectra, as labeled in spectra for III and IV in FIG. 2. See FIG. 1 for structure. As a control, when tyrosine is incorporated at the seventh position of Z domain, no saccharide derivatized protein is observed. This fact, together with the high-accuracy mass (error <1.2 ppm) observed for the saccharide modified Z domain, confirmed that the aminooxy saccharide 1 is attached to the keto group, selectively. The coupling efficiency increases with time (determined from the areas of the HPLC peaks corresponding to starting material and product): the conversion of starting material to product was 42% after 7 hrs and greater than 95% after 26 hrs. (See FIG. 2).

We next determined whether a second saccharide could be coupled to the first enzymatically. The purified adduct II (5 mg/mL) (see FIG. 1 for structure) was incubated with UDP-galactose (UDP-Gal) (16 mM) and β-1,4-galactosyltransferase (0.4 units/mL) in 150 mM HEPES (N-2-hydroxyethylpiperazine-N'-2-ethanesulfonic acid) buffer (pH 7.4) for 48 hours at ambient temperature. Beta-1,4-galactosyltransferase is known to transfer galactose from the sugar nucleotide to the 4 position of a GlcNAc moiety to form Galβ1,4GlcNAc. See, e.g., Schanbacher, F. L., and Ebner, K. E. (1970) *J. Biol. Chem.* 245: 5057–5061. After separation by HPLC, a new peak was identified ($t_R$=42.5 min). The monoisotopic mass ($M_{theoretical}$=8198.977, $M_{experimental}$=8198.969) of the eluent measured by MALDI-FTICR MS confirmed that the galactose was coupled to GlcNAc to yield adduct III (See FIG. 3). See FIG. 1 for structure. The coupling efficiency determined by HPLC analysis was about 60%, a value close to that reported previously for β-1,4-galactosyltransferase. See, e.g., Witte, K., et al., (1997) *J. Am. Chem. Soc.* 119:2114–2118. This result indicates that the non-native linkage between the first saccharide and the protein does not significantly affect the glycosyltransferase reaction. Further reaction of this disaccharide labeled protein with CMP-sialic acid and α-2,3-sialyltransferase (see, e.g., Kitagawa, H., and Paulson, J. C. (1994) *J. Biol. Chem.* 269:1394–1401) resulted in the addition of sialic acid to galactose to afford IV ($t_R$=41.7 min), as confirmed by MALDI-FTICR MS ($M_{theoretical}$=8490.072, $M_{experimental}$=8490.014) (See FIG. 3). The coupling efficiency for conversion of III to IV was 65% based on HPLC analysis. See FIG. 1 for structures.

Glycoprotein mimetics III and IV were also prepared using a convergent route. See FIG. 1. Aminooxy GlcNAc (0.05 M) was converted to 2 using β-1,4-galactosyltransferase (0.75 units/mL) and the glycosyl donor UDP-galactose in 70% overall yield in 150 mM HEPES buffer (pH 7.4). After purification by aminopropyl silica gel HPLC, sialic acid was added to 2 (0.03 M) to afford 3 in the same buffer mentioned above in approximately 80% yield using α-2,3-sialyltransferase (0.22 units/mL) and CMP-sialic acid (0.03 M). Purified aminooxy analogue 2 and 3 (13 and 7.2 mM, respectively) were coupled to the Z domain protein (5 mg/mL) containing p-acetyl-L-phenylalanine in 100 mM aqueous sodium acetate buffer (pH 5.5) at ambient temperature to afford glycoprotein mimetics III and IV, respectively. See FIG. 1. The resultant III and IV were identical to the corresponding adducts prepared by the first sequential route, as confirmed by HPLC and MALDI-FTICR MS analysis. The coupling efficiency of 2 to I and 3 to I under the same reaction conditions for 26 hours were about 76% and 60%, respectively. The yields were lower than that for the coupling of 1 to I (95%) likely due to the increasing steric effect as the glycan becomes more complicated.

In summary, we have demonstrated a general method for the synthesis of homogeneous glycoprotein mimetics containing well-defined saccharide substituents.

Experimental Materials and Methods:

General: UDP-Gal, CMP-NeuAc, β-1,4-galactosyltransferase (β-1,4-GalT) and α-2,3-sialyltransferase (α-2,3-SialT) were purchased from Calbiochem. Unless otherwise stated, all chemicals were obtained from Aldrich, Acros or Sigma and used without further purification. Reactions were monitored by thin-layer chromatography (TLC) utilizing ninhydrin or cerium molybdate stain as the developing reagent. All non-aqueous reactions were carried out in oven-dried glassware under an inert Ar atmosphere. All non-aqueous solvents were distilled before use. NMR spectra were recorded on Bruker AMX-400, AMX-500 or AMX-600 MHz spectrometers and were referenced to residual solvent peaks (CDCl$_3$: $^1$H δ 7.24, $^{13}$C δ 77.0; CD$_3$OD: $^1$H δ 3.30, $^{13}$C δ 49.0; D$_2$O: $^1$H δ 4.76).

Compound 2 of FIG. 1: Compound 1 of FIG. 1 (5 mg, 0.021 mmol) and UDP-Gal (21 mg, 0.032 mmol) were dissolved in 350 μL HEPES buffer (150 mM, pH 7.4) containing a freshly prepared MnCl$_2$ solution (2 mmol). β-1,4-GalT (0.3 U, 0.1 U μL$^{-1}$) and alkaline phosphatase (0.5 U, 1 U μL$^{-1}$) were added and the reaction mixture was shaken gently at ambient temperature for 2 days. The reaction mixture was centrifuged and the supernatant was purified by aminopropyl silica gel HPLC employing a gradient elution of 100:0 A:B to 50:50 A:B over 90 min at a flow rate of 1 mL min$^{-1}$ where A=MeCN and B=H$_2$O. The retention time of the desired product was 53 min. Lyophilization of the column fractions afforded pure compound 2 of FIG. 1 (6 mg, 70%) as a white powder; $^1$H NMR (D$_2$O, 600 MHz) δ 4.58 (d, J=6.12, 1H), 4.42 (d, J=7.44, 1H), 3.96 (d, J=11.88 1H), 3.87 (m, 1H), 3.78 (dd, J=4.83, 12.3, 1H), 3.72–3.69 (m, 6H), 3.62 (dd, J=3.06, 10.08, 1H), 3.56 (m, 1H), 3.50 (m, 1H), 1.98 (s, 3H). $^{13}$C NMR (D$_2$O, 150 MHz) δ 175.18, 103.98, 103.31, 78.63, 75.78, 75.13, 72.92, 72.82, 71.39, 68.99, 61.46, 60.43, 53.80, 22.55. HR-FTMS (pos) calcd for C$_{14}$H$_{26}$N$_2$O$_{11}$ [M+Na]$^+$=421.1429, found 421.1448.

Compound 3 of FIG. 1: Compound 2 of FIG. 1 (5.3 mg, 0.013 mmol) and CMP-NeuAc (10 mg, 0.016 mmol) were dissolved in 450 μL HEPES buffer (150 mM, pH 7.4) containing a freshly prepared MnCl$_2$ solution (5 mmol). α-2,3-SialT (22 mU, 3.7 mU μL$^{-1}$) and alkaline phosphatase (50 mU, 50 mU μL$^{-1}$) were added and the reaction mixture was shaken gently at ambient temperature for 2 days. The reaction mixture was centrifuged and the supernatant was purified by aminopropyl silica gel HPLC employing a gradient elution of 100:0 A:B to 0:100 A:B over 30 min at a flow rate of 1 mL min$^{-1}$ where A=MeCN and B=H$_2$O. The corresponding fractions (27 min) were collected and lyophilized to give a white powder (7 mg, 76%). $^1$H NMR (D$_2$O, 600 MHz) δ 4.55 (d, J=8.34, 1H), 4.48 (d, J=7.86, 1H), 4.04 (dd, J=3.06, 9.60, 1H), 3.58–3.96 (m, 17H), 3.51 (m, 1H), 2.67 (dd, J=4.80, 12.72, 1H), 1.98 (s, 3H), 1.96 (s, 3H), 1.75 (t, J=12.30, 1H). ES-MS (neg) calcd for C$_{25}$H$_{43}$N$_3$O$_{19}$ [M-H]$^-$=688, found 688.

General procedure for coupling aminooxy saccharide derivative to mutant Z domain protein: In a typical reaction, aminooxy saccharide derivative (500 μg) and ~1 mg mutant Z domain protein were dissolved in 100 mM NaOAc buffer, pH 5.5. Water was added to a total volume of 100 μL and the reaction mixture was shaken at 37° C. for 26 h. Then the mixture was centrifuged and the supernatant was purified by reverse phase HPLC on a Agilent ZORBAX SB-C18 4.6 mm×250 mm column employing a gradient elution of 90:10 A:B to 60:40 A:B over 70 min at a flow rate of 1 mL min$^{-1}$ where A=H$_2$O with 0.1% TFA and B=MeCN with 0.1% TFA. The column fractions were neutralized with TrisCl buffer (pH 7.0) and desalted with a size exclusion column. After eluted with water, the eluent was lyophilized to afford pure II, III, and IV of FIG. 1 as a white powder in 96%, 76% and 60% yield, respectively.

Preparation of glycoprotein mimetics III and IV (of FIG. 1) using the sequential route: For preparation of III of FIG. 1, II of FIG. 1 (~0.5 mg) and UDP-Gal (1 mg) were dissolved in 90 uL of 150 mM HEPES buffer, pH 7.4 containing a freshly prepared MnCl$_2$ solution (0.5 mmol). β-1,4-GalT (40 mU, 40 mU μL$^{-1}$) and alkaline phosphatase (50 mU, 50 mU μL$^{-1}$) were added and the reaction mixture was shaken gently at ambient temperature for 2 days. The reaction mixture was centrifuged and the supernatant was purified by by reverse phase HPLC. For preparation of IV of FIG. 1, III of FIG. 1 (~0.5 mg) and CMP-NeuAc (0.5 mg) were dissolved in 90 uL of 150 mM HEPES buffer pH 7.4 containing a freshly prepared MnCl$_2$ solution (0.5 mmol). α-2,3-SialT (10 mU, 3.7 mU μL$^{-1}$) and alkaline phosphatase (50 mU, 50 mU μL$^{-1}$) were added and the reaction mixture was shaken gently at ambient temperature for 2 days. The reaction mixture was centrifuged and the supernatant was purified by reverse phase HPLC.

MALDI-FTICR MS: A home-build instrument with an APEX II console and 9.4 T magnet from Bruker Daltonics (Billerica, Mass.) was used for MALDI-FTICR MS experiments. Sugar moieties tend to fall apart when normal MALDI sample preparation involving TFA was used. We used a less sensitive but colder matrix. The matrix is a mixture of 3-hydroxypicolinic acid (20 mg mL$^{-1}$) and diammonium citrate (1 mg mL$^{-1}$). Decomposition of the glycoprotein was further minimized by the specialized intermediate pressure MALDI source of the FTICR that reduces metastable fragmentation by providing collisional cooling in the source.

Example 4

Another Strategy for the Synthesis of Glycoproteins

In one embodiment of the invention, another strategy has been developed to synthesize homogeneous glycoproteins in an organism, e.g., E. coli, by the cotranslational incorporation of a glycosylated amino acid. For example, myoglobin containing β-GlcNAc-serine at a defined position can be expressed in E. coli in good yield and with high fidelity. The β-GlcNAc moiety can be recognized by a carbohydrate binding protein or subsequently modified with a galactosyltransferase. This approach can be applicable to other post-translational modifications, e.g., protein phosphorylation, acetylation, methylation and the like.

Glycosylation is one of the most common post-translational modifications of proteins in eukaryotes and affects a wide range of protein functions from folding and secretion to biomolecular recognition and serum half life. See, e.g., R. A. Dwek, (1996) Chem. Rev. 96:683. While there have been significant advances in our understanding of the effects of glycosylation, the specific roles of oligosaccharide chains and the relationships between their structures and functions are just beginning to be understood. See, e.g., C. R. Bertozzi, & L. L. Kiessling, (2001) Science 291:2357. The primary challenge is that glycoproteins are typically produced as a mixture of glycoforms, making it difficult to isolate unique glycoforms from natural sources. A variety of methods have been developed to synthesize structurally defined glycoforms, but all impose severe restrictions on the size, quantity, and/or quality of the glycoprotein produced. See, e.g., P. Sears, & C. H. Wong, (2001) Science 291:2344;

M. Wacker et al., (2002) *Science* 298:1790; B. G. Davis, (2002) *Chem. Rev.* 102:579; and, H. C. Hang, & C. R. Bertozzi, (2001) *Acc. Chem. Res.* 34:727. In this example, a strategy and the components used to produce unique glycoforms in *E. coli* are described, which includes developing an orthogonal synthetase-tRNA pair that genetically encodes a glycosylated amino acid in response to a selector codon, e.g., an amber codon, TAG. The genetic incorporation of this and other saccharide-modified amino acids directly into proteins can significantly enhance our ability to both analyze and manipulate glycoprotein structure and function.

Methods were previously developed which for the first time allowed the systematic addition of amino acids with novel chemical and physical properties to the genetic code of *E. coli* (see, e.g., L. Wang, et al., (2001) *Science* 292:498; L. Wang, et al., (2002) *J. Am. Chem. Soc.* 124:1836; Z. Zhang, et al., (2002) *Angew. Chem. Int. Ed. Engl.* 41:2840; J. W. Chin et al., (2002) *J. Am. Chem. Soc.* 124:9026; J. W. Chin et al., (2002) *Proc. Natl. Acad. Sci. USA* 99:11020; S. W. Santoro, et al., (2002) *Nat. Biotechnol.* 20:1044; L. Wang, et al., (2003), *Proc. Natl. Acad. Sci. USA* 100:56; and, Z. Zhang et al., (2003) *Biochemistry* 42:6735) and yeast (see, e.g., J. W. Chin et al., *Science*, (2003 in press). In this approach, an amber suppressor *M. jannaschii* TyrRS-mutRNA$_{CUA}^{Tyr}$ pair that does not cross-react with endogenous tRNAs and synthetases is evolved to uniquely charge a desired unnatural amino acid. This methology can also allow one to directly incorporate glycosylated, phosphorylated, or methylated amino acids into proteins (see, e.g., T. Arslan, et al., (1997) *J. Am. Chem. Soc.* 119:10877), avoiding the need for selective enzymatic or chemical posttranslational modification of proteins. B-O-GlcNAc-L-serine (Compound A, GlcNAc: N-acetylglucosamine) was attempted to be site-specifically incorporated into proteins in *E. coli*. The O-GlcNAc modification is ubiquitous in nearly all eukaryotes, is involved in regulation of cell signaling, protein trafficking and cell growth, and is also a substrate from which more complex carbohydrates are generated. See, e.g., L. Wells, et al., (2001) *Science* 291:2376; and, N. Lamarre-Vincent, & L. Hsieh-Wilson, (2003) *J. Am. Chem. Soc.* 125:6612. Unfortunately, saccharide derivatives with free hydroxyl groups are transferred poorly across the membrane of eukaryotic cells, suggesting that substrate Compound A would unlikely be cell-permeable. See, e.g., A. K. Sarkar, et al., (1995), *Proc. Natl. Acad. Sci. USA* 92:3323. However, it has been shown that acetylation of the hydroxyl groups of sugars facilitates transport across cell membranes and that the hydroxyl acetyl groups can be deacetylated by nonspecific cytosolic esterases once inside the cell. See, e.g., N. Lamarre-Vincent, & L. Hsieh-Wilson, (2003) *J. Am. Chem. Soc.* 125:6612. Therefore, the acetylated derivative tri-acetyl-β-GlcNAc-serine Compound B, for which there is a commercially available precursor, N-Fmoc-tri-acetyl-β-GlcNAc-serine, was used in these experiments. Compound:

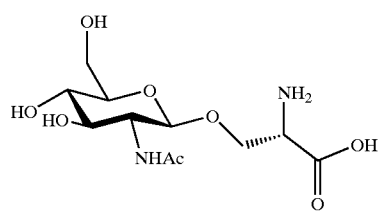

A

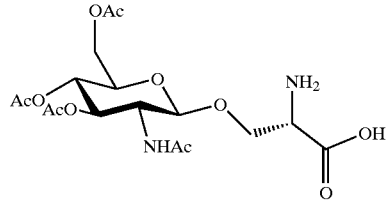

B

A series of positive and negative selections was used to isolate from a library of active site mutants, a TyrRS that specifically charges the orthogonal mutRNA$_{CUA}^{Tyr}$ with β-GlcNAc-serine in *E. coli*. Based on the X-ray structure of the homologous *Bacillus stearothermophilus* TyrRS, two libraries were constructed with active site residues randomized: one, encoded by plasmid pBK-lib-m, had residues Tyr$^{32}$, Ala$^{67}$, His$^{70}$, Gln$^{155}$, Asp$^{158}$, and Ala$^{167}$ randomized, and a second, encoded by plasmid pBK-lib, had residues Tyr$^{32}$, Glu$^{107}$, Asp$^{158}$, Ile$^{159}$, and Leu$^{162}$ randomized. These residues are all within 6.9 Å of the phenyl ring and are the primary residues that form the substrate binding pocket. The combined library had approximately 2.6×10$^9$ independent clones. This library was then subjected to a positive selection, based on suppression of an amber codon introduced at Asp112 in the chloramphenicol acetyltransferase (CAT) gene, to select TyrRS mutants capable of incorporating the glycosylated amino acid. Cells surviving at high concentrations of chloramphenicol must express a mutant TyrRS with the ability to insert either β-GlcNAc-serine or an endogenous amino acid in response to the Asp112TAG amber codon. A negative selection, based on suppression of three amber codons in the toxic barnase gene, was then used to delete from the selected clones those mutant TyrRSs that incorporate endogenous amino acids. After five rounds of positive selection and four rounds of negative selection, three clones emerged which survived at high concentration of chloramphenicol. These clones and their mutations are as following: S1-90 (Glu$^{107}$→Pro$^{107}$, Asp$^{158}$→Cys$^{158}$, Ile$^{159}$→Tyr$^{159}$, Leu$^{162}$→Arg$^{162}$), S4-5 (Tyr$^{32}$→Gly$^{32}$, Glu$^{107}$→Gly$^{107}$, Asp$^{158}$→Cys$^{158}$, Leu$^{162}$→His$^{162}$), S1-5 (Glu$^{107}$→Cys$^{107}$, Asp$^{158}$→His$^{158}$, Ile$^{159}$→Asp$^{159}$, Leu$^{162}$→Met$^{162}$). All of these clones appear to be highly selective for β-GlcNAc-serine, since replacement of Compound B with 1 mM of serine, α-tri-acetyl-GalNAc-threonine, α/β-tri-acetyl-GalNAc-serine or β-tetra-acetyl-Glu-asparagine does not permit cell growth above 30 μg/ml of chloramphenicol. These in vivo genetic results suggest that the newly selected mutant TyrRSs have excellent specificity towards β-GlcNAc-L-serine.

To test the efficiency and fidelity of incorporation of Compound B, a mutant myoglobin gene (Gly4TAG) containing an amber codon at the fourth position and a C terminal His6 tag was generated. See, e.g., S. W. Santoro et al., (2002) *Nat. Biotechnol.* 20:1044. When the mutant synthetase, S1-90, was co-expressed with the mutRNA$_{CUA}^{Tyr}$ and Gly4TAG myoglobin genes in the presence of Compound B in minimal media, 1 mg/L of the full length mutant myoglobin was produced (See FIG. 4). For comparison, 5.5 mg/L of wild-type myoglobin was produced under similar condition, indicating a good level of suppression for S1-90. In the absence of either S1-90, mutRNA$_{CUA}^{Tyr}$, or Compound B, no expression of full-length myoglobin was observed by silver-stained SDS-PAGE (See FIG. 4).

Figure 4:
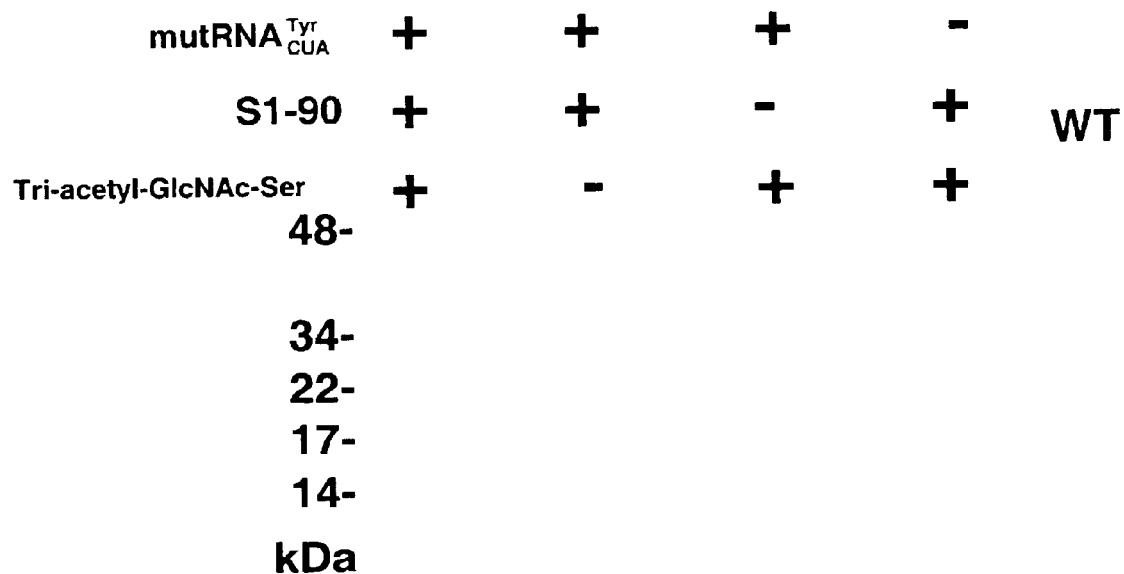
FIG. 4 illustrates expression of the Gly4→A mutant myoglobin (~18.5 kD). Proteins were purified by $Ni^{2+}$-affinity chromatography and resolved by SDS-PAGE. The gel was silver-stained.

FIG. 4 illustrates expression of the Gly4→Compound A mutant myoglobin (~18.5 kD). Proteins were purified by Ni$^{2+}$-affinity chromatography and resolved by SDS-PAGE. The gel was silver-stained. Lane 1 shows myoglobin was expressed in the presence of the orthogonal tRNA, synthetase S1-90, and Compound B. The band at ~18 kDa corresponds to the full-length myoglobin. Lane 2 shows proteins eluted after expression in the presence of the orthogonal tRNA and the synthetase S1-90 but in the absence of substrate Compound B. Lane 3 shows proteins eluted after expression in the presence of the orthogonal tRNA and substrate Compound B but in the absence of synthetase S1-90. Lane 4 shows proteins eluted after expression in the presence of the synthetase S1-90 and substrate Compound B but in the absence of the orthogonal tRNA. Lane 5 contains the purified wild type myglobin for comparison.

Figure 5:
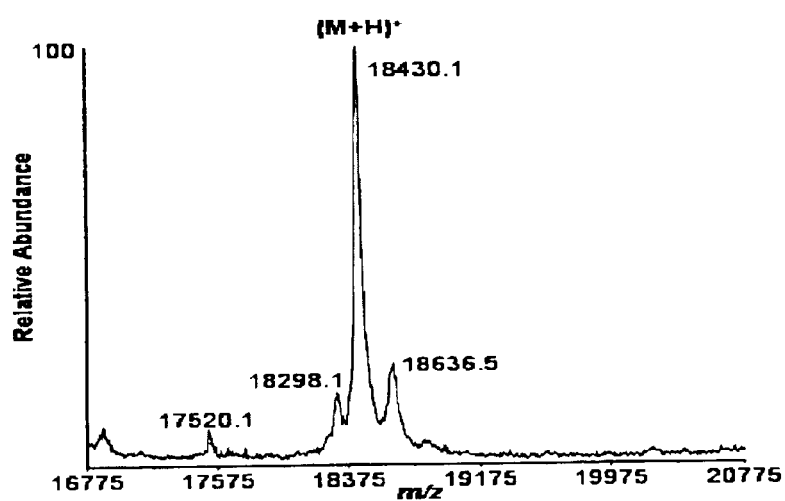
FIG. 5 illustrates MALDI-TOF analysis of the molecular weight of the Gly4→A mutant myoglobin.

High resolution MALDI-TOF analysis afforded a monoisotopic mass of the His6 tag-purified mutant myoglobin of 18430.1 Da, which agrees within 32 ppm with the theoretical mass of myoglobin containing Glc(OH)$_3$Nac-serine without methionine ($M_{theoretical}$=18429.5 Da). See FIG. 5. Note that the loss of the N terminal Met is common in E. coli. In addition, no signals corresponding to either the O-acetylated glycomyoglobin or the wild-type myoglobin were observed. The mass spectrum data confirm a high degree of specificity for the incorporation of GlcNAc-serine into myoglobin ($\geq$96%).

Figure 6A:
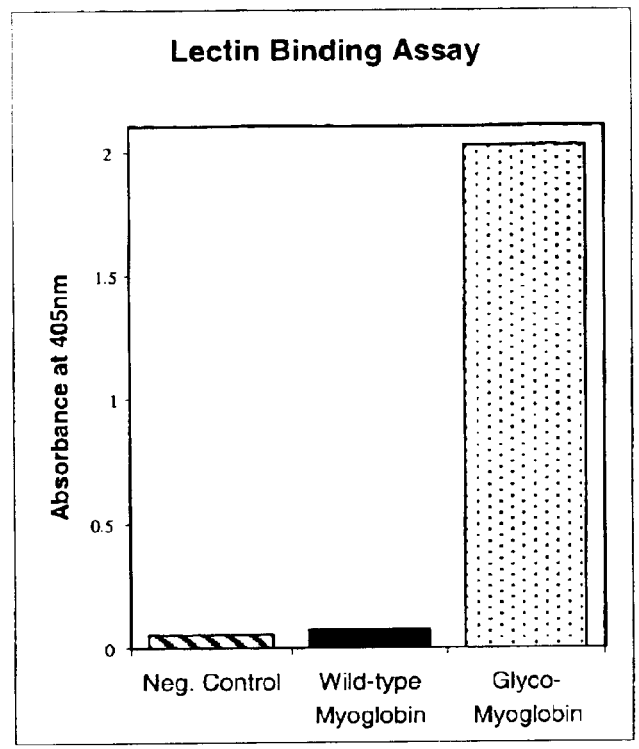
FIG. 6, Panel A, B and C illustrate characterization of the purified mutant myoglobin containing a glycosylated amino acid. Panel A illustrates binding of a GlcNAc-specific lectin, *Banderiraea simplicifolia* II (BSII), to wild-type myoglobin and glycomyoglobin. Panel B illustrates on-blot galactosyltransferase labeling glycomyoglobin with UDP-[$H^3$] galactose. Panel C illustrates quantitative analysis of the galactosyltransferase reaction, which was carried out in solution, and the radiolabeled galactose was normalized such that 1.0 corresponds to 100% transfer.
Figure 6B:
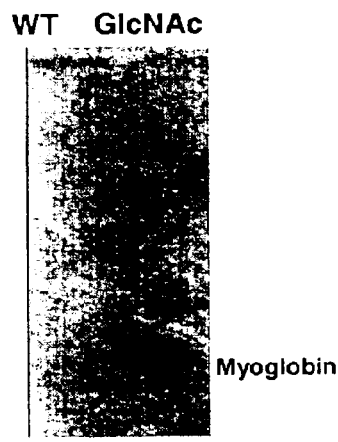
Figure 6C:
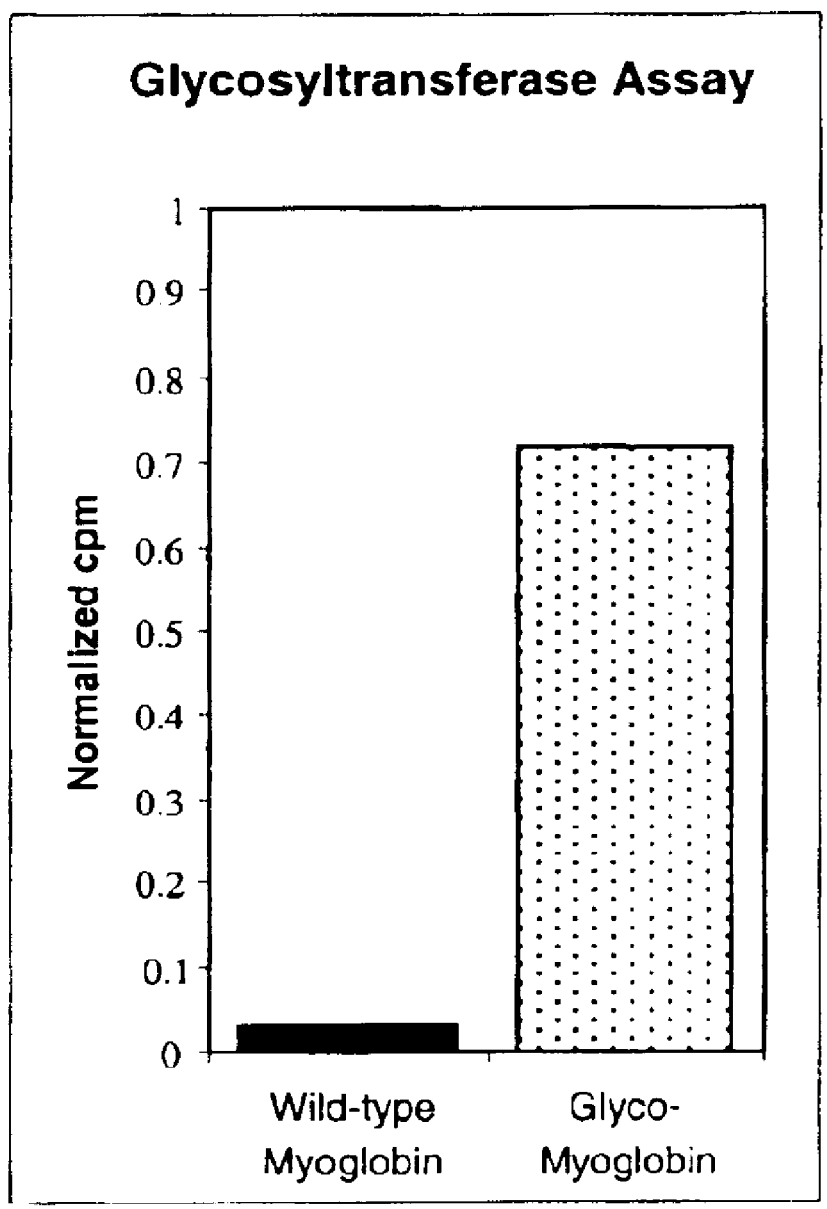

Several additional experiments were performed to further characterize the mutant myoglobin. First, an ELISA-like assay was used to analyze the binding of a GlcNAc-specific lectin, Bandeiraea simplicifolia II (BSII) (see, e.g., S. Ebisu, et al., (1978), Carbohydr. Res. 61:129), to wild-type myoglobin and glyco-myoglobin. See FIG. 6, Panel A. FIG. 6, Panel A illustrates binding of a GlcNAc-specific lectin, Banderiraea simplicifolia II (BSII), to wild-type myoglobin and glycomyoglobin. A$_{405}$ values are shown for wild-type myoglobin, glycomyoglobin, and negative control (no lectin added). Gly4→Compound A mutant myoglobin (200 ng) and wild type myoglobin (200 ng) were immobilized in microtiter plate wells and subsequently incubated with biotinylated BSII and streptavidin-alkaline phosphatase conjugate. Wells were incubated with p-nitrophenyl phosphate and monitored by measuring the absorbance at 405 nm. The two forms of myoglobin were immobilized in microtiter plate wells and then incubated with biotinylated BSII, streptavidin-alkaline phosphatase conjugate, and p-nitrophenyl phosphate, respectively. Wells containing wild-type myoglobin afforded a signal equivalent to negative control wells. In contrast, wells containing glycomyoglobin produced a signal at least 200 fold higher than that of wild-type myoglobin, demonstrating selective recognition by the GlcNAc-specific lectin. In addition, this result shows that the carbohydrate has not been modified to other isomeric forms such as GalNAc and ManNAc since this lectin is highly selective for GlcNAc (see, e.g., S. Ebisu, et al., (1978), Carbohydr. Res. 61:129).

We also investigated whether the O-GlcNAc-serine residue in myoglobin could be selectively modified with a galactosyltransferase. Beta-1,4-galactosyltransferase is known to transfer galactose (Gal) from the sugar nucleotide UDP-Gal to the 4 position of an N-acetylglucosamine (GlcNAc) to form Gal$\beta$1,4GlcNAc. To determine if the O-glycosylated myoglobin can be modified with UDP-Gal, both wild-type and O-glycosylated myoglobin were resolved by SDS-PAGE and transferred to a PVD membrane. The membrane was then incubated with bovin milk galactosyltransferase and radioactive UDP-[H$^3$]-galactose at room temperature for 24 hours. See, e.g., K. Kamemura, et al., (2002), J. Biol. Chem. 277:19229. Incorporation of [H$^3$]-Gal was monitored by exposing the membrane to X-ray film. Only the glycomyoglobin was labeled; no detectable signal was observed for the wild-type myoglobin. See FIG. 6, Panel B. FIG. 6, Panel B illustrates on-blot galactosyltransferase labeling glycomyoglobin with UDP-[H$^3$] galactose. Wild type myoglobin (1 µg) and Gly4→Compound A mutant myoglobin (1 µg) were resolved by 12% SDS-PAGE and transferred to a PVD membrane. The membrane was then treated with bovine milk galactosyltransferase (1 U), UDP-[H$^3$]galactose (0.5 µCi) and calf intestinal alkaline phosphatase (1 U) for 24 hours at room temperature. After extensive washes, the membrane was exposed to X-ray film using Enhanced autoradiography.

For quantitative analysis, the glycosyltransfer reaction was also carried out in solution. See, e.g., K. Witte, et al., (1997) J. Am. Chem. Soc. 119:2114. After incubation for 48 hours at room temperature, a 72% yield of disaccharide was obtained based on the radiolabel present. See FIG. 6, Panel C. FIG. 6, Panel C illustrates quantitative analysis of the galactosyltransferase reaction, which was carried out in solution, and the radiolabeled galactose was normalized such that 1.0 corresponds to 100% transfer. To the solutions containing HPLC-purified wild type myoglobin (100 µg) and Gly4→Compound A mutant myoglobin (100 µg) were added pyruvate kinase (5 U), UDP-glucose pyrophosphorylase (1 U), inorganic pyrophosphorylase (10 U), galactose-1-phosphate-uridyl transferase (1 U), bovine milk galactosyltransferase (2 U), glucose-1-phosphate (3 µmol), uridyl diphosphate (3 µmol), phosphoenolpyruvate (0.01 mmol), and DTT (2 µmol). After the reaction was adjusted to pH 7.2, [H$^3$]-galactose-1-phosphate (0.01 mmol) was added. The reaction was carried out for 48 hours at room temperature. Protein products were separated with a PD-10 Sephadex 25 column. Incorporated radiolabel was measured on a liquid scintillation analyzer.

These studies demonstrate that $\beta$-GlcNAc-L-serine can be cotranslationally incorporated into proteins in E. coli with excellent specificity and good yield. The incorporated $\beta$-GlcNAc-serine can serve as a primary glycosylation site to which saccharides can be added sequentially with glycosyltransferase, e.g., K. Kamemura, et al., (2002), J. Biol. Chem. 277:19229.

Materials and Methods

Directed evolution of mutant TyrRS enzymes. The general procedures for the positive and negative selections have been reported previously. See, e.g., Z. Zhang et al., (2003) Biochemistry, 42:6735. Briefly, a combination of plasmid pBK-lib-m (see, e.g., Z. Zhang et al., (2003) Biochemistry 42:6735) and pBK-lib (see, e.g., L. Wang, et al., (2001) Science 292:498) was transformed into competent E. coli DH10B harboring the plasmid pRep(2)/YC (see, e.g., S. W. Santoro, et al., (2002) Nat. Biotechnol. 20:1044). The transformed cells were grown in 500 ml of GMML medium (1×M9 minimal media with 1% glycerol, 0.3 mM leucine, 1 mM MgCl$_2$, 0.1 mM CaCl$_2$ and 0.5% NaCl) containing 40 µg/ml tetracycline, 50 µg/ml kanamycin, 68 µg/ml chloramphenicol, and 1 mM Compound B for 60 hours at 37° C. Plasmids (pBK) were purified from surviving cells and transformed into E. coli DH10B harboring pLWJ17B3 (see, e.g., L. Wang, et al., (2001) Science 292:498) to start the negative selection. Cells were then plated onto LB (Luria-Bertani) plates containing 40 µg/ml chloramphenicol, 50 µg/ml kanamycin, and 0.02% L-arabinose and incubated at 37° C. for 8 hours. Plasmids pBK were purified from surviving cells and used for the subsequent positive and negative selections. After five rounds of positive and four rounds of negative selections, three candidate pairs of orthogonal tRNA-synthetases that conferred substrate-dependent chloramphenicol resistance were isolated and sequenced.

Expression and characterization of mutant myoglobin. DH10B cells containing pBAD/JYAMB-4TAG (see, e.g., S. W. Santoro, et al., (2002) *Nat. Biotechnol.* 20:1044) and pS1-90 were grown in a 500 ml GMML culture containing kanamycin, tetracycline, 0.02% L-arabinose, 5 µM $FeCl_3$, and 0 or 1 mM of Compound B. The cells were pelleted, lysed, and the proteins were purified by affinity chromatography with $Ni^{2+}$-NTA beads under native conditions. Proteins were analyzed by 12% SDS-PAGE and silver-stained. Aliquots of purified proteins were subject to high resolution mass spectrometric analysis. Matrix-assisted laser desorption ionization (MALDI) with a time-of-flight (TOF) mass spectrometer (Voyager DE-STR, Applied Biosystems, Foster City, Calif.) was used to measure the molecular weight of the protein. Protein samples were desorbed and ionized upon irradiation from a 337 nm nitrogen laser. Sinapinic acid was used as the MALDI matrix. Lectin binding and glycosyltransferase reactions were carried out following the established protocols (see, e.g., K. Kamemura, et al., (2002), *J. Biol. Chem.* 277:19229; and, K. Witte, et al., (1997) *J. Am. Chem. Soc.* 119:2114).

Example 5

Sequences of Exemplary O-RSs

Exemplary O-RSs that can be used in the invention include SEQ ID Nos: 1–6 (See Table 2), and exemplary O-tRNA that can be used in the invention includes SEQ ID NO: 7. Exemplary polynucleotides that encode O-RSs include SEQ ID NOs.: 8–10.

It is understood that the examples and embodiments described herein are for illustrative purposes only and that various modifications or changes in light thereof will be suggested to persons skilled in the art and are to be included within the spirit and purview of this application and scope of the appended claims.

While the foregoing invention has been described in some detail for purposes of clarity and understanding, it will be clear to one skilled in the art from a reading of this disclosure that various changes in form and detail can be made without departing from the true scope of the invention. For example, all the techniques and apparatus described above can be used in various combinations. All publications, patents, patent applications, and/or other documents cited in this application are incorporated by reference in their entirety for all purposes to the same extent as if each individual publication, patent, patent application, and/or other document were individually indicated to be incorporated by reference for all purposes.

TABLE 2

EXAMPLES OF SEQUENCES

| SEQ ID # | Sequences | Notes | RS |
|---|---|---|---|
| 1 | MDEFEMIKRNTSEIISEEELREVLKKDEKSALIGFEPSGKI HLGHYLQIKKMIDLQNAGFDIIILLADLHAYLNQKGELDEI RKIGDYNKKVFEAMGLKAKYVYGSEFQLDKDYTLNVYRLAL KTTLKRARRSMELIAREDENPKVAEVIYPIMQVNGCHYRGV DVAVGGMEQRKIHMLARELLPKKVVCIHNPVLTGLDGEGKM SSSKGNFIAVDDSPEEIRAKIKKAYCPAGVVEGNPIMEIAK YFLEYPLTIKRPEKFGGDLTVNSYEELESLFKNKELHPMDL KNAVAEELIKILEPIRKRL | LW1RS | RS aa |
| 2 | MDEFEMIKPNTSEIISEEELREVLKKDEKSALIGFEPSGKI HLGHYLQIKKMIDLQNAGFDIIILLADLHAYLNQKGELDEI RKIGDYNKKVFEAMGLKAKYVYGSEFQLDKDYTLNVYRLAL KTTLKRARRSMELIAREDENPKVAEVIYPIMQVNGTHYRGV DVAVGGMEQRKIHMLARELLPKKVVCIHNPVLTGLDGEGKM SSSKGNFIAVDDSPEEIRAKIKKAYCPAGVVEGNPIMEIAK YFLEYPLTIKRPEKFGGDLTVNSYEELESLFKNKELHPMDL KNAVAEELIKILEPIRKRL | LW5RS | RS aa |
| 3 | MDEFEMIKRNTSEIISEEELREVLKKDEKSAAIGFEPSGKI HLGHYLQIKKMIDLQNAGFDIIILLADLHAYLNQKGELDEI RKIGDYNKKVFEAMGLKAKYVYGSEFQLDKDYTLNVYRLAL KTTLKRARRSMELIAREDENPKVAEVIYPIMQVNGGHYLGV DVIVGGMEQRKIHMLARELLPKKVVCIHNPVLTGLDGEGKM SSSKGNFIAVDDSPEEIRAKIKKAYCPAGVVEGNPIMEIAK YFLEYPLTIKRPEKFGGDLTVNSYEELESLFKNKELHPMDL KNAVAEELIKILEPIRKRL | LW6RS | RS aa |
| 4 | MDEFEMIKRNTSEIISEEELREVLKKDEKSAYIGFEPSGKI HLGHYLQIKKMIDLQNAGFDIIILLADLHAYLNQKGELDEI RKIGDYNKKVFEAMGLKAKYVYGSPFQLDKDYTLNVYRLAL KTTLKRARRSMELIAREDENPKVAEVIYPIMQVNCYHYRGV DVAVGGMEQRKIHMLARELLPKKVVCIHNPVLTGLDGEGKM SSSKGNFIAVDDSPEEIRAKIKKAYCPAGVVEGNPIMEIAK YFLEYPLTIKRPEKFGGDLTVNSYEELESLFKNKELHPMDL KNAVAEELIKILEPIRKRL | S1-90 | RS aa |

TABLE 2-continued

EXAMPLES OF SEQUENCES

| SEQ ID # | Sequences | Notes | RS |
|---|---|---|---|
| 5 | MDEFEMIKRNTSEIISEEELREVLKKDEKSAGIGFEPSGKI HLGHYLQIKKMIDLQNAGFDIIILLADLHAYLNQKGELDEI RKIGDYNKKVFEAMGLKAKYVYGSGFQLDKDYTLNVYRLAL KTTLKRARRSMELIAREDENPKVAEVIYPIMQVNCMHYHGV DVAVGGMEQRKIHMLARELLPKKVVCIHNPVLTGLDGEGKM SSSKGNFIAVDDSPEEIRAKIKKAYCPAGVVEGNPIMEIAK YFLEYPLTIKRPEKFGGDLTVNSYEELESLFKNKELHPMDL KNAVAEELIKILEPIRKRL | S4-5 aa | RS |
| 6 | MDEFEMIKRNTSEIISEEELREVLKKDEKSAYIGFEPSGKI HLGHYLQIKKMIDLQNAGFDIIILLADLHAYLNQKGELDEI RKIGDYNKKVFEAMGLKAKYVYGS[C/S]FQLDKDYTLNVY RLALKTTLKRARRSMELIAREDENPKVAEVIYPIMQVNHDH YMGVDVAVGGMEQRKIHMLARELLPKKVVCIHNPVLTGLDG EGKMSSSKGNFIAVDDSPEEIRAKIKKAYCPAGVVEGNPIM EIAKYFLEYPLTIKRPEKFGGDLTVNSYEELESLFKNKELH PMDLKNAVAEELIKILEPIRKRL | S1-5 aa Position 107 can be either a C or S | RS |
| 7 | CCGGCGGUAGUUCAGCAGGGCAGAACGGCGGACUCUAAAUC CGCAUGGCGCUGGUUCAAAUCCGGCCCGCCGGACCA | mutRNA$_{CUA}^{Tyr}$ | tRNA |
| 8 | ATGGACGAATTTGAAATGATAAAGAGAAACACATCTGAAAT TATCAGCGAGGAAGAGTTAAGAGAGGTTTTAAAAAAAGATG AAAAAATCTGCTTACATAGGTTTTGAACCAAGTGGTAAAATA CATTTAGGGCATTATCTCCAAATAAAAAAGATGATTGATTT ACAAAATGCTGGATTTGATATAATTATATTGTTGGCTGATT TACACGCCTATTTAAACCAGAAGGAGAGTTGGATGAGATT AGAAAAATAGGAGATTATAACAAAAAAGTTTTTGAAGCAAT GGGGTTAAAGGCAAAATATGTTTATGGAAGTCCATTCCAGC TTGATAAGGATTATACACTGAATGTCTATAGATTGGCTTTA AAAACTACCTTAAAAAGAGCAAGAAGGAGTATGGAACTTAT AGCAAGAGAGGATGAAAATCCAAAGGTTGCTGAAGTTATCT ATCCAATAATGCAGGTTAATTGCTATCATTATAGGGGCGTT GATGTTGCAGTTGGAGGGATGGAGCAGAGAAAAATACACAT GTTAGCAAGGGAGCTTTTACCAAAAAAGGTTGTTTGTATTC ACAACCCTGTCTTAACGGGTTTGGATGGAGAAGGAAAGATG AGTTCTTCAAAAGGGAATTTTATAGCTGTTGATGACTCTCC AGAAGAGATTAGGGCTAAGATAAAGAAAGCATACTGCCCAG CTGGAGTTGTTGAAGGAAATCCAATAATGGAGATAGCTAAA TACTTCCTTGAATATCCTTTAACCATAAAAAGGCCAGAAAA ATTTGGTGGAGATTTGACAGTTAATAGCTATGAGGAGTTAG AGAGTTTATTTAAAAATAAGGAATTGCATCCAATGGATTTA AAAAATGCTGTAGCTGAAGAACTTATAAAGATTTTAGAGCC AATTAGAAAGAGATTATAA | S1-90 | RS poly-nucleotide |
| 9 | ATGGACGAATTTGAAATGATAAAGAGAAACACATCTGAAAT TATCAGCGAGGAAGAGTTAAGAGAGGTTTTAAAAAAAGATG AAAAAATCTGCTGGAATAGGTTTTGAACCAAGTGGTAAAATA CATTTAGGGCATTATCTCCAAATAAAAAAGATGATTGATTT ACAAAATGCTGGATTTGATATAATTATATTGTTGGCTGATT TACACGCCTATTTAAACCAGAAGGAGAGTTGGATGAGATT AGAAAAATAGGAGATTATAACAAAAAAGTTTTTGAAGCAAT GGGGTTAAAGGCAAAATATGTTTATGGAAGTGGATTCCAGC TTGATAAGGATTATACACTGAATGTCTATAGATTGGCTTTA AAAACTACCTTAAAAAGAGCAAGAAGGAGTATGGAACTTAT AGCAAGAGAGGATGAAAATCCAAAGGTTGCTGAAGTTATCT ATCCAATAATGCAGGTTAATTGTATGCATTATCACGGCGTT GATGTTGCAGTTGGAGGGATGGAGCAGAGAAAAATACACAT GTTAGCAAGGGAGCTTTTACCAAAAAAGGTTGTTTGTATTC ACAACCCTGTCTTAACGGGTTTGGATGGAGAAGGAAAGATG AGTTCTTCAAAAGGGAATTTTATAGCTGTTGATGACTCTCC AGAAGAGATTAGGGCTAAGATAAAGAAAGCATACTGCCCAG CTGGAGTTGTTGAAGGAAATCCAATAATGGAGATAGCTAAA TACTTCCTTGAATATCCTTTAACCATAAAAAGGCCAGAAAA ATTTGGTGGAGATTTGACAGTTAATAGCTATGAGGAGTTAG AGAGTTTATTTAAAAATAAGGAATTGCATCCAATGGATTTA AAAAATGCTGTAGCTGAAGAACTTATAAAGATTTTAGAGCC AATTAGAAAGAGATTATAA | S4-5 | RS poly-nucleotide |

TABLE 2-continued

EXAMPLES OF SEQUENCES

| SEQ ID # | Sequences | Notes | RS |
|---|---|---|---|
| 10 | ATGGACGAATTTGAAATGATAAAGAGAAACACATCTGAAAT<br>TATCAGCGAGGAAGAGTTAAGAGAGGTTTTAAAAAAAGATG<br>AAAAATCTGCTTACATAGGTTTTGAACCAAGTGGTAAAATA<br>CATTTAGGGCATTATCTCCAAATAAAAAAGATGATTGATTT<br>ACAAAATGCTGGATTTGATATAATTATATTGTTGGCTGATT<br>TACACGCCTATTTAAACCAGAAAGGAGAGTTGGATGAGATT<br>AGAAAAATAGGAGATTATAACAAAAAAGTTTTTGAAGCAAT<br>GGGGTTAAAGGCAAAATATGTTTATGGAAGTTCATTCCAGC<br>TTGATAAGGATTATACACTGAATGTCTATAGATTGGCTTTA<br>AAAACTACCTTAAAAAGAGCAAGAAGGAGTATGGAACTTAT<br>AGCAAGAGAGGATGAAAATCCAAAGGTTGCTGAAGTTATCT<br>ATCCAATAATGCAGGTTAATCATGATCATTATATGGGCGTT<br>GATGTTGCAGTTGGAGGGATGGAGCAGAGAAAAATACACAT<br>GTTAGCAAGGGAGCTTTTACCAAAAAAGGTTGTTTGTATTC<br>ACAACCCTGTCTTAACGGGTTTGGATGGAGAAGGAAAGATG<br>AGTTCTTCAAAAGGGAATTTTATAGCTGTTGATGACTCTCC<br>AGAAGAGATTAGGGCTAAGATAAAGAAAGCATACTGCCCAG<br>CTGGAGTTGTTGAAGGAAATCCAATAATGGAGATAGCTAAA<br>TACTTCCTTGAATATCCTTTAACCATAAAAAGGCCAGAAAA<br>ATTTGGTGGAGATTTGACAGTTAATAGCTATGAGGAGTTAG<br>AGAGTTTATTTAAAAATAAGGAATTGCATCCAATGGATTTA<br>AAAAATGCTGTAGCTGAAGAACTTATAAAGATTTTAGAGCC<br>AATTAGAAAGAGATTATAA | S1-5 | RS poly-<br>nucleotide |

What is claimed is:

1. A method for synthesis of a glycoprotein, the method comprising:

incorporating, in a cell, an unnatural amino acid that comprises a first reactive group into a protein; wherein the incorporating step comprises incorporating the unnatural amino acid into the protein with an orthogonal tRNA/orthogonal aminoacyl-tRNA synthetase (O-tRNA/O-RS) pair, wherein the O-tRNA recognizes a selector codon and incorporates the unnatural amino acid into the protein in response to the selector codon, and wherein the O-RS aminoacylates the O-tRNA with the unnatural amino acid, and contacting the protein with a saccharide moiety that comprises a second reactive group, wherein the first reactive group reacts with the second reactive group to attach the saccharide moiety to the unnatural amino acid, thereby producing the glycoprotein.

2. The method of claim 1, wherein the first reactive group is an electrophilic moiety and the second reactive group is a nucleophilic moiety.

3. The method of claim 2, wherein the electrophilic moiety is a ketone or aldehyde moiety.

4. The method of claim 2, wherein the nucleophilic moiety is selected from the group consisting of: —NR$^1$—NH$_2$ (hydrazide), —NR$^1$(C=O)NR$^2$NH$_2$ (semicarbazide), —NR$^1$(C=S)NR$^2$NH$_2$ (thiosemicarbazide), —(C=O)NR$^1$NH$_2$ (carbonylhydrazide), —(C=S)NR$^1$NH$_2$ (thiocarbonylhydrazide), —(SO$_2$)NR$^1$NH$_2$ (sulfonylhydrazide), —NR$^1$NR$^2$(C=O)NR$^3$NH$_2$ (carbazide), NR$^1$NR$^2$(C=S)NR$^3$NH$_2$ (thiocarbazide), —O—NH$_2$ (hydroxylamine), where each R$^1$, R$^2$, and R$^3$ independently H, or an alkyl having 1–6 carbons.

5. The method of claim 4, wherein the nucleophilic moiety is selected from the group consisting of: hydrazide, hydroxylamine, semicarbazide, and carbohydrazide.

6. The method of claim 2, wherein the reaction product comprises an oxime, an amide, a hydrazone, a carbohydrazone, a thiocarbohydrazone, a sufonylhydrazone, a semicarbazone, or a thiosemicarbazone.

7. The method of claim 6, wherein the reaction product comprises a reduced hydrazone.

8. The method of claim 1, wherein the first reactive group is a nucleophilic moiety and the second reactive group is an electrophilic moiety.

9. The method of claim 8, wherein the electrophilic moiety is a keto or aldehyde moiety.

10. The method of claim 1, wherein the saccharide moiety comprises two or more carbohydrate moieties.

11. The method of claim 1, further comprising: c) contacting the saccharide moiety with a glycosyltransferase, a sugar donor moiety, and other reactants required for glycosyltransferase activity for a sufficient time to transfer a sugar from the sugar donor moiety to the saccharide moiety.

12. The method of claim 11, wherein the glycosyltransferase is selected from the group consisting of: a galactosyltransferase, a fucosyltransferase, a glucosyltransferase, an N-acetylgalactosaminyltransferase, an N-acetylglucosaminyltransferase, a glucuronyltransferase, a sialyltransferase, a mannosyltransferase, a glucuronic acid transferase, a galacturonic acid transferase, and an oligosaccharyltransferase.

13. The method of claim 11, wherein the method further comprises contacting a product of step (c) with at least a second glycosyltransferase and a second sugar donor moiety.

14. The method of claim 11, wherein the saccharide moiety comprises a terminal GlcNAc, the sugar donor moiety is UDP-Gal and the glycosyltransferase is a β-1,4-galactosyltransferase.

15. The method of claim 11, wherein the saccharide moiety comprises a terminal GlcNAc, the sugar donor moiety is UDP-GlcNAc and the glycosyltransferase is a β1-4N-acetylglucosaminyltransferase.

16. The method of claim 15, wherein the method further comprises contacting the product of the N-acetylglucosaminyltransferase reaction with a β1-4mannosyltransferase and GDP-mannose to form a saccharide moiety that comprises Manβ1-4GlcNAcβ1-4GlcNAc—.

17. The method of claim 16, wherein the method further comprises contacting the Manβ1-4GlcNAcβ1-4GlcNAc— moiety with an α1-3mannosyltransferase and GDP-mannose to form a saccharide moiety that comprises Manα1-3Manβ1-4GlcNAcβ1-4GlcNAc—.

18. The method of claim 17, wherein the method further comprises contacting the Manα1-3Manβ1-4GlcNAcβ1-4GlcNAc— moiety with an α1-6mannosyltransferase and GDP-mannose to form a saccharide moiety that comprises Manα1-6(Manα1-3)Manβ1-4GlcNAcβ1-4GlcNAc—.

19. The method of claim 18, wherein the method further comprises contacting the Manα1-6(Manα1-3)Manβ1-4GlcNAcβ1-4GlcNAc— moiety with a β1-2N-acetylglucosaminyltransferase and UDP-GlcNAc to form a saccharide moiety that comprises Manα1-6(GlcNAcβ1-2Manα1-3)Manβ1-4GlcNAcβ1-4GlcNAc—.

20. The method of claim 19, wherein the method further comprises contacting the Manα1-6(GlcNAcβ1-2Manα1-3)Manβ1-4GlcNAcβ1-4GlcNAc— moiety with a β1-2N-acetylglucosaminyltransferase and UDP-GlcNAc to form a saccharide moiety that comprises GlcNAcβ1-2Manα1-6(GlcNAcβ1-2Manα1-3)Manβ1-4GlcNAcβ1-4GlcNAc—.

21. The method of claim 11, wherein the method further comprises contacting the saccharide moiety with one or more of a β1-4N-acetylglucosaminyltransferase, an α1,3fucosyltransferase, an α1,2 fucosyltransferase, an α1,4fucosyltransferase, a β1-4galactosyltransferase, and a sialyltransferase, to form a biantennary or triantennary oligosaccharide structure.

22. The method of claim 1, wherein the O-RS comprises an amino acid sequence comprising any one of SEQ ID NO: 1, 2, or 3.

23. The method of claim 1, wherein the O-tRNA comprises a mutRNA$_{CUA}^{Try}$ (SEQ ID NO: 7).

24. The method of claim 1, wherein incorporating the unnatural amino acid into the protein comprises aminoacylating an O-tRNA with an unnatural amino acid.

25. The method of claim 1, wherein incorporating the unnatural amino acid into the protein comprises: aininoacylating an O-tRNA with an unnatural amino acid, using an O-RS, wherein the O-RS aminoacylates the O-tRNA more efficiently than the O-RS aminoacylates any endogenous tRNA of the translation system and wherein the O-RS aminoacylates the O-RS more efficiently with the unnatural amino acid than with a natural amino acid.

26. The method of claim 1 further comprising purifying the glycoprotein.

* * * * *

UNITED STATES PATENT AND TRADEMARK OFFICE
CERTIFICATE OF CORRECTION

PATENT NO. : 6,927,042 B2
DATED : August 9, 2005
INVENTOR(S) : Peter G. Schultz et al.

It is certified that error appears in the above-identified patent and that said Letters Patent is hereby corrected as shown below:

Column 83,
Lines 36-37, claim 9 should read:
9. The method of claim 8, wherein the electrophilic moiety is a ketone or aldehyde moiety.

Column 84,
Lines 49-56, claim 25 should read:
25. The method of claim 1, wherein incorporating the unnatural amino acid into the protein comprises: aminoacylating an O-tRNA with an unnatural amino acid, using an O-RS, wherein the O-RS aminoacylates the O-tRNA more efficiently than the O-RS aminoacylates any endogenous tRNA of the translation system and wherein the O-RS aminoacylates the O-RS more efficiently with the unnatural amino acid than with a natural amino acid.

Signed and Sealed this

First Day of November, 2005

JON W. DUDAS
*Director of the United States Patent and Trademark Office*

UNITED STATES PATENT AND TRADEMARK OFFICE
CERTIFICATE OF CORRECTION

PATENT NO. : 6,927,042 B2  
APPLICATION NO. : 10/686944  
DATED : August 9, 2005  
INVENTOR(S) : Peter G. Schultz et al.

It is certified that error appears in the above-identified patent and that said Letters Patent is hereby corrected as shown below:

Column 84,  
Line 55 of claim 25, delete "O-RS" and insert --O-tRNA--

Signed and Sealed this

Twenty-second Day of May, 2007

JON W. DUDAS  
*Director of the United States Patent and Trademark Office*

SEQUENCE LISTING

<160> NUMBER OF SEQ ID NOS: 10

<210> SEQ ID NO 1
<211> LENGTH: 306
<212> TYPE: PRT
<213> ORGANISM: Artificial
<220> FEATURE:
<223> OTHER INFORMATION: mutant synthetase derived from Methanococcus
      jannaschii tyrosyl-t
      RNA synthetase

<400> SEQUENCE: 1

```
Met Asp Glu Phe Glu Met Ile Lys Arg Asn Thr Ser Glu Ile Ile Ser
1               5                   10                  15

Glu Glu Glu Leu Arg Glu Val Leu Lys Lys Asp Glu Lys Ser Ala Leu
            20                  25                  30

Ile Gly Phe Glu Pro Ser Gly Lys Ile His Leu Gly His Tyr Leu Gln
        35                  40                  45

Ile Lys Lys Met Ile Asp Leu Gln Asn Ala Gly Phe Asp Ile Ile Ile
    50                  55                  60

Leu Leu Ala Asp Leu His Ala Tyr Leu Asn Gln Lys Gly Glu Leu Asp
65                  70                  75                  80

Glu Ile Arg Lys Ile Gly Asp Tyr Asn Lys Lys Val Phe Glu Ala Met
                85                  90                  95

Gly Leu Lys Ala Lys Tyr Val Tyr Gly Ser Glu Phe Gln Leu Asp Lys
            100                 105                 110

Asp Tyr Thr Leu Asn Val Tyr Arg Leu Ala Leu Lys Thr Thr Leu Lys
        115                 120                 125

Arg Ala Arg Arg Ser Met Glu Leu Ile Ala Arg Glu Asp Glu Asn Pro
    130                 135                 140

Lys Val Ala Glu Val Ile Tyr Pro Ile Met Gln Val Asn Gly Cys His
145                 150                 155                 160
```

Tyr Arg Gly Val Asp Val Ala Val Gly Gly Met Glu Gln Arg Lys Ile
                165                 170                 175

His Met Leu Ala Arg Glu Leu Leu Pro Lys Lys Val Val Cys Ile His
                180                 185                 190

Asn Pro Val Leu Thr Gly Leu Asp Gly Glu Gly Lys Met Ser Ser Ser
                195                 200                 205

Lys Gly Asn Phe Ile Ala Val Asp Asp Ser Pro Glu Glu Ile Arg Ala
            210                 215                 220

Lys Ile Lys Lys Ala Tyr Cys Pro Ala Gly Val Val Glu Gly Asn Pro
225                 230                 235                 240

Ile Met Glu Ile Ala Lys Tyr Phe Leu Glu Tyr Pro Leu Thr Ile Lys
                245                 250                 255

Arg Pro Glu Lys Phe Gly Gly Asp Leu Thr Val Asn Ser Tyr Glu Glu
                260                 265                 270

Leu Glu Ser Leu Phe Lys Asn Lys Glu Leu His Pro Met Asp Leu Lys
                275                 280                 285

Asn Ala Val Ala Glu Glu Leu Ile Lys Ile Leu Glu Pro Ile Arg Lys
            290                 295                 300

Arg Leu
305

<210> SEQ ID NO 2
<211> LENGTH: 306
<212> TYPE: PRT
<213> ORGANISM: Artificial
<220> FEATURE:
<223> OTHER INFORMATION: mutant synthetase derived from Methanococcus
      jannaschii tyrosyl-t
      RNA synthetase

<400> SEQUENCE: 2

Met Asp Glu Phe Glu Met Ile Lys Arg Asn Thr Ser Glu Ile Ile Ser
1               5                   10                  15

Glu Glu Glu Leu Arg Glu Val Leu Lys Lys Asp Glu Lys Ser Ala Leu
                20                  25                  30

Ile Gly Phe Glu Pro Ser Gly Lys Ile His Leu Gly His Tyr Leu Gln
                35                  40                  45

Ile Lys Lys Met Ile Asp Leu Gln Asn Ala Gly Phe Asp Ile Ile Ile
            50                  55                  60

Leu Leu Ala Asp Leu His Ala Tyr Leu Asn Gln Lys Gly Glu Leu Asp
65                  70                  75                  80

Glu Ile Arg Lys Ile Gly Asp Tyr Asn Lys Lys Val Phe Glu Ala Met
                85                  90                  95

Gly Leu Lys Ala Lys Tyr Val Tyr Gly Ser Glu Phe Gln Leu Asp Lys
                100                 105                 110

Asp Tyr Thr Leu Asn Val Tyr Arg Leu Ala Leu Lys Thr Thr Leu Lys
            115                 120                 125

Arg Ala Arg Arg Ser Met Glu Leu Ile Ala Arg Glu Asp Glu Asn Pro
130                 135                 140

Lys Val Ala Glu Val Ile Tyr Pro Ile Met Gln Val Asn Gly Thr His
145                 150                 155                 160

Tyr Arg Gly Val Asp Val Ala Val Gly Gly Met Glu Gln Arg Lys Ile
                165                 170                 175

His Met Leu Ala Arg Glu Leu Leu Pro Lys Lys Val Val Cys Ile His
                180                 185                 190

```
Asn Pro Val Leu Thr Gly Leu Asp Gly Glu Gly Lys Met Ser Ser Ser
        195                 200                 205

Lys Gly Asn Phe Ile Ala Val Asp Asp Ser Pro Glu Glu Ile Arg Ala
    210                 215                 220

Lys Ile Lys Lys Ala Tyr Cys Pro Ala Gly Val Val Glu Gly Asn Pro
225                 230                 235                 240

Ile Met Glu Ile Ala Lys Tyr Phe Leu Glu Tyr Pro Leu Thr Ile Lys
                245                 250                 255

Arg Pro Glu Lys Phe Gly Gly Asp Leu Thr Val Asn Ser Tyr Glu Glu
            260                 265                 270

Leu Glu Ser Leu Phe Lys Asn Lys Glu Leu His Pro Met Asp Leu Lys
        275                 280                 285

Asn Ala Val Ala Glu Glu Leu Ile Lys Ile Leu Glu Pro Ile Arg Lys
    290                 295                 300

Arg Leu
305

<210> SEQ ID NO 3
<211> LENGTH: 306
<212> TYPE: PRT
<213> ORGANISM: Artificial
<220> FEATURE:
<223> OTHER INFORMATION: mutant synthetase derived from Methanococcus
      jannaschii tyrosyl-t
      RNA synthetase

<400> SEQUENCE: 3

Met Asp Glu Phe Glu Met Ile Lys Arg Asn Thr Ser Glu Ile Ile Ser
1               5                   10                  15

Glu Glu Glu Leu Arg Glu Val Leu Lys Lys Asp Glu Lys Ser Ala Ala
            20                  25                  30

Ile Gly Phe Glu Pro Ser Gly Lys Ile His Leu Gly His Tyr Leu Gln
        35                  40                  45

Ile Lys Lys Met Ile Asp Leu Gln Asn Ala Gly Phe Asp Ile Ile Ile
    50                  55                  60

Leu Leu Ala Asp Leu His Ala Tyr Leu Asn Gln Lys Gly Glu Leu Asp
65                  70                  75                  80

Glu Ile Arg Lys Ile Gly Asp Tyr Asn Lys Lys Val Phe Glu Ala Met
                85                  90                  95

Gly Leu Lys Ala Lys Tyr Val Tyr Gly Ser Glu Phe Gln Leu Asp Lys
            100                 105                 110

Asp Tyr Thr Leu Asn Val Tyr Arg Leu Ala Leu Lys Thr Thr Leu Lys
        115                 120                 125

Arg Ala Arg Arg Ser Met Glu Leu Ile Ala Arg Glu Asp Glu Asn Pro
    130                 135                 140

Lys Val Ala Glu Val Ile Tyr Pro Ile Met Gln Val Asn Gly Gly His
145                 150                 155                 160

Tyr Leu Gly Val Asp Val Ile Val Gly Gly Met Glu Gln Arg Lys Ile
                165                 170                 175

His Met Leu Ala Arg Glu Leu Leu Pro Lys Lys Val Val Cys Ile His
            180                 185                 190

Asn Pro Val Leu Thr Gly Leu Asp Gly Glu Gly Lys Met Ser Ser Ser
        195                 200                 205

Lys Gly Asn Phe Ile Ala Val Asp Asp Ser Pro Glu Glu Ile Arg Ala
    210                 215                 220
```

```
Lys Ile Lys Lys Ala Tyr Cys Pro Ala Gly Val Val Glu Gly Asn Pro
225                 230                 235                 240

Ile Met Glu Ile Ala Lys Tyr Phe Leu Glu Tyr Pro Leu Thr Ile Lys
            245                 250                 255

Arg Pro Glu Lys Phe Gly Gly Asp Leu Thr Val Asn Ser Tyr Glu Glu
        260                 265                 270

Leu Glu Ser Leu Phe Lys Asn Lys Glu Leu His Pro Met Asp Leu Lys
        275                 280                 285

Asn Ala Val Ala Glu Glu Leu Ile Lys Ile Leu Glu Pro Ile Arg Lys
    290                 295                 300

Arg Leu
305

<210> SEQ ID NO 4
<211> LENGTH: 306
<212> TYPE: PRT
<213> ORGANISM: Artificial
<220> FEATURE:
<223> OTHER INFORMATION: mutant synthetase derived from Methanococcus
      jannaschii tyrosyl-t
      RNA synthetase

<400> SEQUENCE: 4

Met Asp Glu Phe Glu Met Ile Lys Arg Asn Thr Ser Glu Ile Ile Ser
1               5                   10                  15

Glu Glu Glu Leu Arg Glu Val Leu Lys Lys Asp Glu Lys Ser Ala Tyr
            20                  25                  30

Ile Gly Phe Glu Pro Ser Gly Lys Ile His Leu Gly His Tyr Leu Gln
        35                  40                  45

Ile Lys Lys Met Ile Asp Leu Gln Asn Ala Gly Phe Asp Ile Ile Ile
50                  55                  60

Leu Leu Ala Asp Leu His Ala Tyr Leu Asn Gln Lys Gly Glu Leu Asp
65                  70                  75                  80

Glu Ile Arg Lys Ile Gly Asp Tyr Asn Lys Lys Val Phe Glu Ala Met
            85                  90                  95

Gly Leu Lys Ala Lys Tyr Val Tyr Gly Ser Pro Phe Gln Leu Asp Lys
        100                 105                 110

Asp Tyr Thr Leu Asn Val Tyr Arg Leu Ala Leu Lys Thr Thr Leu Lys
    115                 120                 125

Arg Ala Arg Arg Ser Met Glu Leu Ile Ala Arg Glu Asp Glu Asn Pro
130                 135                 140

Lys Val Ala Glu Val Ile Tyr Pro Ile Met Gln Val Asn Cys Tyr His
145                 150                 155                 160

Tyr Arg Gly Val Asp Val Ala Val Gly Gly Met Glu Gln Arg Lys Ile
                165                 170                 175

His Met Leu Ala Arg Glu Leu Leu Pro Lys Lys Val Val Cys Ile His
            180                 185                 190

Asn Pro Val Leu Thr Gly Leu Asp Gly Glu Gly Lys Met Ser Ser Ser
        195                 200                 205

Lys Gly Asn Phe Ile Ala Val Asp Asp Ser Pro Glu Glu Ile Arg Ala
    210                 215                 220

Lys Ile Lys Lys Ala Tyr Cys Pro Ala Gly Val Val Glu Gly Asn Pro
225                 230                 235                 240

Ile Met Glu Ile Ala Lys Tyr Phe Leu Glu Tyr Pro Leu Thr Ile Lys
            245                 250                 255
```

```
Arg Pro Glu Lys Phe Gly Gly Asp Leu Thr Val Asn Ser Tyr Glu Glu
            260                 265                 270

Leu Glu Ser Leu Phe Lys Asn Lys Glu Leu His Pro Met Asp Leu Lys
            275                 280                 285

Asn Ala Val Ala Glu Leu Ile Lys Ile Leu Glu Pro Ile Arg Lys
            290                 295                 300

Arg Leu
305

<210> SEQ ID NO 5
<211> LENGTH: 306
<212> TYPE: PRT
<213> ORGANISM: Artificial
<220> FEATURE:
<223> OTHER INFORMATION: mutant synthetase derived from Methanococcus
      jannaschii tyrosyl-t
      RNA synthetase

<400> SEQUENCE: 5

Met Asp Glu Phe Glu Met Ile Lys Arg Asn Thr Ser Glu Ile Ile Ser
1               5                   10                  15

Glu Glu Glu Leu Arg Glu Val Leu Lys Lys Asp Glu Lys Ser Ala Gly
            20                  25                  30

Ile Gly Phe Glu Pro Ser Gly Lys Ile His Leu Gly His Tyr Leu Gln
            35                  40                  45

Ile Lys Lys Met Ile Asp Leu Gln Asn Ala Gly Phe Asp Ile Ile Ile
            50                  55                  60

Leu Leu Ala Asp Leu His Ala Tyr Leu Asn Gln Lys Gly Glu Leu Asp
65                  70                  75                  80

Glu Ile Arg Lys Ile Gly Asp Tyr Asn Lys Lys Val Phe Glu Ala Met
                85                  90                  95

Gly Leu Lys Ala Lys Tyr Val Tyr Gly Ser Gly Phe Gln Leu Asp Lys
            100                 105                 110

Asp Tyr Thr Leu Asn Val Tyr Arg Leu Ala Leu Lys Thr Thr Leu Lys
            115                 120                 125

Arg Ala Arg Arg Ser Met Glu Leu Ile Ala Arg Glu Asp Glu Asn Pro
130                 135                 140

Lys Val Ala Glu Val Ile Tyr Pro Ile Met Gln Val Asn Cys Met His
145                 150                 155                 160

Tyr His Gly Val Asp Val Ala Val Gly Gly Met Glu Gln Arg Lys Ile
                165                 170                 175

His Met Leu Ala Arg Glu Leu Leu Pro Lys Lys Val Val Cys Ile His
            180                 185                 190

Asn Pro Val Leu Thr Gly Leu Asp Gly Glu Gly Lys Met Ser Ser Ser
            195                 200                 205

Lys Gly Asn Phe Ile Ala Val Asp Asp Ser Pro Glu Glu Ile Arg Ala
            210                 215                 220

Lys Ile Lys Lys Ala Tyr Cys Pro Ala Gly Val Val Glu Gly Asn Pro
225                 230                 235                 240

Ile Met Glu Ile Ala Lys Tyr Phe Leu Glu Tyr Pro Leu Thr Ile Lys
                245                 250                 255

Arg Pro Glu Lys Phe Gly Gly Asp Leu Thr Val Asn Ser Tyr Glu Glu
            260                 265                 270

Leu Glu Ser Leu Phe Lys Asn Lys Glu Leu His Pro Met Asp Leu Lys
            275                 280                 285
```

Asn Ala Val Ala Glu Glu Leu Ile Lys Ile Leu Glu Pro Ile Arg Lys
    290                 295                 300

Arg Leu
305

<210> SEQ ID NO 6
<211> LENGTH: 306
<212> TYPE: PRT
<213> ORGANISM: Artificial
<220> FEATURE:
<223> OTHER INFORMATION: mutant synthetase derived from Methanococcus
      jannaschii tyrosyl-t
      RNA synthetase
<220> FEATURE:
<221> NAME/KEY: MISC_FEATURE
<222> LOCATION: (107)..(107)
OTHER INFORMATION: X can be either C or S

SEQUENCE: 6

Met Asp Glu Phe Glu Met Ile Lys Arg Asn Thr Ser Glu Ile Ile Ser
1               5                   10                  15

Glu Glu Glu Leu Arg Glu Val Leu Lys Lys Asp Glu Lys Ser Ala Tyr
            20                  25                  30

Ile Gly Phe Glu Pro Ser Gly Lys Ile His Leu Gly His Tyr Leu Gln
        35                  40                  45

Ile Lys Lys Met Ile Asp Leu Gln Asn Ala Gly Phe Asp Ile Ile Ile
    50                  55                  60

Leu Leu Ala Asp Leu His Ala Tyr Leu Asn Gln Lys Gly Glu Leu Asp
65                  70                  75                  80

Glu Ile Arg Lys Ile Gly Asp Tyr Asn Lys Lys Val Phe Glu Ala Met
                85                  90                  95

Gly Leu Lys Ala Lys Tyr Val Tyr Gly Ser Xaa Phe Gln Leu Asp Lys
            100                 105                 110

Asp Tyr Thr Leu Asn Val Tyr Arg Leu Ala Leu Lys Thr Thr Leu Lys
        115                 120                 125

Arg Ala Arg Arg Ser Met Glu Leu Ile Ala Arg Glu Asp Glu Asn Pro
    130                 135                 140

Lys Val Ala Glu Val Ile Tyr Pro Ile Met Gln Val Asn His Asp His
145                 150                 155                 160

Tyr Met Gly Val Asp Val Ala Val Gly Gly Met Glu Gln Arg Lys Ile
                165                 170                 175

His Met Leu Ala Arg Glu Leu Leu Pro Lys Lys Val Val Cys Ile His
            180                 185                 190

Asn Pro Val Leu Thr Gly Leu Asp Gly Glu Gly Lys Met Ser Ser Ser
        195                 200                 205

Lys Gly Asn Phe Ile Ala Val Asp Asp Ser Pro Glu Glu Ile Arg Ala
    210                 215                 220

Lys Ile Lys Lys Ala Tyr Cys Pro Ala Gly Val Val Glu Gly Asn Pro
225                 230                 235                 240

Ile Met Glu Ile Ala Lys Tyr Phe Leu Glu Tyr Pro Leu Thr Ile Lys
                245                 250                 255

Arg Pro Glu Lys Phe Gly Gly Asp Leu Thr Val Asn Ser Tyr Glu Glu
            260                 265                 270

Leu Glu Ser Leu Phe Lys Asn Lys Glu Leu His Pro Met Asp Leu Lys
        275                 280                 285

```
Asn Ala Val Ala Glu Glu Leu Ile Lys Ile Leu Glu Pro Ile Arg Lys
    290                 295                 300

Arg Leu
305

<210> SEQ ID NO 7
<211> LENGTH: 77
<212> TYPE: RNA
<213> ORGANISM: Artificial
<220> FEATURE:
<223> OTHER INFORMATION: mutant tyrosine amber suppressor tRNA

<400> SEQUENCE: 7
ccggcgguag uucagcaggg cagaacggcg gacucuaaau ccgcauggcg cugguucaaa    60
uccggcccgc cggacca                                                  77

<210> SEQ ID NO 8
<211> LENGTH: 921
<212> TYPE: DNA
<213> ORGANISM: Artificial
<220> FEATURE:
<223> OTHER INFORMATION: mutant synthetase derived from Methanococcus
      jannaschii tyrosyl-t
      RNA synthetase

<400> SEQUENCE: 8
atggacgaat tgaaatgat  aaagagaaac acatctgaaa ttatcagcga ggaagagtta    60
agagaggttt aaaaaaaga tgaaaaatct gcttacatag gttttgaacc aagtggtaaa   120
atacatttag gcattatct  ccaaataaaa aagatgattg atttacaaaa tgctggattt   180
gatataatta tattgttggc tgatttacac gcctatttaa accagaaagg agagttggat   240
gagattagaa aaataggaga ttataacaaa aaagtttttg aagcaatggg gttaaaggca   300
aaatatgttt atggaagtcc attccagctt gataaggatt atacactgaa tgtctataga   360
ttggctttaa aaactacctt aaaaagagca agaaggagta tggaacttat agcaagagag   420
gatgaaaatc caaaggttgc tgaagttatc tatccaataa tgcaggttaa ttgctatcat   480 tatagggcg  ttgatgttgc agttggaggg atggagcaga gaaaaataca catgttagca   540
agggagcttt taccaaaaaa ggttgtttgt attcacaacc ctgtcttaac gggtttggat   600
ggagaaggaa agatgagttc ttcaaaaggg aattttatag ctgttgatga ctctccagaa   660
gagattaggg ctaagataaa gaaagcatac tgcccagctg gagttgttga aggaaatcca   720
ataatggaga tagctaaata cttccttgaa tatcctttaa ccataaaaag gccagaaaaa   780
tttggtggag atttgacagt taatagctat gaggagttag agagtttatt taaaaataag   840
gaattgcatc caatggattt aaaaaatgct gtagctgaag aacttataaa gattttagag   900
ccaattagaa agagattata a                                            921

<210> SEQ ID NO 9
<211> LENGTH: 921
<212> TYPE: DNA
<213> ORGANISM: Artificial
<220> FEATURE:
<223> OTHER INFORMATION: mutant synthetase derived from Methanococcus
      jannaschii tyrosyl-t
      RNA synthetase

<400> SEQUENCE: 9
atggacgaat tgaaatgat  aaagagaaac acatctgaaa ttatcagcga ggaagagtta    60
agagaggttt aaaaaaaga tgaaaaatct gctggaatag gttttgaacc aagtggtaaa   120
```

-continued

```
atacatttag ggcattatct ccaaataaaa aagatgattg atttacaaaa tgctggattt      180
gatataatta tattgttggc tgatttacac gcctatttaa accagaaagg agagttggat      240
gagattagaa aaataggaga ttataacaaa aagttttttg aagcaatggg gttaaaggca      300
aaatatgttt atggaagtgg attccagctt gataaggatt atacactgaa tgtctataga      360
ttggctttaa aaactacctt aaaaagagca agaaggagta tggaacttat agcaagagag      420
gatgaaaatc caaggttgc tgaagttatc tatccaataa tgcaggttaa ttgtatgcat       480
tatcacggcg ttgatgttgc agttggaggg atggagcaga gaaaaataca catgttagca      540
agggagcttt taccaaaaaa ggttgtttgt attcacaacc ctgtcttaac gggtttggat      600
ggagaaggaa agatgagttc ttcaaaaggg aattttatag ctgttgatga ctctccagaa      660
gagattaggg ctaagataaa gaaagcatac tgcccagctg gagttgttga aggaaatcca      720
ataatggaga tagctaaata cttccttgaa tatcctttaa ccataaaaag gccagaaaaa      780
tttggtggag atttgacagt taatagctat gaggagttag agagtttatt taaaaataag      840
gaattgcatc caatggattt aaaaaatgct gtagctgaag aacttataaa gattttagag      900
ccaattagaa agagattata a                                               921
```

<210> SEQ ID NO 10
<211> LENGTH: 921
<212> TYPE: DNA
<213> ORGANISM: Artificial
<220> FEATURE:
<223> OTHER INFORMATION: mutant synthetase derived from Methanococcus
      jannaschii tyrosyl-t
      RNA synthetase; S1-5 with S at position 107

<400> SEQUENCE: 10

```
atggacgaat ttgaaatgat aaagagaaac acatctgaaa ttatcagcga ggaagagtta       60
agagaggttt taaaaaaaga tgaaaaatct gcttacatag gttttgaacc aagtggtaaa      120
atacatttag ggcattatct ccaaataaaa aagatgattg atttacaaaa tgctggattt      180
gatataatta tattgttggc tgatttacac gcctatttaa accagaaagg agagttggat      240
gagattagaa aaataggaga ttataacaaa aagttttttg aagcaatggg gttaaaggca      300
aaatatgttt atggaagttc attccagctt gataaggatt atacactgaa tgtctataga      360
ttggctttaa aaactacctt aaaaagagca agaaggagta tggaacttat agcaagagag      420
gatgaaaatc caaggttgc tgaagttatc tatccaataa tgcaggttaa tcatgatcat       480
tatatgggcg ttgatgttgc agttggaggg atggagcaga gaaaaataca catgttagca      540
agggagcttt taccaaaaaa ggttgtttgt attcacaacc ctgtcttaac gggtttggat      600
ggagaaggaa agatgagttc ttcaaaaggg aattttatag ctgttgatga ctctccagaa      660
gagattaggg ctaagataaa gaaagcatac tgcccagctg gagttgttga aggaaatcca      720
ataatggaga tagctaaata cttccttgaa tatcctttaa ccataaaaag gccagaaaaa      780
tttggtggag atttgacagt taatagctat gaggagttag agagtttatt taaaaataag      840
gaattgcatc caatggattt aaaaaatgct gtagctgaag aacttataaa gattttagag      900
ccaattagaa agagattata a                                               921
```